US010618896B2

(12) United States Patent
Chipman et al.

(10) Patent No.: US 10,618,896 B2
(45) Date of Patent: Apr. 14, 2020

(54) ALKYL CHAIN MODIFIED IMIDAZOQUINOLINE TLR7/8 AGONIST COMPOUNDS AND USES THEREOF

(71) Applicant: Dynavax Technologies Corporation, Berkeley, CA (US)

(72) Inventors: Stewart D. Chipman, Bainbridge Island, WA (US); John Demattei, Berthoud, CO (US); Radwan Kiwan, Richmond, CA (US); Melissa A. Kachura, Berkeley, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 0 days.

(21) Appl. No.: 16/107,605

(22) Filed: Aug. 21, 2018

(65) Prior Publication Data

US 2019/0062329 A1 Feb. 28, 2019

Related U.S. Application Data

(60) Provisional application No. 62/548,848, filed on Aug. 22, 2017.

(51) Int. Cl.
*C07D 471/04* (2006.01)
*A61P 31/00* (2006.01)
*A61P 35/00* (2006.01)

(52) U.S. Cl.
CPC ............ *C07D 471/04* (2013.01); *A61P 31/00* (2018.01); *A61P 35/00* (2018.01)

(58) Field of Classification Search
CPC .................................................. C07D 471/04
See application file for complete search history.

(56) References Cited

U.S. PATENT DOCUMENTS

| | | | |
|---|---|---|---|
| 4,689,338 A | 8/1987 | Gerster | |
| 5,446,153 A | 8/1995 | Lindstrom et al. | |
| 6,110,929 A | 8/2000 | Gerster et al. | |
| 6,180,095 B1 | 1/2001 | Greenwald | |
| 6,194,425 B1 | 2/2001 | Gerster et al. | |
| 7,199,131 B2 | 4/2007 | Lindstrom | |
| 7,276,248 B2 | 10/2007 | Zalipsky | |
| 7,375,180 B2 | 5/2008 | Gorden | |
| 7,387,271 B2 | 6/2008 | Noelle | |
| 7,427,629 B2 | 9/2008 | Kedl | |
| 7,592,307 B2 | 9/2009 | Zalipsky | |
| 7,799,800 B2 | 9/2010 | Wightman | |
| 7,923,560 B2 | 4/2011 | Wightman | |
| 7,993,659 B2 | 8/2011 | Noelle | |
| 8,329,197 B2 | 12/2012 | Noelle | |
| 8,728,486 B2 * | 5/2014 | David | C07D 471/04 424/193.1 |
| 8,951,528 B2 | 2/2015 | Stoermer | |
| 9,161,976 B2 | 10/2015 | Noelle | |
| 9,441,005 B2 | 9/2016 | David et al. | |
| 9,801,947 B2 | 10/2017 | Miller | |
| 9,962,453 B2 | 5/2018 | Georges | |
| 10,105,426 B2 | 10/2018 | Noelle | |
| 2004/0202720 A1 | 10/2004 | Wightman | |
| 2004/0265351 A1 | 12/2004 | Miller | |
| 2011/0280903 A1 | 11/2011 | Noelle | |
| 2012/0294885 A1 | 11/2012 | David et al. | |
| 2014/0141033 A1 | 5/2014 | Vernejoul | |
| 2015/0141625 A1 | 5/2015 | Stoermer | |
| 2017/0319712 A1 | 11/2017 | Miller | |
| 2018/0311334 A1 | 11/2018 | Gautam | |
| 2019/0015516 A1 | 1/2019 | Jackson | |
| 2019/0083592 A1 | 3/2019 | Noelle | |
| 2019/0125889 A1 | 5/2019 | Georges | |
| 2019/0151462 A1 | 5/2019 | Coffman | |

FOREIGN PATENT DOCUMENTS

| | | | |
|---|---|---|---|
| EP | 2674170 A1 | 12/2013 | |
| EP | 2769738 A1 | 8/2014 | |
| JP | H1180156 A | 3/1999 | |
| WO | WO2004028539 A2 | 4/2004 | |
| WO | WO2004058759 A1 | 7/2004 | |
| WO | WO2005054237 A1 | 6/2005 | |
| WO | WO2006028545 A2 | 3/2006 | |
| WO | WO2007079086 A1 | 7/2007 | |
| WO | WO2013166110 A1 | 11/2013 | |
| WO | WO2014113634 A1 | 7/2014 | |
| WO | WO2015023958 A1 | 2/2015 | |
| WO | WO2015103987 A1 | 7/2015 | |
| WO | WO2015168279 A1 | 11/2015 | |

(Continued)

OTHER PUBLICATIONS

Bao, M. et al. (Jan. 2013). "Regulation of TLR7/9 Signaling in Plasmacytoid Dendritic Cells," *Protein Cell* 4(1):40-52.
Brito, L.A. et al. (2013). "Vaccine Adjuvant Formulations: A Pharmaceutical Perspective," *Seminar Immunol* 25: 130-145.
Dowling, D.J. et al. (Jan. 26, 2017). "TLR7/8 Adjuvant Overcomes Newborn Hyporesponsiveness to Pneumococcal Conjugate Vaccine at Birth," *JCI Insight* 2:e91020, eighteen pages.
Eigenbrod, T. et al. (2015; e-pub. Jun. 22, 2015). "TLR8 Senses Bacterial RNA in Human Monocytes and Plays a Nonredundant Role for Recognition of *Streptococcus pyogenes*," *J Immunol* 195:1092-1099.
Eisenhauer, E.A. et al. (2009). "New Response Evaluation Criteria in Solid Tumours: Revised RECIST Guideline (Version 1.1)," *Eur J Cancer* 45:228-247.
Ganapathi, L. et al. (Aug. 14, 2015). "The Imidazoquinoline Toll-Like Receptor-7/8 Agonist Hybrid-2 Potently Induces Cytokine Production by Human Newborn and Adult Leukocytes," *PLoS One* 10(8):e0134640, 12 pages.

(Continued)

*Primary Examiner* — Rei Tsang Shiao
(74) *Attorney, Agent, or Firm* — Morrison & Foerster LLP

(57) ABSTRACT

Disclosed are alkyl chain modified 1H-imidazoquinoline compounds, derivatives and analogs thereof, as Toll-like receptor-7 and -8 agonists for enhancing immune responses. Also provided are methods of making pharmaceutical compositions containing these compounds. The present disclosure also describes methods of use for the alkyl chain modified 1H-imidazoquinoline compounds, derivatives and analogs thereof, and pharmaceutical compositions containing these compounds for the treatment of disease in a subject.

15 Claims, 5 Drawing Sheets

(56) References Cited

FOREIGN PATENT DOCUMENTS

| WO | WO2016055812 A1 | 4/2016 |
|---|---|---|
| WO | WO2017044803 A1 | 3/2017 |
| WO | WO2017072662 A1 | 5/2017 |
| WO | WO2018198091 A1 | 11/2018 |
| WO | WO2019099412 A1 | 5/2019 |

OTHER PUBLICATIONS

Gorden, K.B. et al. (2005). "Synthetic TLR Agonists Reveal Functional Differences Between Human TLR7 and TLR8," *J Immunol* 174:1259-1268.

Gosu, V. et al. (Nov. 14, 2012). "Therapeutic Applications of Nucleic Acids and Their Analogues in Toll-like Receptor Signaling,"*Molecules* 17:13503-13529.

Hemmi, H. et al. (Feb. 2002, e-pub. Jan. 22, 2002). "Small Anti-Viral Compounds Activate Immune Cell via the TLR7 MyD88-Dependent Signaling Pathway," *Nat Immunol* 3(2):196-200.

Lu, H. et al. (Jan. 15, 2012; e-pub. Nov. 29, 2011). "VTX-2337 is a Novel TLR8 Agonist That Activates NK Cells and Augments ADCC," *Clin Cancer Res* 18(2):499-509.

Patil, S.A. et al. (2016). "Imidazoquinolines: Recent Developments in Anticancer Activity," *Mini Rev Med Chem.* 16(4):309-322.

Pockros, P. et al. (Aug. 2007). "Oral Resiquimod in Chronic HCV Infection: Safety and Efficacy in 2 Placebo-Controlled, Double-Blind Phase IIa Studies," *J Hepatol* 47(2):174-182.

Pramanick, S. et al. (Mar. 2013). "Excipient Selection in Parenteral Formulation Development," *Pharma Times* 45(3):65-77.

Rice, J. et al. (2002). "Critical Components of a DNA Fusion Vaccine Able to Induce Protective Cytotoxic T Cells Against a Single Epitope of a Tumor Antigen," *J Immunol* 169:3908-3913.

Sabado, R.L. et al. (Mar. 2015). "Resiquimod as an Immunologic Adjuvant for NY-ESO-1 Protein Vaccination in Patients with High Risk Melanoma," *Cancer Immunol Res* 3(3):278-287, 20 pages.

Savage, P. et al. (1996). "A Phase I Clinical Trial of Imiquimod, an Oral Interferon Inducer, Administered Daily," *Br J Cancer* 74:1482-1486.

Shukla, N. M. et al. (Nov. 15, 2010). "Syntheses of Fluorescent Imidazoquinoline Conjugates as Probes of Toll-Like Receptor 7," *Bioorg Med Chem Lett* 20(22):6384-6386, nine pages.

Shukla, N.M. et al. (2010). "Structure—Activity Relationships in Human Toll-Like Receptor 7—Active Imidazoquinoline Analogues," *J Med Chem* 53(11):4450-4465, with supplementary information, 141 pages.

Singh, M. et al. (2014; e-pub. Sep. 24, 2014). "Effective Innate and Adaptive Antimelanoma Immunity Through Localized TLR7/8 Activation," *J Immunol* 193:4722-4731.

Spinetti, T. et al. (2016). "TLR7-Based Cancer Immunotherapy Decreases Intratumoral Myeloid—Derived Suppressor Cells and Blocks Their Immunosuppressive Function,"*Oncoimmunol* 5(11):e1230578, 8 pages.

Takeuchi, O. et al. (Mar. 19, 2010). "Pattern Recognition Receptors and Inflammation," *Cell* 140:805-820.

Tanji, H. et al. (Feb. 2015; e-pub. Jan. 19, 2015). "Toll-Like Receptor 8 Senses Degradation Products of Single-Stranded RNA," *Nat Struct Mol Biol* 22(2):109-115.

Van Haren, S.D. et al. (2016; e-pub. Oct. 28, 2016). "Age-Specific Adjuvant Synergy: Dual TLR7/8 and Mincle Activation of Human Newborn Dendritic Cells Enables Th1 Polarization," *J Immunol* 197:4413-4424.

Van Hoeven, N. et al. (Apr. 21, 2017). "A Formulated TLR7/8 Agonist is a Flexible, Highly Potent and Effective Adjuvant for Pandemic Influenza Vaccines," *Sci Rep* 7:46426, pp. 1-15.

Vasilakos, J.P. et al. (2013). "The Use of Toll-Like Receptor 7/8 Agonists as Vaccine Adjuvants," *Expert Rev Vaccines* 12(7):809-819.

Wang, S. et al. (2016; e-pub. Oct. 31, 2016). "Intratumoral Injection of a CpG Oligonucleotide Reverts Resistance to PD-1 Blockade by Expanding Multifunctional $CD8^+T$ Cells," *PNAS* 113:E7240-E7249.

Zhang, Z. et al. (Oct. 18, 2016). "Structural Analysis Reveals that Toll-like Receptor 7 is a Dual Receptor for Guanosine and Single-Stranded RNA," *Immunity* 45:737-748.

International Search Report and Written Opinion dated Nov. 6, 2018 for PCT Application No. PCT/US2018/047323, filed on Aug. 21, 2018, 12 pages.

Kim, W.G. et al. (Sep. 21, 2016, e-pub Aug. 19, 2016). "Covalent Conjugation of Small-Molecule Adjuvants to Nanoparticle Induces Robust Cytotoxic T Cell Responses via DC Activation," Bioconjugate Chemistry 27(9):2007-2013.

Shukla, N.M. et al. (Aug. 28, 2012). "Potent Adjuvanticity of a Pure TLR7—Agonistic Imidazoquinoline Dendrimer," PLoS One 7(8):e43612, 11 pages.

Shukla, N.M. et al. (Feb. 9, 2012, e-pub. Jan. 27, 2012). "Toll-Like Receptor (TLR)-7 and -8 Modulatory Activities of Dimeric Imidazoquinolines," Journal of Medicinal Chemistry 55(3):1106-1116, 26 pages.

Shukla, N.M. et al. (Jun. 1, 2011). "Toward Self-Adjuvanting Subunit Vaccines: Model Peptide and Protein Antigens Incorporating Covalently Bound Toll-Like Receptor-7 Agonistic Imidazoquinolines," Bioorganic & Medicinal Chemistry Letters 21(11):3232-3236, 15 pages.

Agarwal, P. et al. (2013; e-pub. May 28, 2013). "Hydrazino-Pictet-Spengler Ligation as a Biocompatible Method for the Generation of Stable Protein Conjugates," Bioconjug Chem 24(6):846-851.

Beck, A. et al. (May 2017; e-pub. Mar. 17, 2017). "Strategies and Challenges for the Next Generation of Antibody—Drug Conjugates," Nature Rev Drug Discovery 16(5):315-337.

Beesu, M. et al. (2015; e-pub. Sep. 9, 2015). "Structure-Based Design of Human TLR8—Specific Agonists with Augmented Potency and Adjuvanticity,"J Med Chem 58(19):7833-7849.

Blencowe, C.A. et al. (2011). "Self-immolative Linkers in Polymeric Delivery Systems," Polymer Chem 2:773-790.

Brülisauer, L. et al. (Dec. 10, 2014; e-pub. Jun. 18, 2014). "Disulfide—Containing Parenteral Delivery Systems and their Redox—Biological Fate," J Controlled Release 195:147-154.

Caballero, O.L. et al. (Nov. 2009; e-pub. Aug. 27, 2009). "Cancer/testis (CT) Antigens: Potential Targets for Immunotherapy," Cancer Science 100(11):2014-2021.

Carlmark, A. et al. (Apr. 30, 2013). "Dendritic Architectures Based on bis-MPA: Functional Polymeric Scaffolds for Application—Driven Research," Chem. Soc. Rev. 42:5858-5879.

Cheever, M.A. et al. (Sep. 1, 2009). "The Prioritization of Cancer Antigens: A National Cancer Institute Pilot Project for the Acceleration of Translational Research," Clinical Cancer Research 15(17):5323-5337.

Desrichard, A. et al. (Feb. 15, 2016; e-pub. Oct. 29, 2015). "Cancer Neoantigens and Applications for Immunotherapy," Clinical Cancer Res. 22(4):807-812.

Doronina, S.O. et al. (Jul. 2003). "Development of Potent Monoclonal Antibody Auristatin Conjugates for Cancer Therapy," Nat. Biotechnol. 21(7):778-784.

Dorywalska, M. et al. (Apr. 15, 2015; e-pub. Feb. 2, 2015). "Effect of Attachment Site on Stability of Cleavable Antibody Drug Conjugates," Bioconjug Chem 26(4):650-659.

Dubowchik, G.M. et al. (2002), "Cathepsin B-Labile Dipeptide Linkers for Lysosomal Release of Doxorubicin from Internalizing Immunoconjugates: Model Studies of Enzymatic Drug Release and Antigen-Specific in Vitro Anticancer Activity," Chem. 13(4):855-869.

Flygare, J.A. et al. (Jan. 2013). "Antibody—Drug Conjugates for the Treatment of Cancer," Chem Biol Drug Des 81(1):113-121.

Francica, J.R. et al. (Sep. 1, 2016). "Thermoresponsive Polymer Nanoparticles Co-Deliver RSV F Trimers with a TLR-7/8 Adjuvant," Bioconjugate Chemistry 27(10):2372-2385.

Gadd, A.J.R. et al. (Jul. 1, 2015). "Targeted Activation of Toll-Like Receptors: Conjugation of a Toll-Like Receptor 7 Agonist to a Monoclonal Antibody Maintains Antigen Binding and Specificity," Bioconjugate Chem 26:1743-1752.

Grünewald, J. et al. (Jul. 19, 2017; e-pub. Jun. 7, 2017). "Optimization of an Enzymatic Antibody—Drug Conjugation Approach Based on Coenzyme A Analogs," Bioconjug Chem 28(7):1906-1915.

(56) References Cited

OTHER PUBLICATIONS

Hamann, P.R. et al. (Jan.-Feb. 2002; e-pub. Dec. 19, 2001). "An Anti-CD33 Antibody—Calicheamicin Conjugate for Treatment of Acute Myeloid Leukemia. Choice of Linker," Bioconjugate Chem 13(1):40-46.

International Search Report and Written Opinion dated Mar. 1, 2019 for PCT Application No. PCT/US2018/060849 filed on Nov. 13, 2018, 19 pages.

Jacobsen, F.W. et al. (Feb. 3, 2017). "Engineering an IgG Scaffold Lacking Effector Function with Optimized Developability," J Biol Chem 292(5):1865-1875.

Jain, N. et al. (Nov. 2015, e-pub. Mar. 11, 2015). "Current ADC Linker Chemistry," Pharma Res 32 (11):3526-3540.

Junutula J.R. et al. (2008), "Site-specific conjugation of cytotoxic drug to an antibody improves the therapeutic index," Nat Biotechnol. 26(8):925-932.

Kato, A. et al. (2017; e-pub. Jul. 20, 2017). "Extensive Survey of Antibody Invariant Positions for Efficient Chemical Conjugation Using Expanded Genetic Codes," Bioconjug Chem 28(8):2099-2108.

Kim, M.T. et al. (Jul. 16, 2014; e-pub. May 29, 2014). "Statistical Modeling of the Drug Load Distribution on Trastuzumab Emtansine (Kadcyla), a Lysine-Linked Antibody Drug Conjugate," Bioconjugate Chem 25(7):1223-1232.

Kolb, H.C. et al. (Dec. 2003). "The Growing Impact of Click Chemistry on Drug Discovery," Drug Discov Today 8(24):1128-1137.

Kolb, H.C. et al. (Jun. 1, 2001; e-pub. May 28, 2001). "Click Chemistry: Diverse Chemical Function from a Few Good Reactions," Angew Chem Int Ed Engl 40(11):2004-2021.

Kunert, R. et al. (Apr. 2016, e-pub. Mar. 3, 2016). "Advances in Recombinant Antibody Manufacturing," Appl Microbiol Biotechnol 100(8):3451-3461.

Kung-Sutherland, M.S. et al. (Aug. 2013; e-pub. Jun. 14, 2013). "SGN-CD33A: A Novel CD33-targeting Antibody—Drug Conjugate Utilizing a Pyrrolobenzodiazepine Dimer is Active in Models of Drug-Resistant AML," Blood 122(8):1455-1463.

Lambert, J.M. (2012; e-pub. Nov. 23, 2012). "Drug—Conjugated Antibodies for the Treatment of Cancer," Br J Clin Pharmacol 76(2):248-262.

Lebeau, A.M. et al. (Jan. 2, 2013; e-pub. Dec. 17, 2012). "Imaging a Functional Tumorigenic Biomarker in the Transformed Epithelium," Proc Nat Acad Sci USA 110(1):93-98.

Liu, C. et al. (Jun. 1, 2003). "Overexpression of Legumain in Tumors is Significant for Invasion/Metastasis and a Candidate Enzymatic Target for Prodrug Therapy," Cancer Res 63:2957-2964.

Lu, J. et al. (Apr. 14, 2016). "Linkers Having a Crucial Role in Antibody—Drug Conjugates," Int J Mol Sci 17(4):561, pp. 1-22.

Lyon, R.P. et al. (Jul. 2015; e-pub. Jun. 15, 2015). "Reducing Hydrophobicity of Homogeneous Antibody—Drug Conjugates Improves Pharmacokinetics and Therapeutic Index," Nat Biotechnol 33(7):733-735.

Lyon, R.P. et al. (Oct. 2014, e-pub. Sep. 7, 2014). "Self-hydrolyzing Maleimides Improve the Stability and Pharmacological Properties of Antibody-Drug Conjugates," Nat Biotechnol 32(10):1059-1062.

Mason, S.D. et al. (Apr. 2011; e-pub. Jan. 12, 2011). "Proteolytic Networks in Cancer," Trends Cell Biol 21 (4):228-237, 18 pages.

Okeley, N.M. et al. (Oct. 16, 2013; e-pub. Sep. 19, 2013). "Metabolic Engineering of Monoclonal Antibody Carbohydrates for Antibody—Drug Conjugation," Bioconjug Chem 24(10):1650-1655.

Puthenveetil, S. et al. (May 30, 2017). "Multivalent Peptidic Linker Enables Identification of Preferred Sites of Conjugation for a Potent Thialanstatin Antibody Drug Conjugate," PlosOne 12(5):e0178452, 16pgs.

Sadowsky, J.D. et al. (Aug. 16, 2017; e-pub. Jun. 21, 2017). "Development of Efficient Chemistry to Generate Site-Specific Disulfide-Linked Protein- and Peptide—Payload Conjugates: Application to THIOMAB Antibody—Drug Conjugates," Bioconjug Chem 28(8):2086-2098.

Sau, S. et al. (Oct. 2017; Jun. 13, 2017). "Advances in Antibody—Drug Conjugates: A New Era of Targeted Cancer Therapy," Drug Discov Today 22(10):1547-1556.

Schumacher, T.N. et al. (Apr. 3, 2015). "Neoantigens in Cancer Immunotherapy," Science 348(6230):69-74.

Smirnov, D. et al. (Jul. 26, 2011). "Vaccine Adjuvant Activity of 3M-052: An Imidazoquinoline Designed for Local Activity Without Systemic Cytokine Induction," Vaccine 29(33):5434-5442.

Sun, M.C. et al. (2005). "Reduction—Alkylation Strategies for the Modification of Specific Monoclonal Antibody Disulfides," Bioconjug Chem 16(5):1282-1290, 22 pages.

Sun, X. et al. (2017; e-pub. Apr. 7, 2017). "Effects of Drug—Antibody Ratio on Pharmacokinetics, Biodistribution, Efficacy, and Tolerability of Antibody—Maytansinoid Conjugates," Bioconjug Chem 28(5):1371-1381.

Tanabe, L.M. et al. (2017). "The Role of Type II Transmembrane Serine Protease—Mediated Signaling in Cancer," FEBS J 284:1421-1436.

Tang, F. et al. (Aug. 2017; e-pub. Jul. 27, 2017). "Chemoenzymatic Synthesis of Glycoengineered IgG Antibodies and Glycosite-Specific Antibody—Drug Conjugates," Nature Protocols 12(8):1702-1721, 44 pages.

Tian. F. et al. (Feb. 4, 2014). "A General Approach to Site-Specific Antibody Drug Conjugates," Proc Nat Acad Sci USA 111(5):1766-1771.

Uhland, K. (Dec. 2006). "Matriptase and its Putative Role in Cancer," Cell Mol Life Sci 63(24):2968-2978.

Ulisse, S. et al. (2009). "The Urokinase Plasminogen Activator System: A Target for Anti-Cancer Therapy," Curr Cancer Drug Targets 9(1):32-71.

Wagh, A. et al. (Feb.-Mar. 2018; e-pub. Jan. 2018). "Challenges and New Frontiers in Analytical Characterization of Antibody—Drug Conjugates," MABS 10(2):222-243.

Wang, R.-F. et al. (Jan. 2017; e-pub. Dec. 27, 2016). "Immune Targets and Neoantigens for Cancer Immunotherapy and Precision Medicine," Cell Research 27(1):11-37.

Warncke, M. et al. (2012; e-pub. Mar. 28, 2012). "Different Adaptations of IgG Effector Function in Human and Nonhuman Primates and Implications for Therapeutic Antibody Treatment," J Immunol 188:4405-4411.

Weidle, U.H. et al. (2014). "Proteases as Activators for Cytotoxic Prodrugs in Antitumor Therapy," Cancer Genomics Proteomics 11:67-79.

Weidle, U.H. et al. (Oct. 2014). "Tumor-Antigen—Binding Bispecific Antibodies for Cancer Treatment," Seminars in Oncology 41(5):653-660.

Wille-Reece, U. et al. (Oct. 18, 2005; e-pub. Oct. 11, 2005). "HIV Gag Protein Conjugated to a Toll-Like Receptor 7/8 Agonist Improves the Magnitude and Quality of Th1 and CD8+ T Cell Responses in Nonhuman Primates," Proc. Nat'l Acad. Sci. 102(42):15190-15194.

Yang et al. (Sep. 12, 2006). "Evaluation of Disulfide Reduction During Receptor-Mediated Endocytosis by Using FRET Imaging," PNAS 103(37):13872-13877.

Zhou, Q. et al. (2014; e-pub. Feb. 17, 2014). "Site-Specific Antibody—Drug Conjugation Glycoengineering," Bioconjug Chem 25(3):510-520.

\* cited by examiner

Time Post Injection (hours)

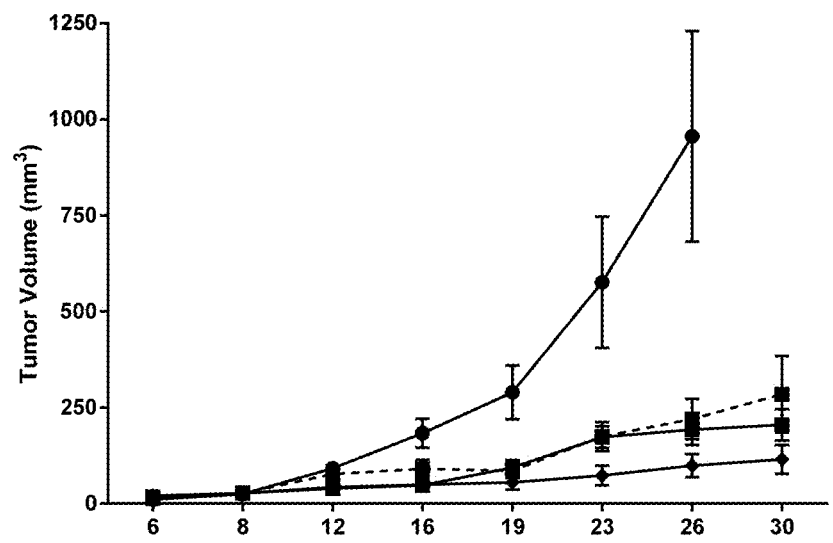
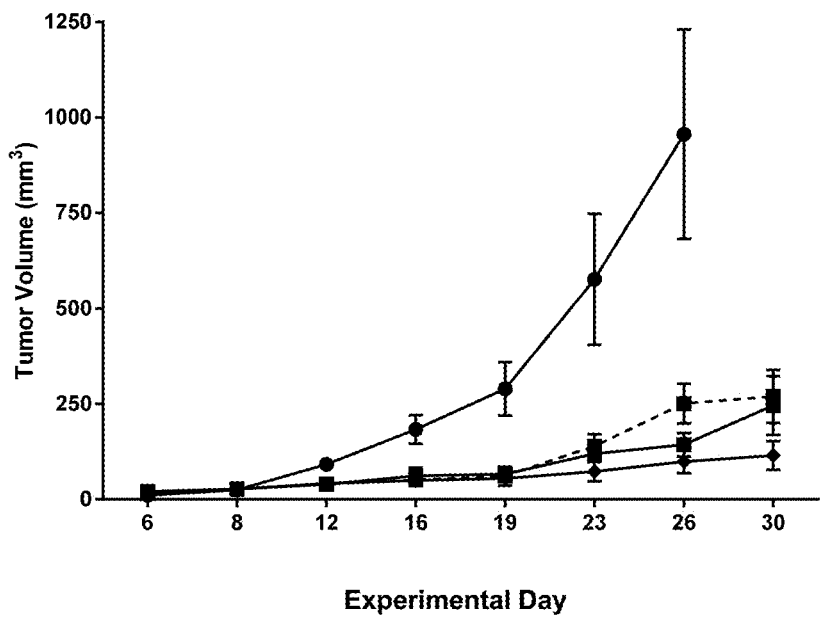

Experimental Day

ALKYL CHAIN MODIFIED IMIDAZOQUINOLINE TLR7/8 AGONIST COMPOUNDS AND USES THEREOF

CROSS-REFERENCE TO RELATED APPLICATIONS

This application claims priority to and the benefit of U.S. Provisional Patent Application No. 62/548,848, filed Aug. 22, 2017, the disclosure of which is incorporated herein by reference in its entirety.

FIELD OF THE INVENTION

The present disclosure relates to alkyl chain modified imidazoquinoline TLR7/8 agonist compounds for enhancing immune responses. The present disclosure also relates to pharmaceutical compositions comprising the alkyl chain modified imidazoquinoline compounds, methods of preparation thereof, methods for stimulating an immune response, and uses of the pharmaceutical compositions in the treatment of disease in a subject, e.g., infectious disease and cancer.

BACKGROUND OF THE INVENTION

Toll-like receptors (TLRs) are a family of transmembrane proteins that recognize structurally conserved molecules that are derived from and unique to pathogens, referred to as pathogen-associated molecular patterns. As such, TLRs function in the mammalian immune system as front-line sensors of pathogen-associated molecular patterns, detecting the presence of invading pathogens (Takeuchi and Akira 2010 *Cell* 140:805-820). TLR engagement in sentinel immune cells causes biosynthesis of selected cytokines (e.g., type I interferons), induction of co-stimulatory molecules, and increased antigen presentation capacity. These are important molecular mechanisms that activate innate and adaptive immune responses. Accordingly, agonists and antagonists of TLRs find use in modulating immune responses. TLR agonists are typically employed to stimulate immune responses, whereas TLR antagonists are typically employed to inhibit immune responses (Gosu et al 2012 *Molecules* 17:13503-13529).

The human genome contains 10 known TLRs, of these TLR3, TLR7, TLR8, and TLR9 sense nucleic acids and their degradation products. The distribution of TLR7, TLR8, and TLR9 is restricted to the endolysosomal compartments of cells and they are preferentially expressed in cells of the immune system. In the activated, dimeric receptor configuration TLR7 and TLR8 recognize single stranded RNA at one ligand binding site and the ribonucleoside degradation products guanosine and uridine, respectively, (as well as small molecule ligands with related structural motifs) at a second ligand binding site (Zhang et al 2016 *Immunity* 45:737-748; Tanji et al 2015 *Nat Struct Mol Biol* 22:109-115). Engagement of TLR7 in plasmacytoid dendritic cells leads to the induction of interferon-α/β, which plays essential functions in the control of the adaptive immune response (Bao and Liu 2013 *Protein Cell* 4:40-52). Engagement of TLR8 in myeloid dendritic cells, monocytes, and monocyte-derived dendritic cells induces a prominent pro-inflammatory cytokine profile, characterized by increased production of tumor necrosis factor-α, interleukin-12, and IL-18 (Eigenbrod et al 2015 *J Immunol* 195:1092-1099). Thus, virtually all major types of monocytic and dendritic cells can be activated by agonists of TLR7 and TLR8 to become highly effective antigen-presenting cells, thereby promoting an effective innate and adaptive immune response. Most antigen presenting cell types express only one of these two receptors, accordingly small molecules with potent agonist bioactivity against both TLR7 and TLR8 receptors are potentially more effective immune adjuvants than agonists specific for only one of these TLRs. Thus a TLR7/TLR8 (TLR7/8) small molecule agonist with balanced, dual bioactivity would cause innate immune responses in a wider range of antigen presenting cells and other key immune cell types, including plasmacytoid and myeloid dendritic cells, monocytes, and B cells (van Haren et al 2016 *J Immunol* 197:4413-4424; Ganapathi et al 2015 *PLoS One* 10:e0134640). Such potent dual TLR7/8 agonists may also be effective in stimulating effective anti-tumor immune responses in cancer (Singh et al 2014 *J Immunol* 193:4722-4731; Sabado et al 2015 *Cancer Immunol Res* 3:278-287; Spinetti et al 2016 *Oncoimmunol* 5:e1230578; Patil et al 2016 *Mini Rev Med Chem* 16:309-322).

A number of small molecule structural classes are known to interact at the guanosine/uridine ligand binding site and possess varying levels of TLR 7 and/or TLR8 agonist bioactivity (see e.g., Lu et al 2012 *Clin Cancer Res* 18:499-509; U.S. Pat. Nos. 5,446,153, 6,194,425, 6,110,929, and 7,199,131), including derivatives of 1H-imidazo[4,5-c]quinoline that are TLR7 agonists or dual TLR7/8 agonists (see e.g., Vasilakos and Tomai 2013 *Expert Rev Vaccines* 12:809-819; U.S. Pat. No. 4,689,338). One such 1H-imidazo[4,5-c]quinoline is 1-isobutyl-1H-imidazo[4,5-c]quinolin-4-amine (Imiquimod), a TLR7-specific agonist that was approved in 1997 for the treatment of actinic keratosis, superficial basal cell carcinoma, and genital warts, and was subsequently approved for the treatment of basal cell carcinoma (see e.g., Hemmi et al 2002 *Nat Immunol* 3:196-200). While some 1H-imidazo[4,5-c]quinolines display selective TLR7 or TLR8 agonist activities, others display dual TLR7/8 agonist activities. For example, 1-benzyl-2-butyl-1H-imidazo[4,5-c]quinolin-4-amine was found to be a TLR7 agonist with negligible bioactivity against TLR8 (Shukla et al 2010 *J Med Chem* 53:4450-4465). In contrast, 2-propyl[1,3]thiazolo[4,5-c]quinolin-4-amine was found to be a TLR8 agonist with negligible activity against TLR7 (Gorden et al 2005 *J Immunol* 174:1259-1268). 1-(4-aminomethylbenzyl)-2-butyl-1H-imidazo[4,5-c]quinolin-4-amine (IMDQ) and 1-(3-aminomethylbenzyl)-2-butyl-1H-imidazo[4,5-c]quinolin-4-amine (meta-IMDQ) were found to be dual TLR7/8 agonists with potent agonist activity against both receptors (see e.g., Shukla et al 2010 *J Med Chem* 53:4450-4465; Shukla et al 2010 *Bioorg Med Chem Lett* 10:6384-6386; U.S. Pat. Nos. 8,728,486; 9,441,005).

However, rapid systemic distribution of soluble 1H-imidazo[4,5-c]quinoline-based TLR7/8 agonists following subcutaneous, intratumoral or intramuscular administration has been demonstrated to cause significant toxicities in patients (see e.g., Vasilakos et al 2013 *Expert Rev Vaccines* 12:809-819; Savage et al 1996 *Br J Cancer* 74:1482-1486; Pockros et al 2007 *J Hepatol* 47:174-182). Systemic immune system activation due to activation of TLRs in cells of the spleen and liver causes an increase in serum pro-inflammatory cytokine levels, which in turn causes flu-like symptoms and other adverse events that limits the utility of these compounds as human therapeutics to a topical route of administration. Thus, there remains a need for small molecule therapeutic agents with potent and balanced TLR7/8 agonist activities that also possess physiochemical properties that enable pharmaceutical compositions that promote retention of the compound at the site of injection.

BRIEF SUMMARY OF THE INVENTION

The present disclosure provides alkyl chain modified 1H-imidazo[4,5-c]quinoline derivatives that are potent TLR7/8 agonists exhibiting balanced bioactivity against both receptors. In one aspect, provided is a compound of formula (J):

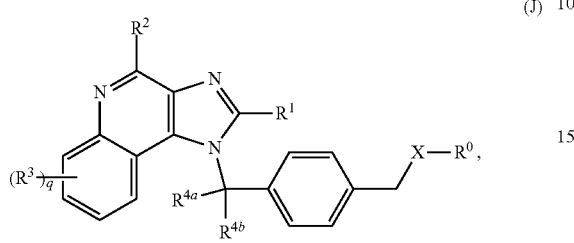

or a salt thereof, wherein:

$R^0$ is $C_4$-$C_{21}$ hydrocarbyl optionally substituted by 1 to 4 halogen atoms;

X is —NH— or —NH(C=O)—;

$R^1$ is $C_3$-$C_6$ alkyl, —$(CH_2)_p OR^{1a}$, —$(CH_2)_p NHR^{1b}$, or —$(CH_2)_p R^{1c}$; where $R^{1a}$ and $R^{1b}$ are independently $C_1$-$C_3$ alkyl; $R^{1c}$ is $C_3$-$C_4$ cycloalkyl; and p is 1 or 2;

$R^2$ is $NHR^{2a}$; where $R^{2a}$ is H, OH, $NH_2$, or methyl;

each $R^3$ is independently halogen, $C_1$-$C_8$ alkyl, —($C_1$-$C_7$ alkylene)-$NH_2$, or —$CH_2$-phenylene-$CH_2NH_2$;

q is 0, 1, 2, 3, or 4; and $R^{4a}$ and $R^{4b}$ are independently H or $C_1$-$C_8$ alkyl, provided that the compound is other than 2-butyl-1-(4-((hexadecylamino)methyl)benzyl)-1H-imidazo[4,5-c]quinolin-4-amine (Compound No. 63-32); N-(4-((4-amino-2-butyl-1H-imidazo[4,5-c]quinolin-1-yl)methyl)benzyl) palmitamide (Compound No. 63-31); or N-(4-((4-amino-2-butyl-1H-imidazo[4,5-c]quinolin-1-yl)methyl)benzyl)pent-4-ynamide (Compound No. 63-37).

In some embodiments, $R^0$ is $C_4$-$C_{14}$ hydrocarbyl.

In some embodiments, X is —NH(C=O)—. In some embodiments, X is —NH—.

In some embodiments, $R^0$ is branched $C_4$-$C_{14}$ alkyl, —$(CH_2)_z(C(CH_3)_2)R^4$, or —$(CH_2)_m R^4$; m is 0, 1, 2, or 3; z is 1 or 2; and $R^4$ is $C_3$-$C_8$ cycloalkyl optionally substituted by 1 to 4 groups independently selected from the group consisting of $C_1$-$C_4$ alkyl and $C_1$-$C_4$ alkylene.

In some embodiments, $R^0$ is branched $C_4$-$C_{14}$ alkyl.

In some embodiments, $R^0$ is —$(CH_2)_m R^4$. In one variation, m is 1 or 2, and $R^4$ is cyclopropyl, cyclobutyl, or cyclopentyl.

In some embodiments, $R^0$ is —$(CH_2)_z(C(CH_3)_2)R^4$. In one variation, z is 1, and $R^4$ is cyclopropyl, cyclobutyl, or cyclopentyl.

In some embodiments, $R^4$ is $C_3$-$C_8$ cycloalkyl.

In some embodiments, $R^4$ is $C_3$-$C_6$ cycloalkyl optionally substituted by 1 to 3 groups independently selected from the group consisting of methyl and methylene. In one variation, m is 1 or 2.

In some embodiments, $R^4$ is cyclopropyl optionally substituted by 1 to 3 groups independently selected from the group consisting of methyl and methylene, and m is 1 or 2.

In some embodiments, m is 0 or 1, and $R^4$ is cyclohexyl optionally substituted by 1 to 3 groups independently selected from the group consisting of methyl and methylene.

In some embodiments, $R^0$ is selected from the group consisting of:

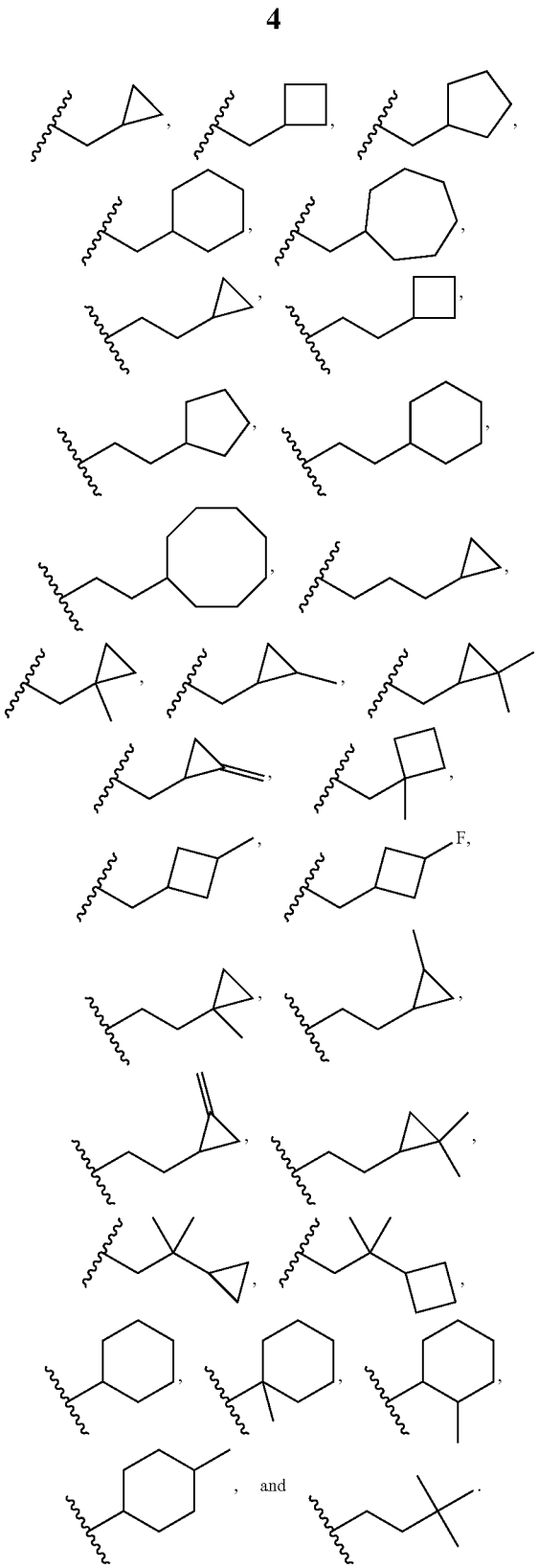

In some embodiments, $R^1$ is $C_3$-$C_6$ alkyl (e.g., n-butyl). In some embodiments, $R^1$ is —$(CH_2)_p OR^{1a}$ (e.g., $CH_2OCH_2CH_3$). In some embodiments, $R^1$ is —$(CH_2)_p NHR^{1b}$ (e.g., $CH_2NHCH_2CH_3$). In some embodiments, $R^1$ is —$(CH_2)_p R^{1c}$. In one variation, $R^{1c}$ is cyclopropyl.

In some embodiments, $R^2$ is $NH_2$.

In some embodiments, q is 0. In some embodiments, q is 1 and $R^3$ is $C_1$-$C_8$ alkyl.

In some embodiments, each $R^{4a}$ and $R^{4b}$ is H.

In some embodiments, the compound is selected from the group consisting of Compound Nos. 63-33 to 63-36 and 63-38 to 63-49 in Table 1, or a salt thereof.

In another aspect, provided is a compound of formula (K):

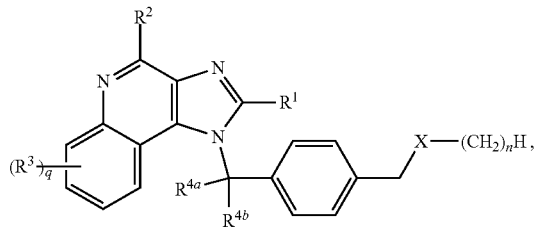

(K)

or a salt thereof, wherein:
n is an integer from 4 to 21;
X is —NH— or —NH(C=O)—;
$R^1$ is $C_3$-$C_6$ alkyl, —$(CH_2)_pOR^{1a}$, —$(CH_2)_pNHR^{1b}$ or —$(CH_2)_pR^{1c}$; where $R^{1a}$ and $R^{1b}$ are independently $C_1$-$C_3$ alkyl; $R^{1c}$ is $C_3$-$C_4$ cycloalkyl; and p is 1 or 2;
$R^2$ is $NHR^{2a}$; where $R^{2a}$ is H, OH, $NH_2$, or methyl;
each $R^3$ is independently halogen, $C_1$-$C_8$ alkyl, —($C_1$-$C_7$ alkylene)-$NH_2$, or —$CH_2$-phenylene-$CH_2NH_2$;
q is 0, 1, 2, 3, or 4; and
$R^{4a}$ and $R^{4b}$ are independently H or $C_1$-$C_8$ alkyl,
provided that the compound is other than 2-butyl-1-(4-((hexadecylamino)methyl)benzyl)-1H-imidazo[4,5-c]quinolin-4-amine (Compound No. 63-32) or N-(4-((4-amino-2-butyl-1H-imidazo[4,5-c]quinolin-1-yl)methyl)benzyl) palmitamide (Compound No. 63-31).

In some embodiments, X is —NH—. In one variation, n is an integer from 4 to 15. In another variation, n is 4, 5, 6, or 7.

In some embodiments, X is —NH(C=O)—. In one variation, n is 11, 12, 13, or 14.

In some embodiments, $R^1$ is $C_3$-$C_6$ alkyl (e.g., n-butyl). In some embodiments, $R^1$ is —$(CH_2)_pOR^{1a}$ (e.g., $CH_2OCH_2CH_3$). In some embodiments, $R^1$ is —$(CH_2)_p$ $NHR^{1b}$ (e.g., $CH_2NHCH_2CH_3$). In some embodiments, $R^1$ is —$(CH_2)_pR^{1c}$. In one variation, $R^{1c}$ is cyclopropyl.

In some embodiments, $R^2$ is $NH_2$.

In some embodiments, q is 0. In some embodiments, q is 1 and $R^3$ is $C_1$-$C_8$ alkyl.

In some embodiments, each $R^{4a}$ and $R^{4b}$ is H.

In some embodiments, the compound is selected from the group consisting of Compound Nos. 63-01 to 63-30 in Table 1, or a salt thereof.

Further provided are pharmaceutical compositions comprising (i) a compound of formula (J) or (K) and (ii) one or more pharmaceutically acceptable excipients. In some embodiments, the pharmaceutical compositions further comprise an antigen. In some embodiments, the pharmaceutical composition is comprised of pharmaceutically acceptable excipients that include USP-grade oils and an organic modifier (e.g., 95% sesame oil/5% ethanol). In some embodiments, the pharmaceutical composition is comprised of pharmaceutically acceptable excipients that enable an oil-in-water nanoemulsion or a liposomal formulation, examples of which are known to those skilled in the art. In some embodiments, the pharmaceutical composition can include an admixture of an antigen or antigens, including but not limited to tumor associated antigens or neoantigens.

The present disclosure also provides a method of stimulating an immune response in a mammalian subject in need thereof, comprising administering to the mammalian subject a pharmaceutical composition as described above in an amount, at a frequency, and over a time frame sufficient to stimulate an immune response in the mammalian subject. In one aspect, the immune response is a local immune response. In another aspect, the immune response is a systemic immune response.

The present disclosure also provides a plurality of methods for using a pharmaceutical composition described above in a mammalian subject, such as a human patient. In one aspect, methods are provided for treating cancer in a mammalian subject in need thereof, comprising administering to the mammalian subject the pharmaceutical composition in an amount sufficient to treat cancer in the mammalian subject. In another aspect of the method, intratumoral delivery comprises injection of the pharmaceutical composition into at least one tumor lesion. In one aspect of the method, an effective amount of a second therapeutic agent is further administered to the subject. In certain embodiments, the second therapeutic agent is a chemotherapeutic agent, an epigenetic modulator, inducer of immunogenic cell death, or an antagonist of an inhibitory immune checkpoint molecule. In another aspect, methods are provided for inducing an antigen-specific antibody response in a mammalian subject in need thereof, comprising administering to the mammalian subject the pharmaceutical composition in an amount sufficient to induce an antigen-specific antibody response and/or an antigen-specific T cell response in the mammalian subject. In one aspect, methods are provided for treating or preventing an infectious disease in a mammalian subject in need thereof, comprising administering to the mammalian subject the pharmaceutical composition in an amount sufficient to treat or prevent an infectious disease in the mammalian subject. In one aspect, methods are provided for treating or preventing an IgE-related disorder in a mammalian subject, comprising administering the pharmaceutical composition in an amount sufficient to treat or prevent an IgE-related disorder in the mammalian subject.

Also provided in the invention are kits comprising pharmaceutical compositions of the invention, and instructions for use in the treatment of infectious diseases and/or cancers. Methods are also provided for the manufacture of kits for use in the treatment of infectious disease and/or cancer.

BRIEF DESCRIPTION OF THE DRAWINGS

FIGS. 2A-C show tumor growth inhibition in syngeneic CT26 tumor bearing wild-type mice following repeated intratumoral administration of Compound Nos. 63-18 (FIG. 2A), 63-33 (FIG. 2B), or 63-10 (FIG. 2C) as described in Example B4. Animals were dosed as described with either vehicle control (-●-), 20 μg of compound (-■-), 5 μg of compound (- -■- -), 0.5 μg compound (-·-■-·- ), or 50 μg of a TLR9 agonist positive control (-♦-). Group size=5 for controls and 8 for experimental conditions, +/−standard error of the mean.

DETAILED DESCRIPTION OF THE INVENTION

Figure 1A:
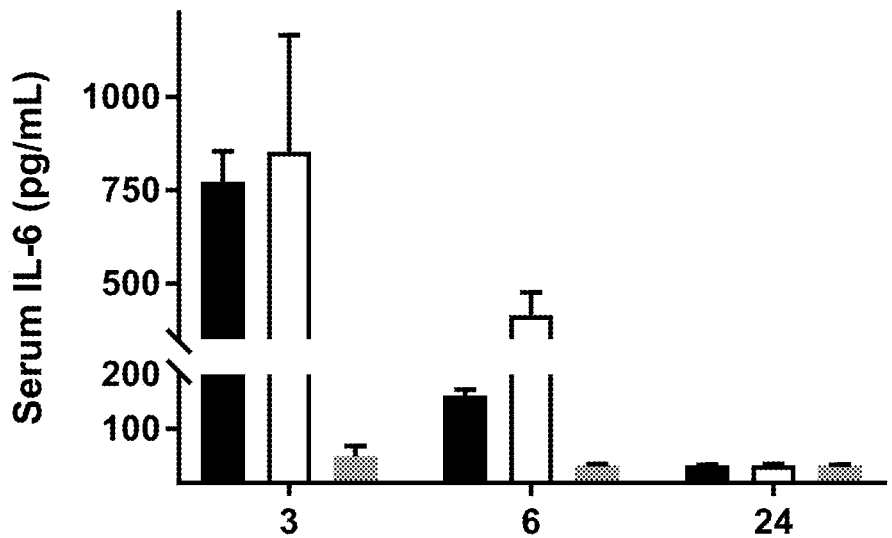
FIGS. 1A-B show the change in serum levels of IL-6 (FIG. 1A) and IL-12p40 (FIG. 1B) over time post injection following a single subcutaneous administration of Compound Nos. 63-00 (black bars), 63-17 (white bars), and 63-10 (grey bars) to wild-type mice as described in Example B3. Group size=3, +/−standard error of the mean.

The present disclosure relates to alkyl chain modified 1H-imidazo[4,5-c]quinoline derivatives that are potent TLR7/8 agonists exhibiting balanced bioactivity against both receptors, and possess physiochemical properties that enable pharmaceutical compositions which promote retention of the compound at the site of injection. The present disclosure also relates to pharmaceutical compositions comprising the alkyl chain modified 1H-imidazo[4,5-c]quinoline compounds and methods of preparation thereof, uses of the pharmaceutical compositions for stimulating an immune response, and to methods for the treatment of disease in a subject, e.g., infectious disease and cancer.

I. General Methods and Definitions

The practice of the present disclosure will employ, unless otherwise indicated, conventional techniques of organic chemistry, analytical chemistry, molecular biology, microbiology, cell biology, biochemistry, and immunology, which are within the skill of the art. Such techniques are fully described in the literature, see for example: *Fiesers' Reagents for Organic Synthesis,* $25^{th}$ edition (Ho, ed., Wiley, 2016); *Comprehensive Organic Functional Group Transformations,* 2' edition (Katritsky and Taylor, eds., Elsevier, 2004); *Comprehensive Organic Synthesis,* version 1-8 (Trost and Flemming, eds., Permagon Press, 1991); *Beilsteins Handbuch der Organischen Chemie,* 4 (Auflage, ed., Springer-Verlag, 1934); *Animal Cell Culture,* sixth edition (Freshney, Wiley-Blackwell, 2010); *Current Protocols in Cell Biology* (Bonifacino et al., ed., John Wiley & Sons, Inc., 1996, including supplements through 2014); *Current Protocols in Immunology* (Coligan et al., eds., John Wiley & Sons, Inc., 1991 including supplements through 2014); *Current Protocols in Molecular Biology* (Ausubel et al., eds., John Wiley & Sons, Inc., 1987, including supplements through 2014); *Molecular Cloning: A Laboratory Manual,* third edition (Sambrook and Russell, Cold Spring Harbor Laboratory Press, 2001); and *Molecular Cloning: A Laboratory Manual,* fourth edition (Green and Sambrook, Cold Spring Harbor Laboratory Press, 2012).

The terms "individual" and "subject" refer to mammals. "Mammals" include, but are not limited to, humans, non-human primates (e.g., monkeys), farm animals, sport animals (e.g., horses), rodents (e.g., mice and rats), and pets (e.g., dogs and cats).

The term "antigen" refers to a substance that is recognized and bound specifically by an antibody or by a T cell antigen receptor. Antigens can include peptides, polypeptides, proteins, glycoproteins, polysaccharides, complex carbohydrates, sugars, gangliosides, lipids and phospholipids; portions thereof, and combinations thereof. Antigens when present in the compositions of the present disclosure can be synthetic or isolated from nature. Antigens suitable for administration in the methods of the present disclosure include any molecule capable of eliciting an antigen-specific B cell or T cell response. Haptens are included within the scope of "antigen." A "hapten" is a low molecular weight compound that is not immunogenic by itself but is rendered immunogenic when conjugated with a generally larger immunogenic molecule.

"Polypeptide antigens" can include purified native peptides, synthetic peptides, engineered peptides, recombinant peptides, crude peptide extracts, or peptides in a partially purified or unpurified active state (such as peptides that are part of attenuated or inactivated viruses, microorganisms or cells), or fragments of such peptides. Polypeptide antigens are preferably at least six amino acid residues in length, preferably from 8 to 1800 amino acids in length, more preferably from 9 to 1000 amino acids in length, or from 10 to 100 amino acids in length. Similarly, in some embodiments, the polypeptide is about 9 to about 2000, about 9 to about 1000, about 9 to about 100, or about 9 to about 60 amino acids in length. In some embodiments, the polypeptide is at least (lower limit) 9, 10, 11, 12, 13, 14, 15, 16, 17, 18, 19, 20, 25, 30, 35, 40, 45, 50, 60, 70, 80, or 90 amino acids in length. In some embodiments, the polypeptide is at most (upper limit) 1000, 900, 800, 700, 600, 500, 400, 300, 250, 200, 150, 100, 50, or 25 amino acids in length. In some embodiments, the polypeptide antigen is from 9 to 35 amino acids in length.

As used herein, the term "immunogenic" refers to an agent (e.g., polypeptide antigen) that elicits an adaptive immune response upon administration under suitable conditions to a mammalian subject. The immune response may be a B cell (humoral) and/or T cell (cellular) mediated response.

"Adjuvant" refers to a substance which, when mixed with an immunogenic agent such as an antigen, nonspecifically enhances or potentiates an immune response to the agent in the recipient upon exposure to the mixture.

The term "agonist" is used in the broadest sense and includes any molecule that activates signaling through a receptor. For instance, a TLR7 agonist binds a toll-like receptor 7 protein and activates a TLR7-signaling pathway; a TLR8 agonist binds a toll-like receptor 8 protein and activates a TLR8-signaling pathway. A dual TLR7/8 agonist binds to both toll-like receptor 7 and toll-like receptor 8 proteins and activates both TLR7- and TLR8-signaling pathways.

"Stimulation" of a response or parameter includes eliciting and/or enhancing that response or parameter when compared to conditions that are otherwise the same except for the agent or molecule, or alternatively, as compared to another condition (e.g., increase in TLR-signaling in the presence of a TLR agonist as compared to the absence of the TLR agonist). For example, "stimulation" of an immune response means an increase in the response.

An "effective amount" of an agent disclosed herein is an amount sufficient to carry out a specifically stated purpose. An "effective amount" may be determined empirically and in a routine manner, in relation to the stated purpose. An "effective amount" or an "amount sufficient" of an agent is that amount adequate to produce a desired biological effect, such as a beneficial result, including a beneficial clinical result. The term "therapeutically effective amount" refers to an amount of an agent (e.g., TLR modulator) effective to "treat" a disease or disorder in a subject (e.g., a mammal such as a human).

The terms "treating" or "treatment" of a disease refer to executing a protocol, which may include administering one or more drugs to an individual (human or otherwise), in an effort to alleviate signs or symptoms of the disease. Thus, "treating" or "treatment" does not require complete alleviation of signs or symptoms, does not require a cure, and specifically includes protocols that have only a palliative effect on the individual. As used herein, and as well-understood in the art, "treatment" is an approach for obtaining beneficial or desired results, including clinical results. Beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival of an individual not receiving treatment.

"Palliating" a disease or disorder means that the extent and/or undesirable clinical manifestations of the disease or disorder are lessened and/or time course of progression of the disease or disorder is slowed, as compared to the expected untreated outcome. Especially in the allergy context, palliation may occur upon stimulation of a Th1 immune response against an allergen(s). Further, palliation does not necessarily occur by administration of one dose, but often occurs upon administration of a series of doses. Thus, an amount sufficient to palliate a response or disorder may be administered in one or more doses.

"Alkyl" as used herein refers to a saturated linear (i.e. unbranched) or branched univalent hydrocarbon chain or combination thereof. Particular alkyl groups are those having a designated number of carbon atoms, for example, an alkyl group having 1 to 20 carbon atoms (a "$C_1$-$C_{20}$ alkyl"), having 1 to 10 carbon atoms (a "$C_1$-$C_{10}$" alkyl), having 1 to 8 carbon atoms (a "$C_1$-$C_8$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear (i.e. unbranched) or branched univalent hydrocarbon chain or combination thereof, having at least one site of olefinic unsaturation (i.e., having at least one moiety of the formula C=C). Particular alkenyl groups are those having a designated number of carbon atoms, for example, an alkenyl group having 2 to 20 carbon atoms (a "$C_2$-$C_{20}$ alkenyl"), having 2 to 10 carbon atoms (a "$C_2$-$C_{10}$" alkenyl), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). The alkenyl group may be in "cis" or "trans" configurations, or alternatively in "E" or "Z" configurations. Examples of alkenyl groups include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs, and isomers thereof, and the like.

"Alkynyl" as used herein refers to an unsaturated linear (i.e. unbranched) or branched univalent hydrocarbon chain or combination thereof, having at least one site of acetylenic unsaturation (i.e., having at least one moiety of the formula CC). Particular alkynyl groups are those having a designated number of carbon atoms, for example, an alkynyl group having 2 to 20 carbon atoms (a "$C_2$-$C_{20}$ alkynyl"), having 2 to 10 carbon atoms (a "$C_2$-$C_{10}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl groups include, but are not limited to, groups such as ethynyl (or acetylenyl), prop-1-ynyl, prop-2-ynyl (or propargyl), but-1-ynyl, but-2-ynyl, but-3-ynyl, homologs, and isomers thereof, and the like.

"Alkylene" as used herein refers to the same residues as alkyl, but having bivalency. Particular alkylene groups are those having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene"), or 1 to 3 carbon atoms (a "$C_1$-$C_3$ alkylene"). Examples of alkylene groups include, but are not limited to, groups such as methylene ($-CH_2-$ or $=CH_2$), ethylene ($-CH_2CH_2-$ or $=CHCH_3$), propylene ($-CH_2CH_2CH_2-$ or $=CHCH_2CH_3$), butylene ($-CH_2CH_2CH_2CH_2-$ or $=CHCH_2CH_2CH_3$), and the like.

"Cycloalkyl" as used herein refers to non-aromatic, saturated, or unsaturated cyclic univalent hydrocarbon structures. Particular cycloalkyl groups are those having a designated number of annular (i.e., ring) carbon atoms, for example, a cycloalkyl group having from 3 to 12 annular carbon atoms (a "$C_3$-$C_{12}$ cycloalkyl"). A preferred cycloalkyl is a cyclic hydrocarbon having from 3 to 8 annular carbon atoms (a "$C_3$-$C_8$ cycloalkyl"), or having 3 to 6 annular carbon atoms (a "$C_3$-$C_6$ cycloalkyl"). Cycloalkyl can consist of one ring, such as cyclohexyl, or multiple rings, such as adamantyl, but excludes aryl groups. A cycloalkyl comprising more than one ring may be fused, spiro, or bridged, or combinations thereof. Examples of cycloalkyl groups include, but are not limited to, cyclopropyl, cyclobutyl, cyclopentyl, cyclohexyl, 1-cyclohexenyl, 3-cyclohexenyl, cycloheptyl, norbornyl, and the like.

"Cycloalkylene" as used herein refers to the same residues as cycloalkyl, but having bivalency. Particular cycloalkylene groups are those having 3 to 12 annular carbon atoms (a "$C_3$-$C_{12}$ cycloalkylene"), having from 3 to 8 annular carbon atoms (a "$C_3$-$C_8$ cycloalkylene"), or having 3 to 6 annular carbon atoms (a "$C_3$-$C_6$ cycloalkylene"). Examples of cycloalkylene groups include, but are not limited to, cyclopropylene, cyclobutylene, cyclopentylene, cyclohexylene, 1,2-cyclohexenylene, 1,3-cyclohexenylene, 1,4-cyclohexenylene, cycloheptyl, norbornyl, and the like.

"Hydrocarbyl" as used herein refers to and includes a univalent group formed by removing a hydrogen atom from a non-aromatic hydrocarbon, which may be fully saturated mono- or polyunsaturated, having the number of carbon atoms designated (i.e., $C_1$-$C_{20}$ means one to twenty carbon atoms). A hydrocarbyl group may contain one or more linear, branched, or cyclic moieties, or combinations thereof. Alkyl, alkenyl, alkynyl, and cycloalkyl groups are particular subsets of hydrocarbyl groups. A hydrocarbyl group may also contain an alkyl, alkenyl or alkynyl group further substituted by one or more cycloalkyl groups; and/or a cycloalkyl group further substituted by one of more alkyl, alkenyl, and/or alkynyl groups. A hydrocarbyl group may be substituted, at one or more positions, by one or more halogen atoms, such as chlorine or fluorine. Examples of hydrocarbyl groups include, but are not limited to, groups such as the following:

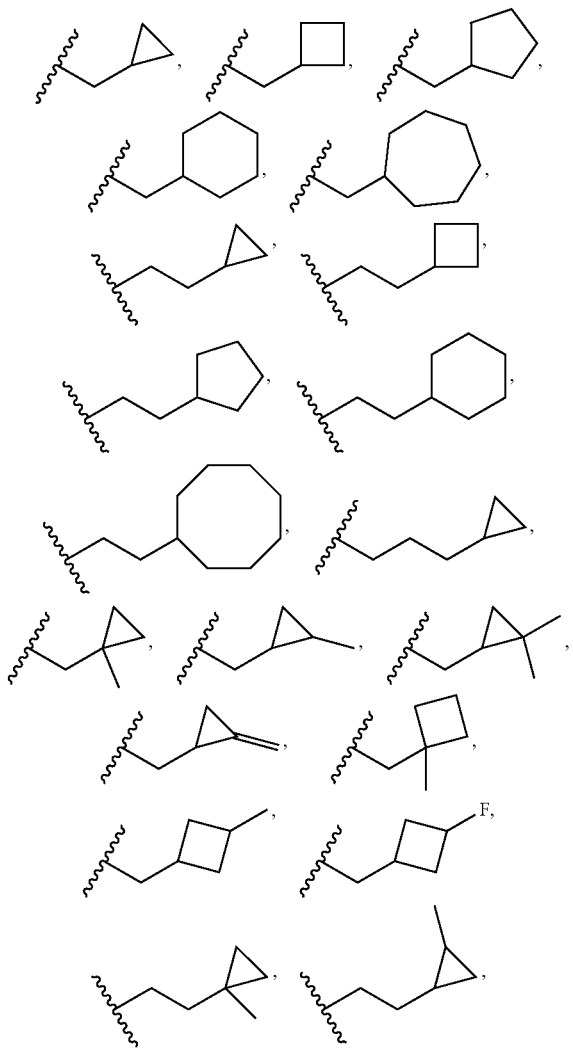

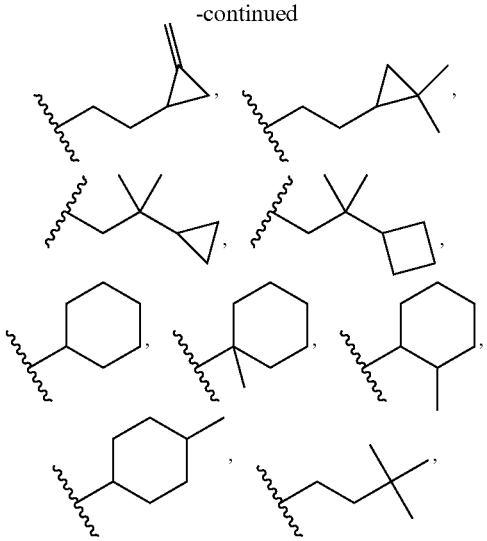

and the like.

"Aryl" as used herein refers to an unsaturated aromatic carbocyclic group having a single ring (e.g., phenyl) or multiple condensed rings (e.g., naphthyl or anthryl), where one or more of the condensed rings may not be aromatic. Particular aryl groups are those having from 6 to 14 annular (i.e., ring) carbon atoms (a "$C_6$-$C_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position. Examples of aryl include, but are not limited to, groups such as phenyl, naphthyl, 1-naphthyl, 2-naphthyl, and the like.

"Arylene" as used herein refers to the same residues as aryl, but having bivalency. Particular arylene groups are those having from 6 to 14 annular carbon atoms (a "$C_6$-$C_{14}$ arylene"). Examples of arylene include, but are not limited to, groups such as phenylene, o-phenylene (i.e., 1,2-phenylene), m-phenylene (i.e., 1,3-phenylene), p-phenylene (i.e., 1,4-phenylene), naphthylene, 1,2-naphthylene, 1,2-naphthylene, 1,4-naphthylene, and the like.

"Halo" or "halogen" refers to elements of the Group 17 series having atomic number 9 to 85. Preferred halo groups include fluoro, chloro, bromo, and iodo. Where a residue is substituted with more than one halogen, it may be referred to by using a prefix corresponding to the number of halogen moieties attached. For example, dihaloaryl, dihaloalkyl, and trihaloaryl etc., refer to aryl and alkyl substituted with two ("di") or three ("tri") halo groups, which may be but are not necessarily the same halo; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Amino" refers to the group —$NH_2$.

"Substituted amino" refers to the group —NR'R" where R' and R" are independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one of R' and R" is not hydrogen.

"Optionally substituted" unless otherwise specified means that a group may be unsubstituted or substituted by one or more (e.g., 1, 2, 3, 4, or 5) of the substituents listed for that group in which the substituents may be the same or different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, or 1 to 5 substituents.

"Organic modifier" unless otherwise specified means one of a group of solvents typically used to solubilize organic chemical compounds. This group can include, but is not limited to acetic acid, acetone, anisole, 1-butanol, 2-butanol, butyl acetate, tert-butyl methyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylenthylketone, methylisobutylketone, 2-methyl-1-propanol, pentane, 1-pentanol, 1-propanol, 2-propanol (isopropanol), propyl acetate, and combinations thereof.

In addition to the disclosure herein, the term "substituted," when used to modify a specified group or radical, can also mean that one or more hydrogen atoms of the specified group or radical are each, independently of one another, replaced with the same or different substituent groups as defined herein. In some embodiments, a group that is substituted has 1, 2, 3, or 4 substituents, 1, 2, or 3 substituents, 1 or 2 substituents, or 1 substituent.

Unless a specific isotope of an element is indicated in a formula, the invention includes all isotopologues of the compounds disclosed herein, such as, for example, deuterated derivatives of the compounds (where H can be $^2$H, i.e., D). Isotopologues can have isotopic replacements at any or at all locations in a structure, or can have atoms present in natural abundance at any or all locations in a structure.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

It is understood that aspects and embodiments described herein as "comprising" include "consisting of" and "consisting essentially of" embodiments.

As used herein and in the appended claims, the singular forms "a," "an", and "the" include plural referents unless otherwise indicated or clear from context.

Unless clearly indicated otherwise, the term "about" is used to indicate that a value includes the standard deviation or error for the device or method being employed to determine the value. Reference to "about" a value or parameter herein includes (and describes) embodiments that are directed to that value or parameter per se. For example, description referring to "about X" includes description of "X."

II. Compounds

In one aspect, provided is a compound of formula (J):

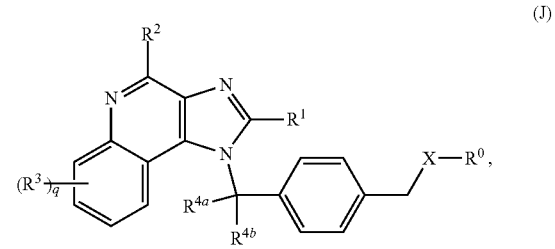

or a salt thereof, wherein:
R$^0$ is C$_4$-C$_{21}$ hydrocarbyl optionally substituted by 1 to 4 halogen atoms;
X is —NH— or —NH(C=O)—;
R$^1$ is C$_3$-C$_6$ alkyl, —(CH$_2$)$_p$OR$^{1a}$, —(CH$_2$)$_p$NHR$^{1b}$, or —(CH$_2$)$_p$R$^{1c}$; where R$^{1a}$ and R$^{1b}$ are independently C$_1$-C$_3$ alkyl; R$^{1c}$ is C$_3$-C$_4$ cycloalkyl; and p is 1 or 2;
R$^2$ is NHR$^{2a}$; where R$^{2a}$ is H, OH, NH$_2$, or methyl;
each R$^3$ is independently halogen, C$_1$-C$_8$ alkyl, —(C$_1$-C$_7$ alkylene)-NH$_2$, or —CH$_2$-phenylene-CH$_2$NH$_2$;
q is 0, 1, 2, 3, or 4; and
R$^{4a}$ and R$^{4b}$ are independently H or C$_1$-C$_8$ alkyl,
provided that the compound is other than 2-butyl-1-(4-((hexadecylamino)methyl)benzyl)-1H-imidazo[4,5-c] quinolin-4-amine (Compound No. 63-32); N-(4-((4-amino-2-butyl-1H-imidazo[4,5-c]quinolin-1-yl) methyl)benzyl)palmitamide (Compound No. 63-31); or N-(4-((4-amino-2-butyl-1H-imidazo[4,5-c]quinolin-1-yl)methyl)benzyl)pent-4-ynamide (Compound No. 63-37).

In some embodiments, R$^0$ is C$_4$-C$_{21}$ hydrocarbyl. In some embodiments, R$^0$ is C$_4$-C$_{14}$ hydrocarbyl. In some embodiments, R$^0$ is C$_5$-C$_{10}$ hydrocarbyl. In some embodiments, R$^0$ is C$_{10}$-C$_{14}$ hydrocarbyl. In some embodiments, R$^0$ is C$_5$-C$_7$ hydrocarbyl.

In some embodiments, X is —NH(C=O)—. In other embodiments, X is —NH—.

In some embodiments, R$^0$ is branched C$_4$-C$_{14}$ alkyl or —(CH$_2$)$_m$R$^A$; m is 0, 1, 2, or 3; and R$^A$ is C$_3$-C$_8$ cycloalkyl optionally substituted by 1 to 4 groups independently selected from the group consisting of C$_1$-C$_4$ alkyl and C$_1$-C$_4$ alkylene.

In some embodiments, R$^0$ is branched C$_4$-C$_{14}$ alkyl. In some embodiments, R$^0$ is branched C$_5$-C$_{10}$ alkyl. In some embodiments, R$^0$ is branched C$_{10}$-C$_{14}$ alkyl. In some embodiments, R$^0$ is branched C$_5$-C$_7$ alkyl.

In some embodiments, R$^0$ is —(CH$_2$)$_m$R$^A$. In one variation, m is 1 or 2, and R$^A$ is cyclopropyl, cyclobutyl, or cyclopentyl. In another variation, m is 0, and R$^A$ is cyclobutyl, cyclopentyl, or cyclohexyl.

In some embodiments, R$^A$ is C$_3$-C$_8$ cycloalkyl.

In some embodiments, $R^A$ is $C_3$-$C_6$ cycloalkyl optionally substituted by 1 to 3 groups independently selected from the group consisting of methyl and methylene. In one variation, m is 1 or 2.

In some embodiments, $R^A$ is cyclopropyl optionally substituted by 1 to 3 groups independently selected from the group consisting of methyl and methylene, and m is 1 or 2.

In some embodiments, m is 0 or 1, and $R^A$ is cyclohexyl optionally substituted by 1 to 3 groups independently selected from the group consisting of methyl and methylene.

In some embodiments, $R^A$ is $C_3$-$C_6$ cycloalkyl optionally substituted by 1 to 4 halogen atoms. In some embodiments, $R^A$ is $C_3$-$C_6$ cycloalkyl optionally substituted by 1 to 3 chlorine or fluorine atoms. In some embodiments, $R^A$ is $C_3$-$C_6$ cycloalkyl optionally substituted by 1 to 2 chlorine or fluorine atoms. In some embodiments, $R^A$ is cyclobutyl optionally substituted by 1 to 2 fluorine atoms. In one variation, m is 1.

In some embodiments, $R^O$ is $-(CH_2)_z(C(CH_3)_2)R^A$. In one variation, z is 1 or 2, and $R^A$ is cyclopropyl, cyclobutyl, or cyclopentyl. In one variation, z is 1, and $R^A$ is cyclopropyl, cyclobutyl, or cyclopentyl.

In some embodiments, $R^O$ is selected from the group consisting of:

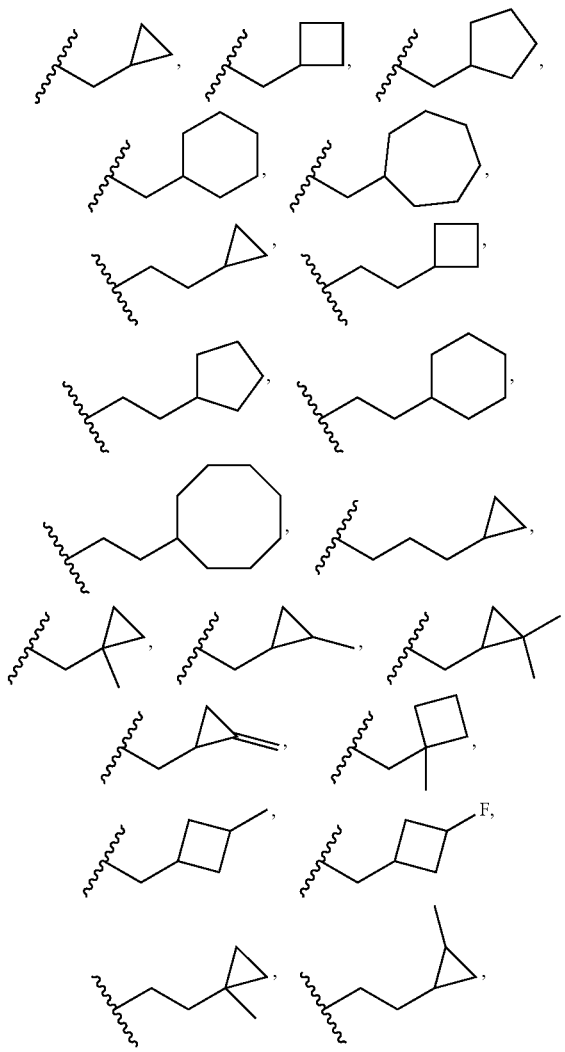

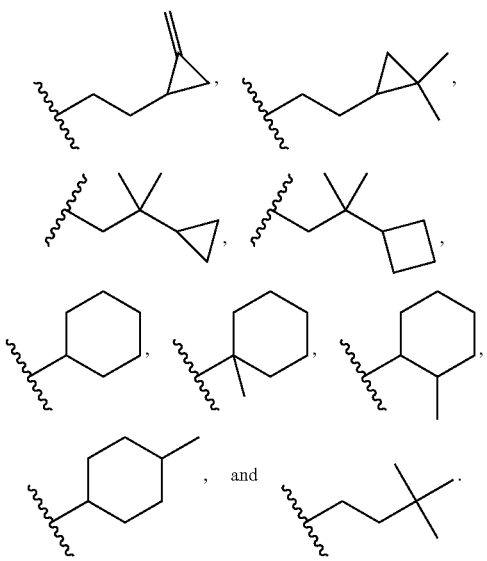

In some embodiments, $R^O$ is selected from the group consisting of:

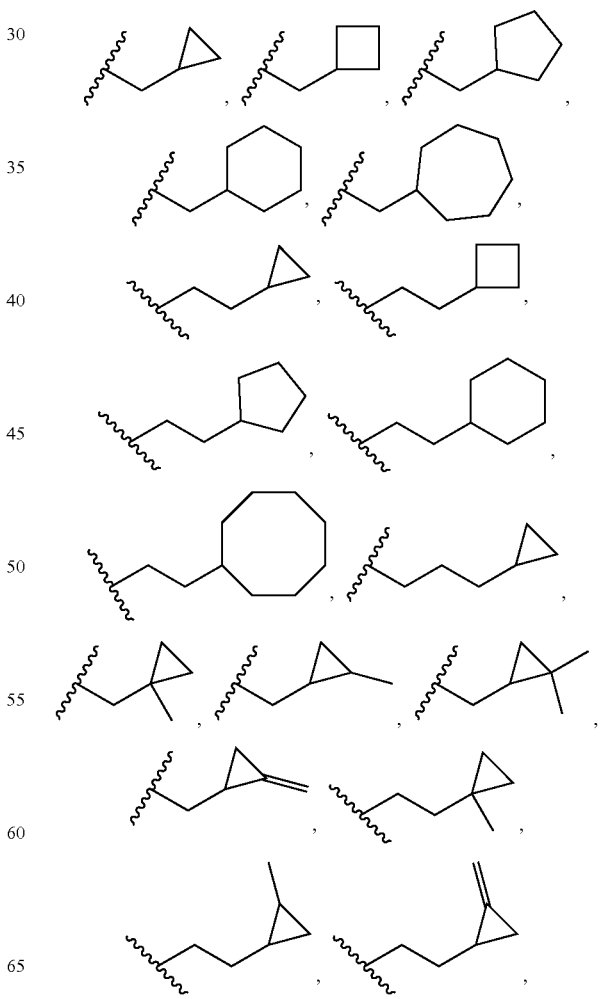

-continued

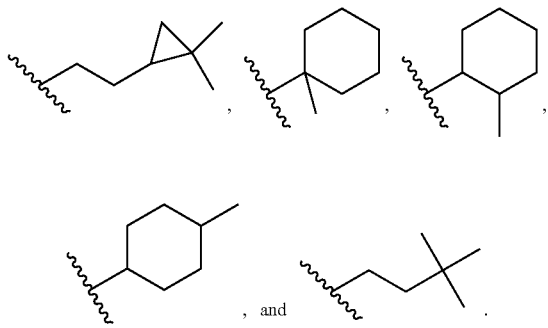

In some embodiments, R⁰ is selected from the group consisting of:

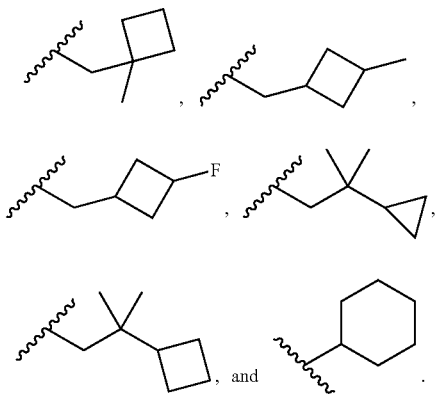

In some embodiments, X is —NH—, R⁰ is —(CH$_2$)$_m$R$^A$, m is 2, and R$^A$ is cyclopropyl, cyclobutyl, or cyclopentyl.

In some embodiments, X is —NH—, R⁰ is —(CH$_2$)$_z$(C(CH$_3$)$_2$)R$^A$, z is 1, and R$^A$ is cyclopropyl, cyclobutyl, or cyclopentyl.

In some embodiments, X is —NH—, R⁰ is —(CH$_2$)$_m$R$^A$, m is 0, and R$^A$ is cyclobutyl, cyclopentyl, or cyclohexyl.

In some embodiments, X is —NH(C=O)—, R⁰ is —(CH$_2$)$_m$R$^A$, m is 1, and R$^A$ is cyclopropyl, cyclobutyl, or cyclopentyl.

In some embodiments, R$^1$ is C$_3$-C$_6$ alkyl (e.g., n-butyl). In some embodiments, R$^1$ is propyl, butyl, pentyl, or hexyl. In some preferred embodiments, R$^1$ is n-butyl. In some embodiments, R$^1$ is n-pentyl. In some embodiments, R$^1$ is —(CH$_2$)$_p$OR$^{1a}$ (e.g., CH$_2$OCH$_2$CH$_3$). In some embodiments, R$^1$ is —(CH$_2$)$_p$NHR$^{1b}$ (e.g., CH$_2$NHCH$_2$CH$_3$). In some embodiments, R$^1$ is —(CH$_2$)$_p$R$^{1c}$. In one variation, R$^{1c}$ is cyclopropyl.

In some embodiments, R$^2$ is NHR$^{2a}$, where R$^{2a}$ is H, OH, NH$_2$, or methyl. In some embodiments, R$^2$ is NH$_2$. In some embodiments, R$^2$ is NHOH, NHNH$_2$, or NHCH$_3$.

In some embodiments, R$^{4a}$ and R$^{4b}$ are independently H or C$_1$-C$_8$ alkyl. In some embodiments, each R$^{4a}$ and R$^{4b}$ is H.

In some embodiments, the phenyl moiety of the 1H-imidazo[4,5-c]quinoline core is unsubstituted (i.e., q is 0). In some embodiments, the phenyl moiety of the 1H-imidazo[4,5-c]quinoline core is substituted by 1, 2, 3, or 4 substituents independently selected from the group consisting of halogen, C$_1$-C$_8$ alkyl, —(C$_1$-C$_7$ alkylene)-NH$_2$, and —CH$_2$-phenylene-CH$_2$NH$_2$. In some embodiments, q is 1, and R$^3$ is C$_1$-C$_8$ alkyl.

It is intended and understood that where present each and every variation of X and R⁰ described for formula (J) may be combined with each and every variation of R$^1$, p, R$^2$, q, R$^3$, R$^{4a}$ and R$^{4b}$ described for formula (J) the same as if each and every combination is specifically and individually described.

In some embodiments, the compound of formula (J) is of formula (J-1):

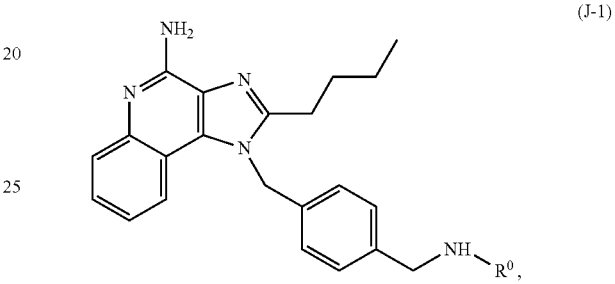

(J-1)

or a salt thereof, wherein R⁰ is C$_4$-C$_{21}$ hydrocarbyl. In some embodiments, R⁰ is —(CH$_2$)$_m$R$^A$. In one variation, m is 1 or 2, and R$^A$ is cyclopropyl, cyclobutyl, cyclopentyl, or cyclohexyl. In one variation, m is 2, and R$^A$ is cyclopropyl, cyclobutyl, or cyclopentyl. In another variation, m is 0, and R$^A$ is cyclobutyl, cyclopentyl, or cyclohexyl. In some embodiments, R⁰ is —(CH$_2$)$_z$(C(CH$_3$)$_2$)R$^A$. In one variation, z is 1, and R$^A$ is cyclopropyl, cyclobutyl, or cyclopentyl. In some embodiments, R$^A$ is optionally substituted by 1-4 groups independently selected from the group consisting of methyl, methylene, and halogen.

In some embodiments, the compound of formula (J) is of formula (J-2):

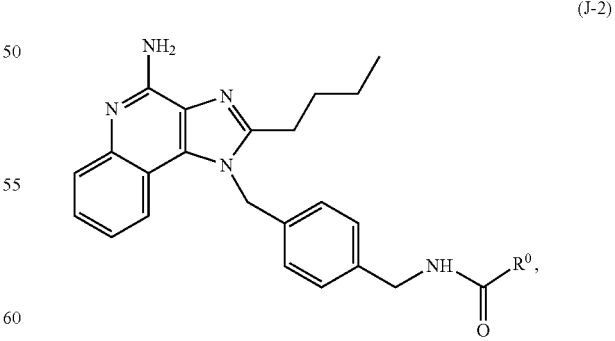

(J-2)

or a salt thereof, wherein R⁰ is C$_4$-C$_{21}$ hydrocarbyl, provided that the compound is other than N-(4-((4-amino-2-butyl-1H-imidazo[4,5-c]quinolin-1-yl)methyl)benzyl)pent-4-ynamide (Compound No. 63-37). In some embodiments, R⁰ is —(CH$_2$)$_m$R$^A$. In one variation, m is 1 or 2, and R$^A$ is cyclopropyl, cyclobutyl, cyclopentyl, or cyclohexyl. In one variation, m is 1 and R$^A$ is cyclopropyl.

In another aspect, provided is a compound of formula (K):

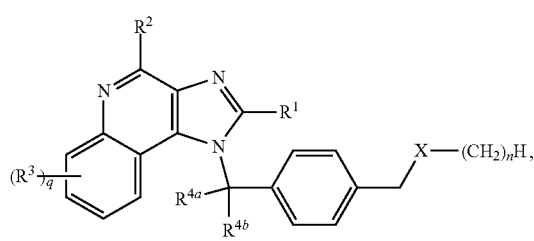

or a salt thereof, wherein:
n is an integer from 4 to 21;
X is —NH— or —NH(C═O)—;
R$^1$ is C$_3$-C$_6$ alkyl, —(CH$_2$)$_p$OR$^{1a}$, —(CH$_2$)$_p$NHR$^{1b}$ or —(CH$_2$)$_p$R$^{1c}$; where R$^{1a}$ and R$^{1b}$ are independently C$_1$-C$_3$ alkyl; R$^{1c}$ is C$_3$-C$_4$ cycloalkyl; and p is 1 or 2;
R$^2$ is NHR$^{2a}$; where R$^{2a}$ is H, OH, NH$_2$ or methyl;
each R$^3$ is independently halogen, C$_1$-C$_8$ alkyl, —(C$_1$-C$_7$ alkylene)-NH$_2$, or —CH$_2$-phenylene-CH$_2$NH$_2$;
q is 0, 1, 2, 3, or 4; and
R$^{4a}$ and R$^{4b}$ are independently H or C$_1$-C$_8$ alkyl,
provided that the compound is other than 2-butyl-1-(4-((hexadecylamino)methyl)benzyl)-1H-imidazo[4,5-c]quinolin-4-amine (Compound No. 63-32) or N-(4-((4-amino-2-butyl-1H-imidazo[4,5-c]quinolin-1-yl)methyl)benzyl)palmitamide (Compound No. 63-31).

In some embodiments, X is —NH—. In some embodiments, X is —NH(C═O)—.

In some embodiments, X is —NH— and n is an integer from 4 to 15. In some preferred embodiments, X is —NH— and n is an integer from 4 to 12. In some preferred embodiments, X is —NH— and n is 4, 5, 6, or 7. In some embodiments, n is 8, 9, 10, 11, 12, 13, 14, or 15.

In some embodiments, X is —NH(C═O)— and n is an integer from 4 to 14. In some preferred embodiments, X is —NH(C═O)— and n is 11, 12, 13, or 14. In some embodiments, n is 4, 5, 6, 7, 8, 9, or 10.

In some embodiments, R$^1$ is C$_3$-C$_6$ alkyl. In some embodiments, R$^1$ is propyl, butyl, pentyl or hexyl. In some preferred embodiments, R$^1$ is n-butyl. In some embodiments, R$^1$ is n-pentyl.

In some embodiments, R$^1$ is —(CH$_2$)$_p$OR$^{1a}$, where p is 1 or 2 and R$^{1a}$ is C$_1$-C$_3$ alkyl. In some embodiments, R$^1$ is —CH$_2$OCH$_2$CH$_3$.

In some embodiments, R$^1$ is —(CH$_2$)$_p$NHR$^{1b}$ where R$^{1b}$ is C$_1$-C$_3$ alkyl. In some embodiments, R$^1$ is —CH$_2$NHCH$_2$CH$_3$.

In some embodiments, R$^1$ is —(CH$_2$)$_p$R$^{1c}$ where p is 1 or 2 and R$^{1c}$ is cyclopropyl or cyclobutyl. In some embodiments, R$^1$ is —CH$_2$-cyclopropyl or —CH$_2$CH$_2$-cyclopropyl.

In some embodiments, R$^2$ is NHR$^{2a}$, where R$^{2a}$ is H, OH, NH$_2$, or methyl. In some preferred embodiments, R$^2$ is NH$_2$. In some embodiments, R$^2$ is NHOH, NHNH$_2$, or NHCH$_3$.

In some embodiments, the phenyl moiety of the 1H-imidazo[4,5-c]quinoline core is unsubstituted (i.e., q is 0). In some embodiments, the phenyl moiety of the 1H-imidazo[4,5-c]quinoline core is substituted by 1, 2, 3, or 4 substituents independently selected from the group consisting of halogen, C$_1$-C$_8$ alkyl, —(C$_1$-C$_7$ alkylene)-NH$_2$, and —CH$_2$-phenylene-CH$_2$NH$_2$. In some embodiments, q is 1 and R$^3$ is C$_1$-C$_8$ alkyl.

In some embodiments, R$^{4a}$ and R$^{4b}$ are independently H or C$_1$-C$_8$ alkyl. In some preferred embodiments, each R$^{4a}$ and R$^{4b}$ is H.

It is intended and understood that each and every variation of X and n described for formula (K) may be combined with each and every variation of R$^1$, R$^2$, q, R$^3$, R$^{4a}$, and R$^{4b}$, where present, described for formula (K) the same as if each and every combination is specifically and individually described. For example, in some embodiments, R$^1$ is C$_3$-C$_6$ alkyl (e.g., n-butyl), R$^2$ is NH$_2$, q is 0, X is —NH—, and n is 4, 5, 6, or 7. In some embodiments, R$^1$ is C$_3$-C$_6$ alkyl (e.g., n-butyl), R$^2$ is NH$_2$, q is 0, X is —NH(C═O)—, and n is 11, 12, 13, or 14.

In some embodiments, the compound of formula (K) is of formula (K-1):

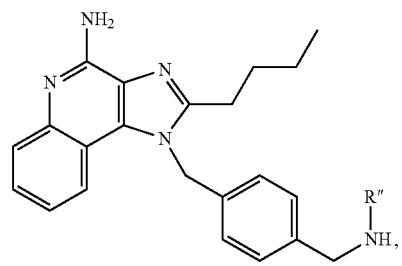

or a salt thereof, wherein R" is linear C$_4$-C$_{21}$ alkyl, provided that the compound is other than 2-butyl-1-(4-((hexadecylamino)methyl)benzyl)-1H-imidazo[4,5-c]quinolin-4-amine (Compound No. 63-32). In some embodiments, R" is linear C$_4$-C$_{15}$ alkyl. In some embodiments, R" is linear C$_4$-C$_7$ alkyl. In some embodiments, R" is linear C$_8$-C$_{15}$ alkyl. In some embodiments, R" is linear C$_{17}$-C$_{21}$ alkyl.

In some embodiments, the compound of formula (K) is of formula (K-2):

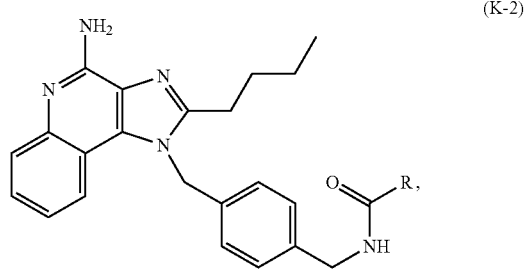

or a salt thereof, wherein R is linear C$_4$-C$_{21}$ alkyl, provided that the compound is other than N-(4-((4-amino-2-butyl-1H-imidazo[4,5-c]quinolin-1-yl)methyl)benzyl)palmitamide (Compound No. 63-31). In some embodiments, R is linear C$_4$-C$_{14}$ alkyl. In some embodiments, R is linear C$_{11}$-C$_{14}$ alkyl. In some embodiments, R is linear C$_4$-C$_{10}$ alkyl. In some embodiments, R is linear C$_{16}$-C$_{21}$ alkyl.

Representative compounds of the invention are listed in Table 1.

TABLE 1
| Compound No. | Formula | Name |
|---|---|---|
| 63-01 | 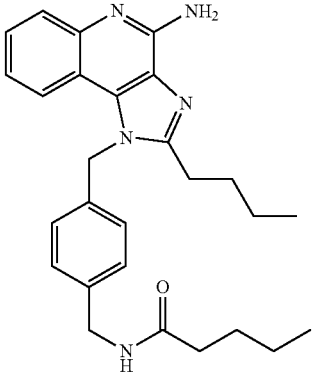 [SMILES: CCCCC(=O)NCc1ccc(Cn2c(CCCC)nc3c(N)nc4ccccc4c32)cc1] | N-(4-((4-amino-2-butyl-1H-imidazo[4,5-c]quinolin-1-yl)methyl)benzyl)pentanamide |
| 63-02 | 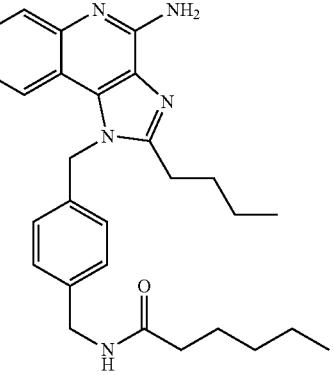 | N-(4-((4-amino-2-butyl-1H-imidazo[4,5-c]quinolin-1-yl)methyl)benzyl)hexanamide |
| 63-03 | 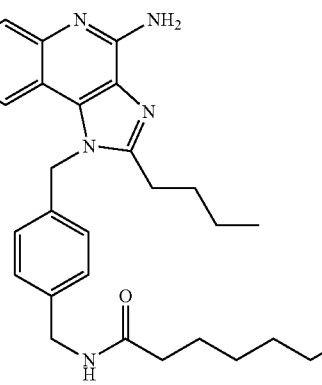 | N-(4-((4-amino-2-butyl-1H-imidazo[4,5-c]quinolin-1-yl)methyl)benzyl)heptanamide |
| 63-04 | 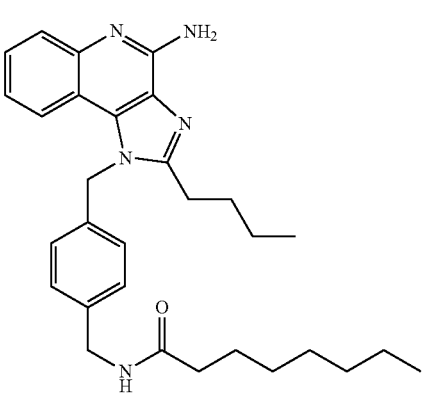 [SMILES: CCCCCCCC(=O)NCc1ccc(Cn2c(CCCC)nc3c(N)nc4ccccc4c32)cc1] | N-(4-((4-amino-2-butyl-1H-imidazo[4,5-c]quinolin-1-yl)methyl)benzyl)octanamide |

TABLE 1-continued
| Compound No. | Formula | Name |
|---|---|---|
| 63-05 | 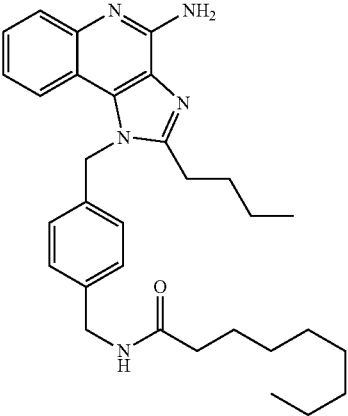 [SMILES: CCCCCCCCC(=O)NCc1ccc(Cn2c(CCCC)nc3c(N)nc4ccccc4c32)cc1] | N-(4-((4-amino-2-butyl-1H-imidazo[4,5-c]quinolin-1-yl)methyl)benzyl)nonanamide |
| 63-06 | 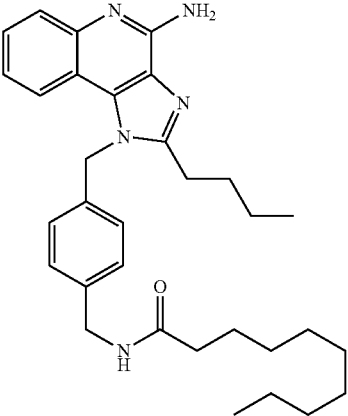 [SMILES: CCCCCCCCCC(=O)NCc1ccc(Cn2c(CCCC)nc3c(N)nc4ccccc4c32)cc1] | N-(4-((4-amino-2-butyl-1H-imidazo[4,5-c]quinolin-1-yl)methyl)benzyl)decanamide |
| 63-07 | 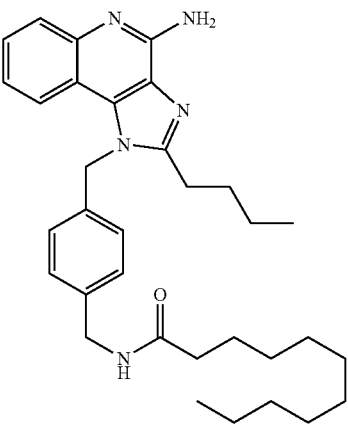 [SMILES: CCCCCCCCCCC(=O)NCc1ccc(Cn2c(CCCC)nc3c(N)nc4ccccc4c32)cc1] | N-(4-((4-amino-2-butyl-1H-imidazo[4,5-c]quinolin-1-yl)methyl)benzyl)undecanamide |

TABLE 1-continued
| Compound No. | Formula | Name |
|---|---|---|
| 63-08 | 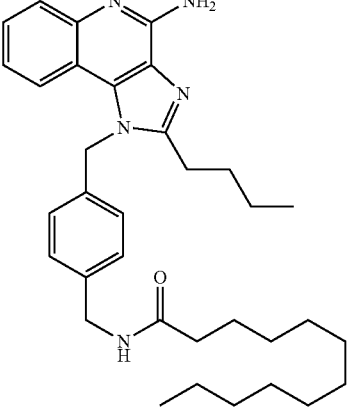 | N-(4-((4-amino-2-butyl-1H-imidazo[4,5-c]quinolin-1-yl)methyl)benzyl)dodecanamide |
| 63-09 | 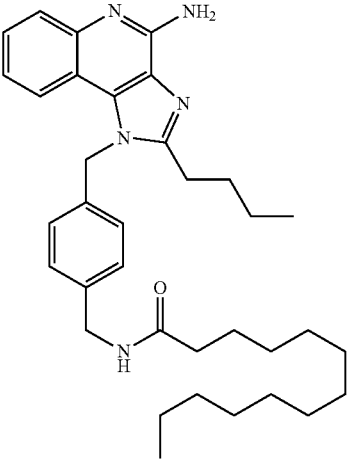 [SMILES: CCCCCCCCCCCCC(=O)NCc1ccc(Cn2c(CCCC)nc3c(N)nc4ccccc4c32)cc1] | N-(4-((4-amino-2-butyl-1H-imidazo[4,5-c]quinolin-1-yl)methyl)benzyl)tridecanamide |
| 63-10 | 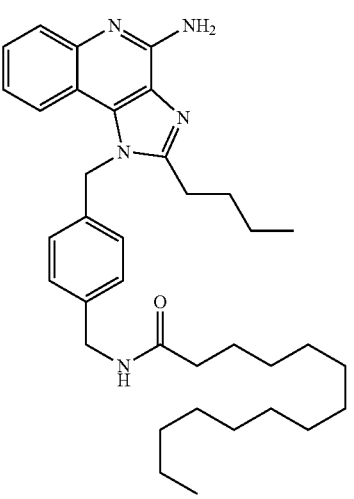 [SMILES: CCCCCCCCCCCCCC(=O)NCc1ccc(Cn2c(CCCC)nc3c(N)nc4ccccc4c32)cc1] | N-(4-((4-amino-2-butyl-1H-imidazo[4,5-c]quinolin-1-yl)methyl)benzyl)tetradecanamide |

TABLE 1-continued
| Compound No. | Formula | Name |
|---|---|---|
| 63-11 | 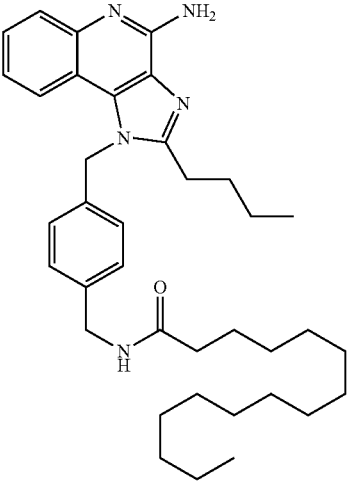 [SMILES: CCCCCCCCCCCCCCC(=O)NCc1ccc(Cn2c(CCCC)nc3c(N)nc4ccccc4c32)cc1] | N-(4-((4-amino-2-butyl-1H-imidazo[4,5-c]quinolin-1-yl)methyl)benzyl)pentadecanamide |
| 63-12 | 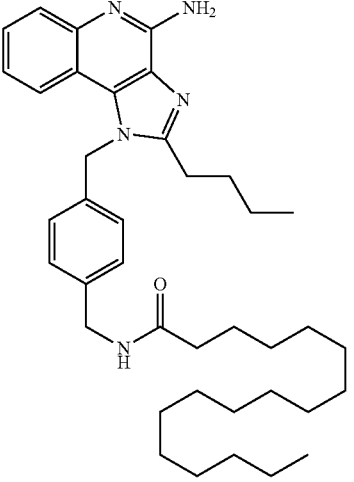 [SMILES: CCCCCCCCCCCCCCCCC(=O)NCc1ccc(Cn2c(CCCC)nc3c(N)nc4ccccc4c32)cc1] | N-(4-((4-amino-2-butyl-1H-imidazo[4,5-c]quinolin-1-yl)methyl)benzyl)heptadecanamide |
| 63-13 | 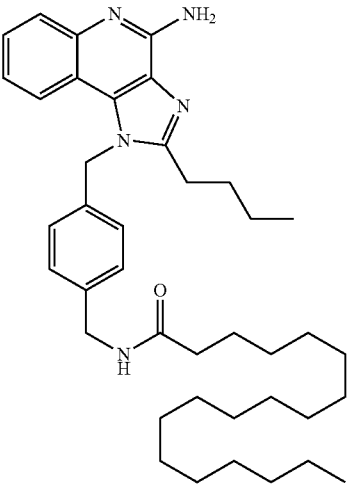 [SMILES: CCCCCCCCCCCCCCCCCC(=O)NCc1ccc(Cn2c(CCCC)nc3c(N)nc4ccccc4c32)cc1] | N-(4-((4-amino-2-butyl-1H-imidazo[4,5-c]quinolin-1-yl)methyl)benzyl)stearamide |

TABLE 1-continued
| Compound No. | Formula | Name |
|---|---|---|
| 63-14 | 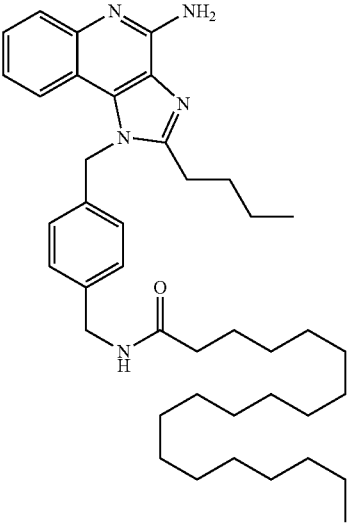 [SMILES: CCCCCCCCCCCCCCCCCCC(=O)NCc1ccc(Cn2c(CCCC)nc3c(N)nc4ccccc4c32)cc1] | N-(4-((4-amino-2-butyl-1H-imidazo[4,5-c]quinolin-1-yl)methyl)benzyl)nonadecanamide |
| 63-15 | 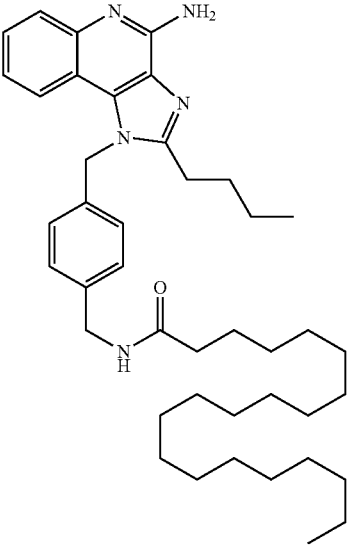 [SMILES: CCCCCCCCCCCCCCCCCCCC(=O)NCc1ccc(Cn2c(CCCC)nc3c(N)nc4ccccc4c32)cc1] | N-(4-((4-amino-2-butyl-1H-imidazo[4,5-c]quinolin-1-yl)methyl)benzyl)icosanamide |
| 63-16 | 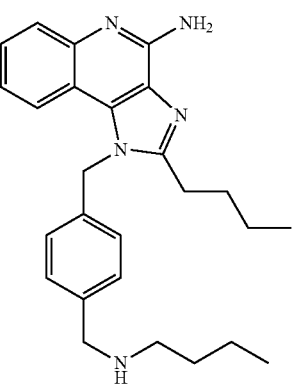 [SMILES: CCCCNCc1ccc(Cn2c(CCCC)nc3c(N)nc4ccccc4c32)cc1] | 2-butyl-1-(4-((butylamino)methyl)benzyl)-1H-imidazo[4,5-c]quinolin-4-amine |

TABLE 1-continued

| Compound No. | Formula | Name |
|---|---|---|
| 63-17 | | 2-butyl-1-(4-((pentylamino)methyl)benzyl)-1H-imidazo[4,5-c]quinolin-4-amine |
| 63-18 | | 2-butyl-1-(4-((hexylamino)methyl)benzyl)-1H-imidazo[4,5-c]quinolin-4-amine |
| 63-19 | | 2-butyl-1-(4-((heptylamino)methyl)benzyl)-1H-imidazo[4,5-c]quinolin-4-amine |
| 63-20 | | 2-butyl-1-(4-((octylamino)methyl)benzyl)-1H-imidazo[4,5-c]quinolin-4-amine |

TABLE 1-continued

| Compound No. | Formula | Name |
|---|---|---|
| 63-21 | | 2-butyl-1-(4-((nonylamino)methyl)benzyl)-1H-imidazo[4,5-c]quinolin-4-amine |
| 63-22 | | 2-butyl-1-(4-((decylamino)methyl)benzyl)-1H-imidazo[4,5-c]quinolin-4-amine |
| 63-23 | | 2-butyl-1-(4-((undecylamino)methyl)benzyl)-1H-imidazo[4,5-c]quinolin-4-amine |

TABLE 1-continued
| Compound No. | Formula | Name |
|---|---|---|
| 63-24 | 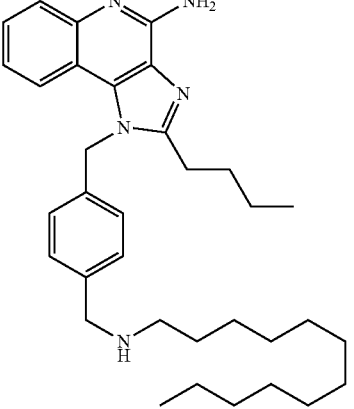 | 2-butyl-1-(4-((dodecylamino)methyl)benzyl)-1H-imidazo[4,5-c]quinolin-4-amine |
| 63-25 | 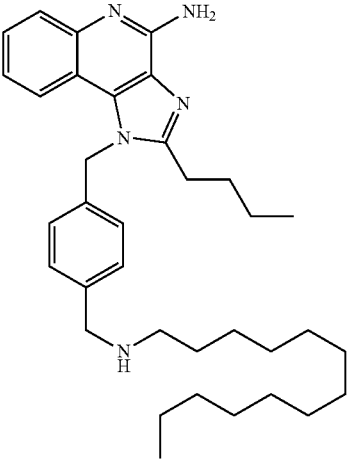 [SMILES: CCCCCCCCCCCCCNCc1ccc(Cn2c(CCCC)nc3c(N)nc4ccccc4c32)cc1] | 2-butyl-1-(4-((tridecylamino)methyl)benzyl)-1H-imidazo[4,5-c]quinolin-4-amine |
| 63-26 | 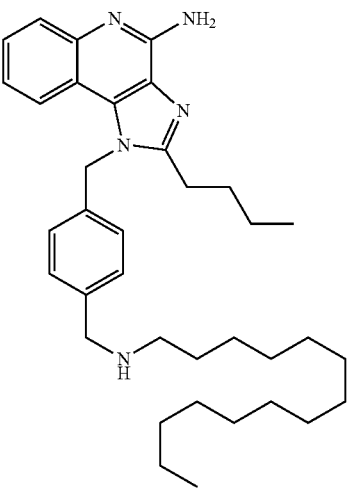 [SMILES: CCCCCCCCCCCCCCNCc1ccc(Cn2c(CCCC)nc3c(N)nc4ccccc4c32)cc1] | 2-butyl-1-(4-((tetradecylamino)methyl)benzyl)-1H-imidazo[4,5-c]quinolin-4-amine |

TABLE 1-continued
| Compound No. | Formula | Name |
|---|---|---|
| 63-27 | 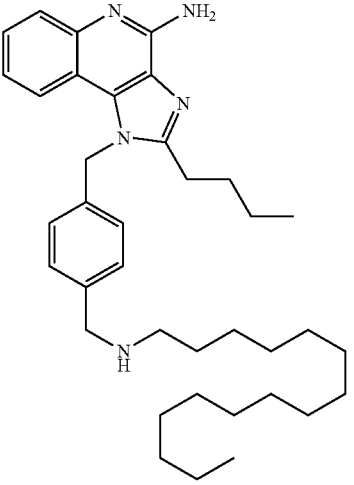 [SMILES: CCCCCCCCCCCCCCCNCc1ccc(Cn2c(CCCC)nc3c(N)nc4ccccc4c32)cc1] | 2-butyl-1-(4-((pentadecylamino)methyl)benzyl)-1H-imidazo[4,5-c]quinolin-4-amine |
| 63-28 | 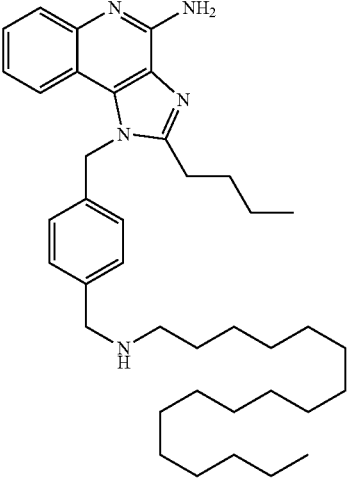 [SMILES: CCCCCCCCCCCCCCCCCNCc1ccc(Cn2c(CCCC)nc3c(N)nc4ccccc4c32)cc1] | 2-butyl-1-(4-((heptadecylamino)methyl)benzyl)-1H-imidazo[4,5-c]quinolin-4-amine |
| 63-29 | 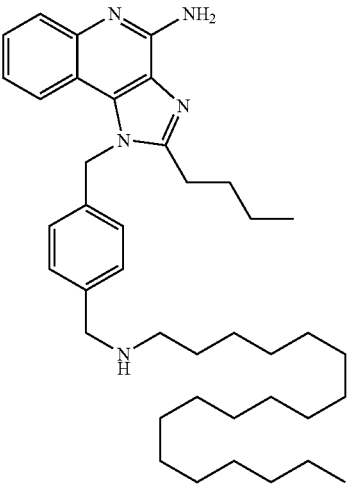 [SMILES: CCCCCCCCCCCCCCCCCCNCc1ccc(Cn2c(CCCC)nc3c(N)nc4ccccc4c32)cc1] | 2-butyl-1-(4-((octadecylamino)methyl)benzyl)-1H-imidazo[4,5-c]quinolin-4-amine |

TABLE 1-continued
| Compound No. | Formula | Name |
|---|---|---|
| 63-30 | 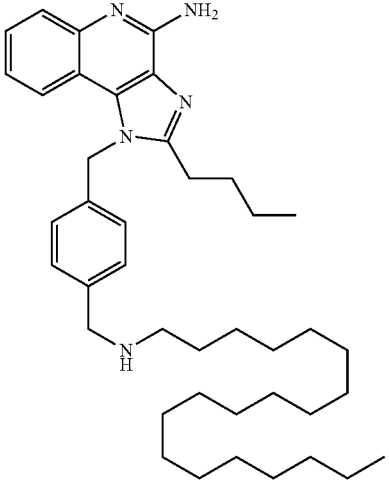 [SMILES: CCCCCCCCCCCCCCCCCCCNCc1ccc(Cn2c(CCCC)nc3c(N)nc4ccccc4c32)cc1] | 2-butyl-1-(4-((nonadecylamino)methyl)benzyl)-1H-imidazo[4,5-c]quinolin-4-amine |
| 63-33 | 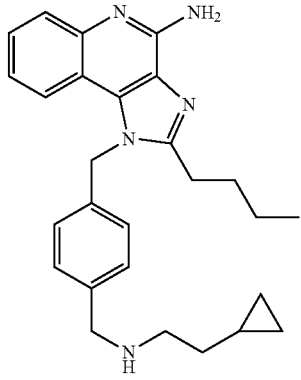 [SMILES: CCCCc1nc2c(N)nc3ccccc3c2n1Cc1ccc(CNCCC2CC2)cc1] | 2-butyl-1-(4-(((2-cyclopropylethyl)amino)methyl)benzyl)-1H-imidazo[4,5-c]quinolin-4-amine |
| 63-34 | 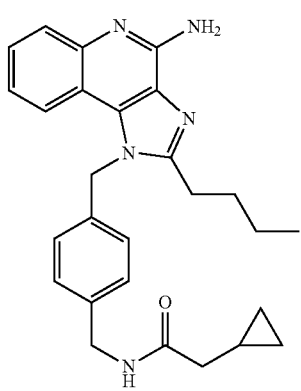 [SMILES: CCCCc1nc2c(N)nc3ccccc3c2n1Cc1ccc(CNC(=O)CC2CC2)cc1] | N-(4-((4-amino-2-butyl-1H-imidazo[4,5-c]quinolin-1-yl)methyl)benzyl)-2-cyclopropylacetamide |

TABLE 1-continued
| Compound No. | Formula | Name |
|---|---|---|
| 63-35 | 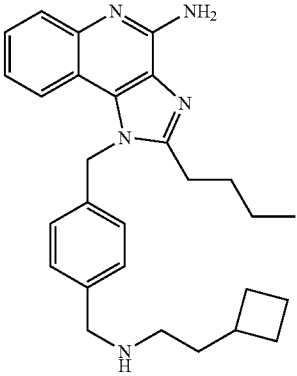 [SMILES: CCCCc1nc2c(N)nc3ccccc3c2n1Cc1ccc(CNCCC2CCC2)cc1] | 2-butyl-1-(4-(((2-cyclobutylethyl)amino)methyl)benzyl)-1H-imidazo[4,5-c]quinolin-4-amine |
| 63-36 | 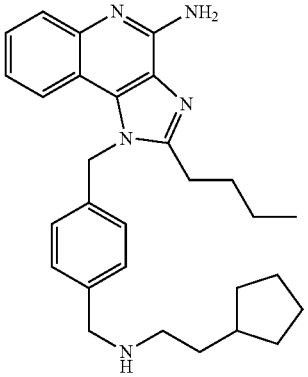 [SMILES: CCCCc1nc2c(N)nc3ccccc3c2n1Cc1ccc(CNCCC2CCCC2)cc1] | 2-butyl-1-(4-(((2-cyclopentylethyl)amino)methyl)benzyl)-1H-imidazo[4,5-c]quinolin-4-amine |
| 63-38 | 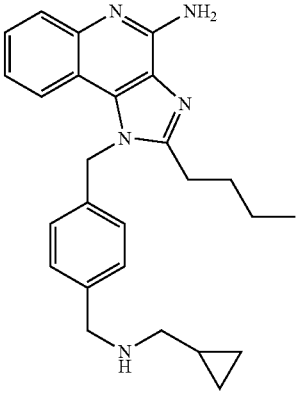 [SMILES: CCCCc1nc2c(N)nc3ccccc3c2n1Cc1ccc(CNCC2CC2)cc1] | 2-butyl-1-(4-(((cyclopropylmethyl)amino)methyl)benzyl)-1H-imidazo[4,5-c]quinolin-4-amine |
| 63-39 | 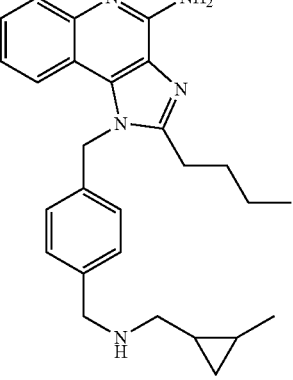 | 2-butyl-1-(4-((((2-methylcyclopropyl)methyl)amino)methyl)benzyl)-1H-imidazo[4,5-c]quinoline-4-amine |

TABLE 1-continued

| Compound No. | Formula | Name |
|---|---|---|
| 63-40 | | 2-butyl-1-(4-((((2,2-dimethylcyclopropyl)methyl)amino)methyl)benzyl)-1H-imidazo[4,5-c]quinolin-4-amine |
| 63-41 | | 2-butyl-1-(4-(((2-cyclopropyl-2-methylpropyl)amino)methyl)benzyl)-1H-imidazo[4,5-c]quinoline-4-amine |
| 63-42 | | 2-butyl-1-(4-(((2-(1-methylcyclopropyl)ethyl)amino)methyl)benzyl)-1H-imidazo[4,5-c]quinolin-4-amine |
| 63-43 | | 2-butyl-1-(4-(((3-cyclopropyl)amino)metthyl)benzyl)-1H-imidazo[4,5-c]quinolin-4-amine |

TABLE 1-continued
| Compound No. | Formula | Name |
|---|---|---|
| 63-44 | 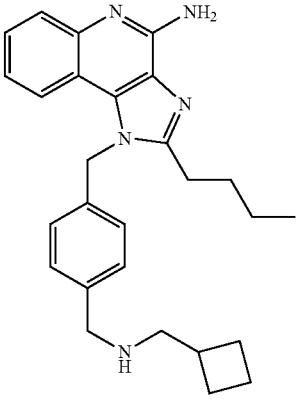 [SMILES: CCCCc1nc2c(N)nc3ccccc3c2n1Cc1ccc(CNCC2CCC2)cc1] | 2-butyl-1-(4-((((cyclobutylmethyl)amino)methyl)benzyl)-1H-imidazo[4,5-c]quinolin-4-amine |
| 63-45 | 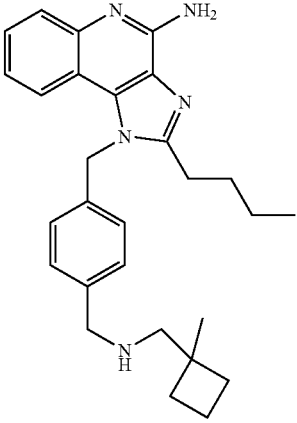 [SMILES: CCCCc1nc2c(N)nc3ccccc3c2n1Cc1ccc(CNCC2(C)CCC2)cc1] | 2-butyl-1-(4-(((((1-methylcyclobutyl)methyl)amino)methyl)benzyl)-1H-imidazo[4,5-c]quinoline-4-amine |
| 63-46 | 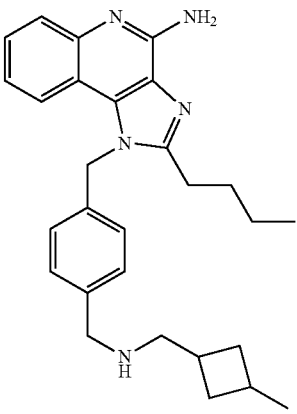 [SMILES: CCCCc1nc2c(N)nc3ccccc3c2n1Cc1ccc(CNCC2CC(C)C2)cc1] | 2-butyl-1-(4-(((((3-methylcyclobutyl)methyl)amino)methyl)benzyl)-1H-imidazo[4,5-c]quinolin-4-amine |

TABLE 1-continued
| Compound No. | Formula | Name |
|---|---|---|
| 63-47 | 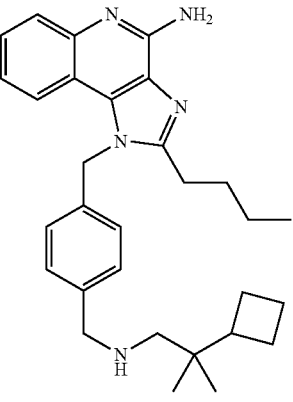 [SMILES: CCCCc1nc2c(N)nc3ccccc3c2n1Cc1ccc(CNCC(C)(C)C2CCC2)cc1] | 2-butyl-1-(4-(((2-cyclobutyl-2-methylpropyl)amino)methyl)benzyl)-1H-imidazo[4,5-c]quinolin-4-amine |
| 63-48 | 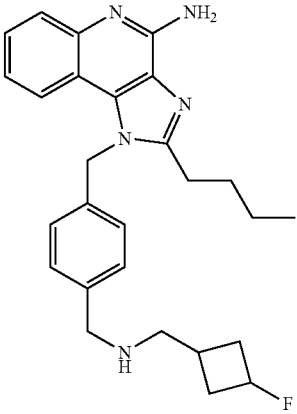 [SMILES: CCCCc1nc2c(N)nc3ccccc3c2n1Cc1ccc(CNCC2CC(F)C2)cc1] | 2-butyl-1-(4-((((3-fluorocyclobutyl)methyl)amino)methyl)benzyl)-1H-imidazo[4,5-c]quinoline-4-amine |
| 63-49 | 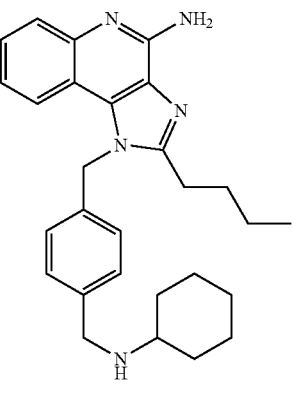 [SMILES: CCCCc1nc2c(N)nc3ccccc3c2n1Cc1ccc(CNC2CCCCC2)cc1] | 2-butyl-1-(4-((cyclohexylamino)methyl)benzyl)-1H-imidazo[4,5-c]quinolin-4-amine |

Additional compounds are listed in Table 2.

TABLE 2

| Compound No. | Formula | Name |
|---|---|---|
| 63-00 | | 1-(4-(aminomethyl)benzyl)-2-butyl-1H-imidazo[4,5-c]quinolin-4-amine |
| 63-31 | | N-(4-((4-amino-2-butyl-1H-imidazo[4,5-c]quinolin-1-yl)methyl)benzyl)palmitamide |
| 63-32 | | 2-butyl-1-(4-((hexadecylamino)methyl)benzyl)-1H-imidazo[4,5-c]quinolin-4-amine |

TABLE 2-continued

| Compound No. | Formula | Name |
|---|---|---|
| 63-37 | | N-(4-((4-amino-2-butyl-1H-imidazo[4,5-c]quinolin-1-yl)methyl)benzyl)pent-4-ynamide |

In some embodiments, the compounds of the invention exclude those listed in Table 2.

In some embodiments, provided is a compound selected from Compounds Nos. 63-01 to 63-30, 63-33 to 63-36, and 63-38 to 63-49 in Table 1, or a salt thereof. In some embodiments, the compound is selected from the group consisting of one or more of Compound Nos. 63-01 to 63-30 in Table 1, or a salt thereof. In some embodiments, the compound is selected from the group consisting of one or more of Compound Nos. 63-33 to 63-36 and 63-38 to 63-49 in Table 1, or a salt thereof.

The invention also includes all salts of compounds referred to herein, such as pharmaceutically acceptable salts. The invention also includes any or all of the stereochemical forms, including any enantiomeric or diastereomeric forms, and any tautomers or other forms of the compounds described. Unless stereochemistry is explicitly indicated in a chemical structure or name, the structure or name is intended to embrace all possible stereoisomers of a compound depicted. In addition, where a specific stereochemical form is depicted, it is understood that other stereochemical forms are also embraced by the invention. All forms of the compounds are also embraced by the invention, such as crystalline or non-crystalline forms of the compounds. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

Compounds of the present disclosure are potent TLR7/8 agonists exhibiting balanced bioactivity against both receptors and possess physiochemical properties such as increased hydrophobicity. Compounds with potent agonist bioactivity against both TLR7 and TLR8 receptors are potentially more effective immune adjuvants than agonists specific for only one of these TLRs, and would promote innate immune responses in a wider range of antigen presenting cells and other key immune cell types, including plasmacytoid and myeloid dendritic cells, monocytes, and B cells (see e.g., Vasilakos et al 2013 *Expert Rev Vaccines* 12:809-819). Compounds with physiochemical properties such as increased hydrophobicity are known to be compatible with oil-based formulation approaches, and enable pharmaceutical compositions that promote retention of the compound at the site of injection.

In some embodiments, compounds of formula (J) or (K) are capable of activating both TLR7 and TLR8. In some embodiments, the compound of formula (J) or (K) has an $EC_{50}$ for TLR7 of about 200 nM or lower and an $EC_{50}$ for TLR8 of about 2000 nM or lower, wherein the $EC_{50}$ values are as described in Example B1. In some embodiments, the compound of formula (J) or (K) has an $EC_{50}$ for TLR7 of about 50 nM or lower, and an $EC_{50}$ for TLR8 of about 1000 nM or lower. In some embodiments, the compound of formula (J) or (K) has an $EC_{50}$ for TLR7 of about 200 nM, about 175 nM, about 150 nM, about 125 nM, about 100 nM, about 75 nM, about 50 nM, about 40 nM, about 30 nM, about 20 nM, about 10 nM, about 8 nM, about 6 nM, about 5 nM, about 4 nM, about 3 nM, about 2 nM, about 1 nM, or about 0.5 nM; and an $EC_{50}$ for TLR8 of about 2000 nM, 1500 nM, 1000 nM, 900 nM, 800 nM, 700 nM, 600 nM, 500 nM, 400 nM, 300 nM, 200 nM, 100 nM, 50 nM, 25 nM, 10 nM, 5 nM, 1 nM, or 0.5 nM.

Compounds of formula (J-1) or (K-1) are N-alkyl derivatives of 1-(4-(aminomethyl)benzyl)-2-butyl-1H-imidazo[4,5-c]quinolin-4-amine (IMDQ); while compounds of formula (J-2) or (K-2) are N-acyl derivatives of IMDQ. IMDQ (Compound No. 63-00) shows potent in vitro activities for both TLR7 and TLR8 receptors (see e.g., U.S. Pat. Nos. 8,728,486 and 9,441,005). Alkyl chain modification of compounds of the present invention at the benzylic amine increases hydrophobicity, and thereby enables pharmaceutical compositions that promote retention of the compound at the site of injection. However, while alkyl chain derivatives of increasing carbon chain length may provide significant increases in hydrophobicity (for example as estimated by the calculated partitioning coefficient or c Log P), these derivatives can also have diminished agonist potency against both TLR7 and TLR8, or selectively have diminished bioactivity against one of the two receptors. For example, the N-octadecanoyl derivative (Compound No. 63-13) is over 40-fold less potent against TLR7 and 26-fold less potent against TLR8 than its parent congener IMDQ in the same in vitro human immune cell bioactivity assays. Unexpectedly, the N-tetradecanoyl derivative (Compound No. 63-10) of IMDQ is only 2 and 2.4-fold less potent against TLR7 and TLR8, respectively, than IMDQ. These data demonstrate that an alkyl chain of optimal length provides potent balanced TLR7/8 agonist bioactivity, as well as increased hydrophobicity that allows for incorporation into pharmaceutical compositions that promote retention of the compound at the site of injection.

Compounds of formula (J-1) or (K-1) are N-alkyl derivatives of 1-(4-(aminomethyl)benzyl)-2-butyl-1H-imidazo[4,5-c]quinolin-4-amine (IMDQ). While alkyl chain derivatives of increasing carbon chain length may provide increases in hydrophobicity (for example as estimated by the calculated partitioning coefficient or c Log P), these derivatives can also have diminished agonist potency against both TLR7 and TLR8, or selectively have diminished bioactivity against one of the two receptors. For example, the 4-octadecylamino derivative (Compound No. 63-29) is 19-fold less potent against TLR7 and over 12-fold less potent against TLR8 than its parent congener IMDQ in the same in vitro human immune cell bioactivity assays (see e.g., Example B1). Interestingly, the 4-pentylamino derivative (Compound No. 63-17) is only 2-fold less potent against TLR7 and is 2-fold more potent against TLR8 than IMDQ, but shows significantly less hydrophobicity than Compound No. 63-29. Unexpectedly, the 4-(2-cyclopropylethyl)amino derivative (Compound No. 63-33) is only 4-fold less potent against TLR7 and 2.9-fold more potent against TLR8 than IMDQ, and has an increased c Log P compared to the linear 5 carbon variant (Compound No. 63-17). These data demonstrate that an alkyl chain of optimal length provides potent balanced TLR7/8 agonist bioactivity, as well as increased hydrophobicity that may allow for incorporation into pharmaceutical compositions that promote retention of the compound at the site of injection.

A TLR7/8 agonist small molecule with balanced dual potency would also allow for the synthesis and characterization of a single active pharmaceutical ingredient, thereby facilitating GMP manufacturing at lower costs and enabling a more straightforward and predictable regulatory pathway.

Compounds of formula (J) may be synthesized according to Scheme 1 and/or using methods known in the art.

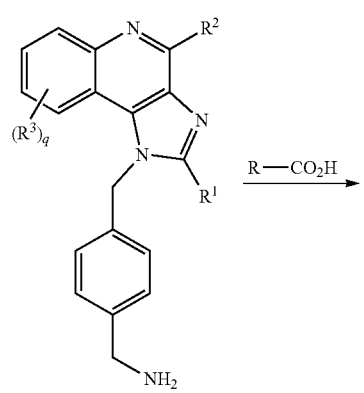

Scheme 1

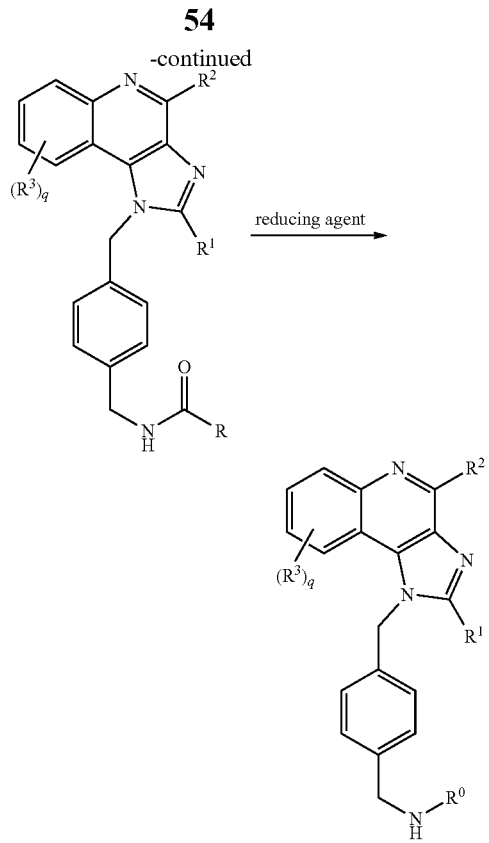

wherein $R^1$, $R^2$, q, and $R^3$ are as defined for formula (J), R, and $R^0$ are hydrocarbyl groups.

Preferred compounds of formula (J) where X is —NH—, $R^0$ is —$(CH_2)_m R^A$, m is 1 or 2, and $R^A$ is cyclopropyl, cyclobutyl, cyclopentyl, or cyclohexyl can be prepared using the following carboxylic acids: cyclopropanecarboxylic acid, cyclopropyl acetic acid, cyclobutanecarboxylic acid, cyclobutylacetic acid, cyclopentanecarboxylic acid, cyclopentylacetic acid, cyclohexanecarboxylic acid, and cyclohexaneacetic acid. Preferred compounds of formula (J) where X is —NH—, $R^0$ is —$(CH_2)_m R^A$, m is 1, 2, or 3, and $R^A$ is cyclopropyl, 2-methylcyclopropyl, 2,2,-dimethylcyclopropyl, 1-methylcyclopropyl, 1-methylcyclobutyl, 3-methylcyclobutyl, or 3-fluorocyclobutyl can be prepared using the following carboxylic acids: cyclopropanecarboxylic acid, 2-methylcyclopropane carboxylic acid, 2,2-dimethylcyclopropane carboxylic acid, 1-methylcyclopropane carboxylic acid, 1-methylcyclobutane carboxylic acid, 3-methylcyclobutane carboxylic acid, or 3-fluorocyclobutane carboxylic acid. Preferred compounds of formula (J) where X is —NH—, $R^0$ is —$(CH_2)(C(CH_3)_2)R^A$, and $R^A$ is cyclopropyl or cyclobutyl can be prepared using the following carboxylic acids: cyclopropane carboxylic acid or cyclobutane carboxylic acid. A detailed description of the synthesis scheme for the representative Compound No. 63-33 can be found in Example S3.

In some embodiments, where $R^1$ is $C_3$-$C_6$ alkyl (e.g., n-butyl), $R^2$ is $NH_2$, X is —NH—, $R^0$ is —$(CH_2)_m R^A$, m is 0, and $R^A$ is cycloalkyl, the compounds are synthesized according to Scheme 1-2. A compound of formula (J), wherein $R^1$ is n-butyl, $R^2$ is $NH_2$, X is —NH—, $R^0$ is —$(CH_2)_m R^A$, m is 0, and $R^A$ is cyclohexyl (Compound No. 63-49) is prepared according to the synthesis described in Example S10.

Scheme 1-2
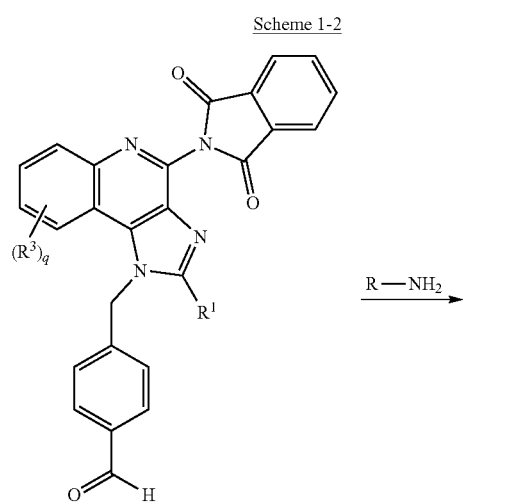
R—NH₂ →
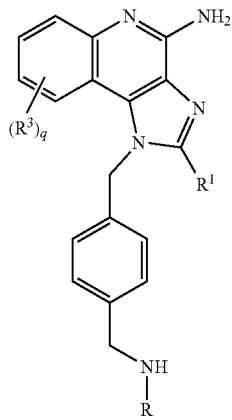
wherein R¹, q, and R³ are as defined for formula (J), and R is a cycloalkyl group.
Compounds of formula (K) may be synthesized according to Scheme 2 and/or using methods known in the art.
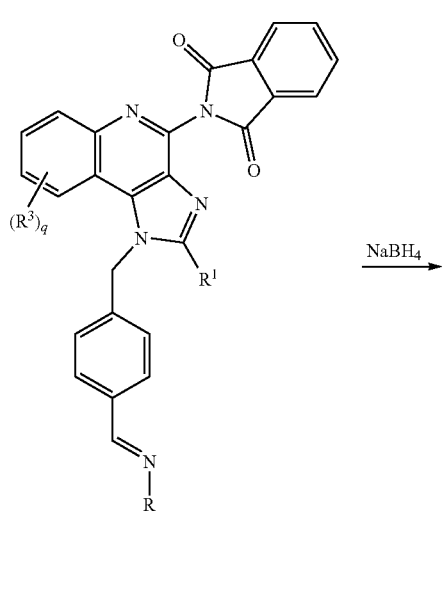
NaBH₄ →
Scheme 2
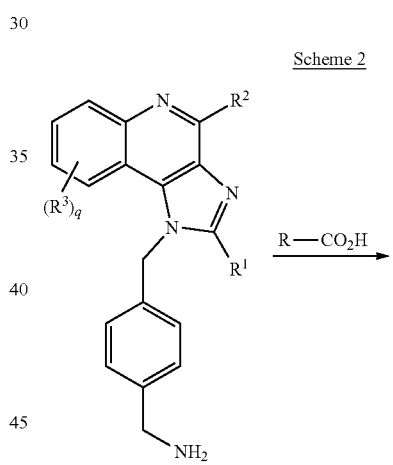
R—CO₂H →
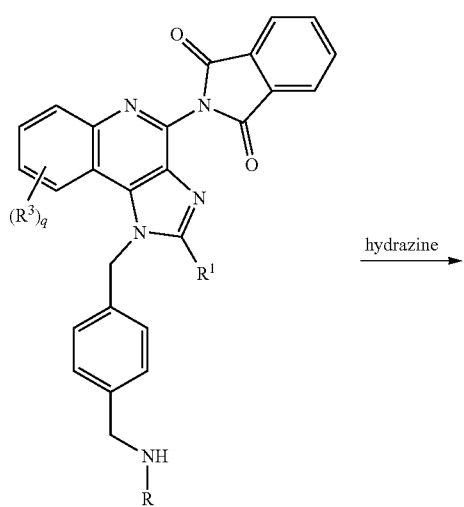
hydrazine →
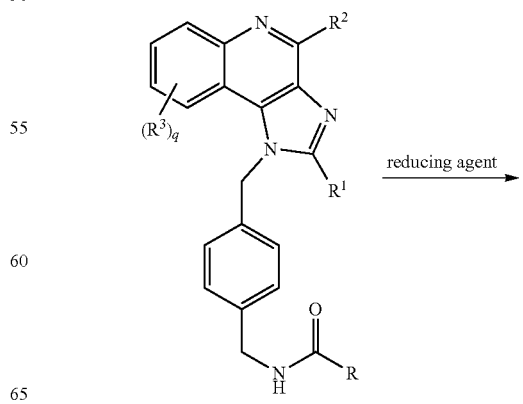
reducing agent →

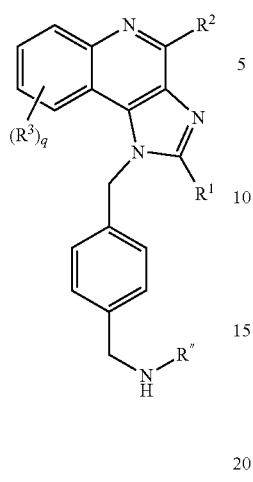

wherein $R^1$, $R^2$, q, and $R^3$ are as defined for formula (K), R, and R″ are linear alkyl groups.

Preferred compounds of formula (K) where X is —NH(C=O)— and n is an integer from 4 to 21 provided that the compound is other than N-(4-((4-amino-2-butyl-1H-imidazo[4,5-c]quinolin-1-yl)methyl)benzyl)palmitamide (Compound No. 63-31) can be prepared using the following carboxylic acids; pentanoic, hexanoic, heptaonic, octanoic, nonanoic, decanoic, undecanoic, dodecanoic, tridecanoic, tetradecanoic, pentadecanoic, hexadecanoic, heptadecanoic, octadecanoic, nonadecanoic, icosanoic, heneicosanoic, and docosanoic. A detailed description of the synthesis scheme for the representative Compound Nos. 63-10 and 63-17 can be found in Examples S1 and S2, respectively.

In some embodiments, where $R^1$ is $C_3$-$C_6$ alkyl (e.g., n-butyl), $R^2$ is $NH_2$, and q is 0, the compounds are synthesized according to Scheme 3 or 4. For more detailed description of the individual reaction steps useful for preparing Compound No. 63-00, the starting compound in Schemes 3 and 4, see e.g., U.S. Pat. Nos. 8,728,486 and 9,441,005.

Scheme 3

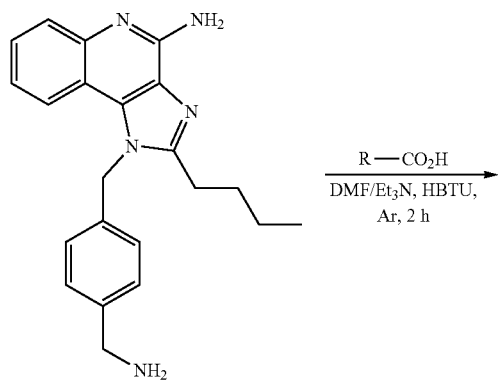

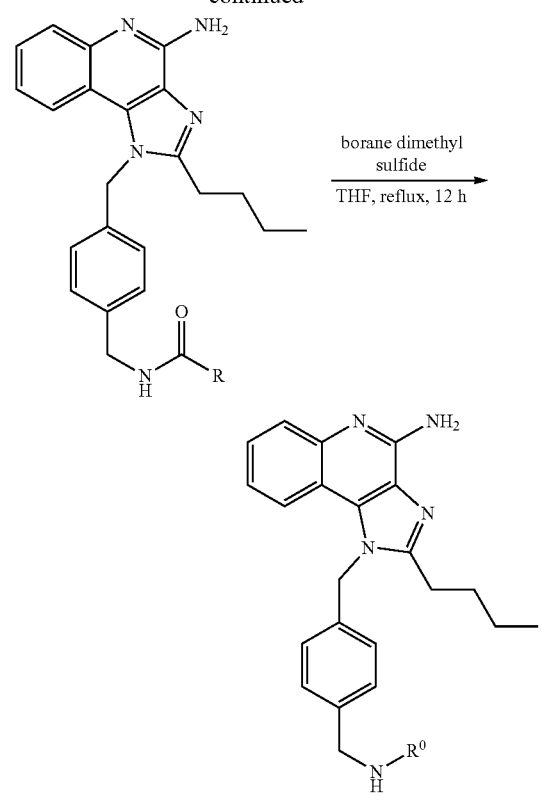

wherein R and $R^0$ are hydrocarbyl groups.

Scheme 4

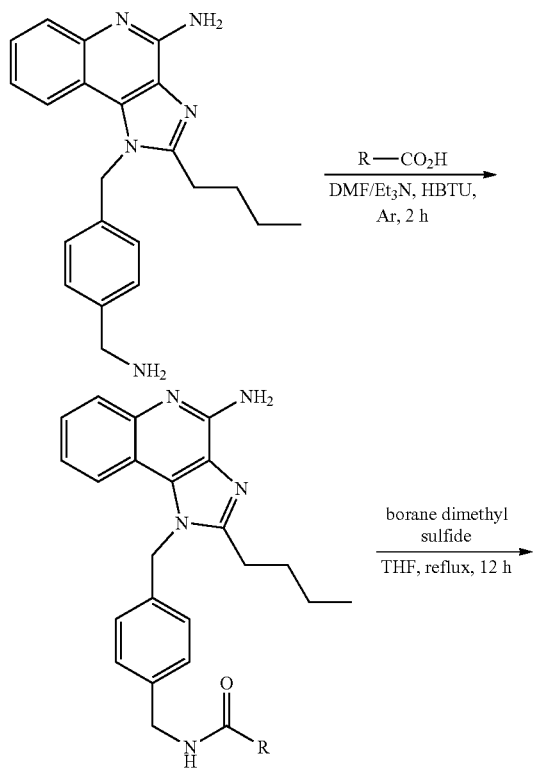

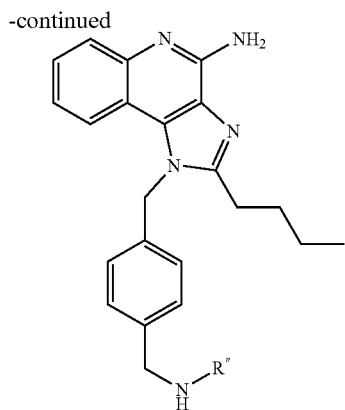

wherein R and R" are linear alkyl groups.

Those skilled in the art will appreciate that other synthetic routes may be employed to synthesize the range of compounds described within the invention including various solvents, catalysts, reducing agents, temperatures, reaction times, and atmospheric conditions.

Conventional methods and techniques of separation and purification can be used to isolate the compounds of the invention. Techniques may include high performance liquid chromatography (HPLC) with different matrices (see e.g., C18, C8, C4, etc.), chromatography using typical adsorbants (see e.g., silica gel, activated carbon, alumina, zeolites, and the like), recrystallization, and differential extraction methods (e.g., liquid-liquid, solid phase, and the like).

III. PHARMACEUTICAL COMPOSITIONS

Pharmaceutical compositions comprising alkyl chain modified 1H-imidazo[4,5-c]quinoline TLR7/8 agonists of the present disclosure are also provided. The pharmaceutical compositions routinely contain one or more pharmaceutically acceptable excipients. In some embodiments, the pharmaceutical compositions further comprise an antigen. The pharmaceutical compositions of the present disclosure are preferably sterile, and preferably essentially endotoxin-free. Excipients Pharmaceutically acceptable excipients of the present disclosure include, for instance, oils, lipids, solvents, bulking agents, surfactants, buffering agents, tonicity adjusting agents, and preservatives (see, e.g., Pramanick et al 2013 *Pharma Times* 45:65-77). In some embodiments, the pharmaceutical compositions comprise an excipient that functions as one or more of a solvent, a bulking agent, a buffering agent, and a tonicity adjusting agent (e.g., sodium chloride in saline may serve as both an aqueous vehicle and a tonicity adjusting agent). The pharmaceutical compositions of the present disclosure are suitable for parenteral routes of administration, and in certain instances preferentially by intratumoral administration. In certain embodiments, the pharmaceutical compositions of the present disclosure are not intended for enteral administration.

In some embodiments, the pharmaceutical compositions comprise an oil-based excipient to solubilize the TLR7/8 agonist compound so as to enable parenteral administration, as well as to promote retention of the compound at the site of injection. Non-limiting examples of oil-based excipients are known to those skilled in the art, including pharmaceutical-grade sesame oil, soybean oil, castor oil, corn oil, cottonseed oil, peanut oil, Miglyol®, squalene oil, and the like. These oils may be purified, or refined, by a chromatography process to reduce the levels of polar impurities, thereby producing a USP-NF/JP/Ph. Eur.-grade products that possess consistent properties and impurity profiles.

In some embodiments, the TLR7/8 agonist compound is initially solubilized in a 100% ethanol excipient and then diluted into the oil to a final concentration of between 2-20% ethanol to facilitate solubilization of the compound in the oil. Ethanol suitable for use is one which does not contain water or denaturants, see e.g., 200 proof ethanol, dehydrated alcohol USP-grade, etc.

In some embodiments, the pharmaceutical compositions comprise a preservative. Suitable preservatives include, for instance, antimicrobial agents and antioxidants. In preferred embodiments, the pharmaceutical composition is prepared under sterile conditions and is in a single use container, and thus does not necessitate inclusion of an anti-microbial agent. One skilled in the art will recognize that pharmaceutical grade anti-oxidants, used to prevent coloring, odors, or peroxide formation, may be added to these oil-based formulations, including but not limited to butylated hydroxyanisole (BHA), butylated hydroxytoluene (BHT), tertiary butylhydroquinone (TBHQ), vitamin E, propyl gallate, and the like. In certain embodiments, the added antioxidant concentration in the formulation is at least 10 ppm, 50 ppm, 100 ppm, 300 ppm, 500 ppm, and up to 1000 ppm, in order to ensure stability of the oil-based formulation for periods of time up to 1 year when stored at temperatures from 5° C. to 40° C.

In some embodiments, the pharmaceutical compositions comprise an oil-in-water based nanoemulsion (see e.g., Dowling et al 2017 *JCI Insight* 2:e91020) or a liposome-based formulation (see e.g., VanHoeven et al 2017 *Sci Rep* 7:46426). In one embodiment exemplifying an oil-in-water nanoemulsion-based pharmaceutical composition, the TLR7/8 agonist compounds of formula (J) or (K) are dissolved in an oil phase composed of phospholipids (e.g., 1,2-dimyristoyl-sn-glycero-3-phosphocholine; 1,2-dipalmitoyl-sn-glycero-3-phosphocholine; 1,2-distearoyl-sn-glycero-3-phosphocholine; 1,2-distearoyl-sn-glycero-3-phospho-(1'-rac-glycerol); 1,2-dioleoyl-sn-glycero-3-phosphocholine; L-α-phosphatidylcholine; and the like), triglyceride-based oils (see e.g., sesame oil, soybean oil, castor oil, corn oil, cottonseed oil, peanut oil, Miglyol®, squalene oil, and the like), and optionally an organic modifier (e.g., ethanol). Next, an aqueous phase containing a suitable buffer, isotonic agent, emulsifying agent, and optionally a preservative is added to the oil phase and a crude emulsion is formed by high shear mixing (e.g., Polytron®) for 5-10 minutes. Finally, a nanoemulsion containing particles with a mean diameter in the range of 100-150 nm (assessed by dynamic light scattering), and dispersity index in the range of 0.1-0.2, is formed by processing the crude emulsion through a high shear homogenizer (see e.g., Microfluidizer M110P) for 10-15 passes at 30,000 psi.

In another embodiment exemplifying a liposome-based pharmaceutical composition, the TLR7/8 agonist compounds of formula (J) or (K) are dissolved in organic modifiers and a suitable mixture of phospholipids using various ratios of neutrally-charged, positively-charged, negatively-charged, and PEGylated phospholipids, with varying lipid tail lengths, and cholesterol (depending on the desired physiochemical properties of the liposome). The organic solvents are then removed using a rotary evaporator and the lipid/compound film re-dissolved in an aqueous buffer until the formulation is translucent with no visible particles. Finally, the resulting multi-lamellar liposomes are processed using either high shear homogenization or a membrane extruder (e.g., Lipex®) into unilamellar liposomes with a mean diameter in the range of 100-150 nm (assessed by dynamic light scattering) and dispersity index in the range of 0.1-0.2. These examples are non-limiting, and one skilled in the art will recognize that oil-in-water nanoemulsions and liposome-based pharmaceutical compositions can be formed by any of a number of differing methods (see e.g., Brito et al 2013 *Seminar Immunol* 25:130-145).

In some embodiments, the pharmaceutical compositions comprise a bulking agent. Bulking agents are particularly useful when the pharmaceutical composition is to be lyophilized before administration. In some embodiments, the bulking agent is a lyoprotectant that aids in the stabilization and prevention of degradation of the active agents during freeze-drying and/or during storage. Suitable bulking agents are sugars (mono-, di-, and polysaccharides) such as sucrose, lactose, trehalose, mannitol, sorbital, glucose, and raffinose.

In some embodiments, the pharmaceutical compositions comprise a buffering agent. Buffering agents control pH to inhibit degradation of the active agent during processing, storage, and optionally reconstitution. Suitable buffers include, for instance, salts comprising acetate, citrate, phosphate or sulfate. Other suitable buffers include, for instance, amino acids such as arginine, glycine, histidine, and lysine. The buffering agent may further comprise hydrochloric acid or sodium hydroxide. In some embodiments, the buffering agent maintains the pH of the composition within a range of 4 to 9. In some embodiments, the pH is greater than (lower limit) 4, 5, 6, 7, or 8. In some embodiments, the pH is less than (upper limit) 9, 8, 7, 6, or 5. That is, the pH is in the range of from about 4.0 to 9.0, in which the lower limit is less than the upper limit.

In some embodiments, the pharmaceutical compositions comprise a tonicity adjusting agent. Suitable tonicity adjusting agents include, for instance, dextrose, glycerol, sodium chloride, glycerin, and mannitol.

Antigens

In one aspect, the present disclosure provides pharmaceutical compositions comprising an antigen. In some embodiments, the pharmaceutical composition comprises an alkyl chain modified 1H-imidazo[4,5-c]quinoline TLR7/8 agonist, one or more excipients, and an antigen. In some of these embodiments, the antigen is a protein antigen. In some of these embodiments, the antigen is a polysaccharide antigen, which is preferably covalently attached to a carrier protein. In some embodiments, the antigen is a microbial antigen, an allergen, or a tumor associated antigen. In some embodiments, the antigen is a viral antigen, a protozoan antigen, a bacterial antigen, or a fungal antigen. In some embodiments, the tumor antigen is a self-antigen or neoantigen.

In some embodiments, the pharmaceutical compositions comprise a microbial antigen selected from the group consisting of a viral antigen, a bacterial antigen, a fungal antigen, and a parasite antigen. In some embodiments, the microbial antigen is from a microbe that causes an infectious disease in a nonhuman, mammalian subject. In some embodiments, the microbial antigen is from a microbe that causes an infectious disease in a human subject. In some embodiments, the infectious disease is caused by a virus, a bacterium, a fungus, or a protozoan parasite. Suitable microbial antigens include, for instance, antigens of adenovirus type 4, adenovirus type 7, *Bacillus anthracis* (anthrax), *Mycobacterium tuberculosis, Corynebacterium diphtherias* (e.g., diphtheria toxoid), *Clostridium tetani* (e.g., tetanus toxoid), *Bordetella pertussis, Haemophilus influenzae* type B, hepatitis A virus, hepatitis B virus (e.g., HBsAg), human papillomavirus (types 6, 11, 16, 18, 31, 33, 45, 52, and 58) influenza virus type A and B (e.g., haemagglutinin, neuraminadase), influenza virus type B, parainfluenza virus, Japanese encephalitis virus, measles virus, mumps virus, rubella virus, *Neisseria menigitidis* (Groups A, B, C, Y, and W-135), *Streptococcus pneumoniae* (serotypes 1, 3, 4, 5, 6A, 6B, 7F, 9V, 14, 18C, 19A, 19F, and 23F), poliovirus, rabies virus, rotavirus, vaccinia virus, *Salmonella typhi*, varicella zoster virus, and yellow fever virus (see, e.g., Plotkin, S. A., Orenstein, W., Offit, P. A., Edwards K. M. (2017). Plotkin's Vaccines, $7^{th}$ edition. Elsevier). In some embodiments, the microbial antigen is a viral antigen of Herpes simplex virus type 1 or 2, human herpes virus, human immunodeficiency virus type 1, and respiratory syncytial virus. In some embodiments, the microbial antigen is a fungal antigen of *Candida albicans, Aspergillus flavus, Cryptococcus neoformans, Histoplasma capsulatum*, and *Pneumocystis carinii*. In some embodiments, the microbial antigen is a parasite antigen of a *Leishmania* species, a *Plasmodium* species, a *Schistosoma* species, or a *Trypanosoma* species.

In some embodiments, the pharmaceutical compositions comprise an allergen. In some embodiments, the allergen is an environmental antigen such as mammalian, insect, plant, and mold allergens. In some embodiments, the mammalian allergen includes fur and dander. Suitable mammalian allergens include, for instance, cat Fel d 1, cow Bos d 2, dog Can f I, and Can f II, horse Equ c1, and mouse MUP. In some embodiments, the insect allergen includes insect feces and venom. Exemplary insect allergens include ant Sol i2, bee PLA and Hya, cockroach Bla g Bd9OK, Bla g4, GST, and Per a3, dust mite Der p2, Der f2, Der p10, and Tyr p2, hornet Dol m V, mosquito Aed a 1, and yellow jacket hyaluronidase and phospholipase. In some embodiments, the plant allergen includes grass, weed, and tree allergens (e.g., pollens). Suitable grass allergens include, for instance, allergens of Kentucky bluegrass, meadow fescue, orchard grass, redtop grass, perennial ryegrass, sweet vernal grass, and timothy. Exemplary plant allergens include barley Hor v 9, birch Bet v1 and v2, cherry Pru a 1, corn Zml3, grass Phl p 1, 2, 4, 5, 6, 7, 11, and 12, Hol 1 5, Cyn d 7 and d12, cedar Jun a 2, Cry j 1, and j2, juniper Jun o2, latex Hey b7, yellow mustard Sin a I, rapeseed Bra r 1, ragweed Amb a 1, and rye Lol p1. In some embodiments, the mold allergen is an *Aspergillus fumigatus* allergen such as Asp f 1, 2, 3, 4, and 6. In some embodiments, the allergen is a food allergen such as a shell fish allergen, a legume allergen, a nut allergen or a milk allergen. Exemplary food allergens include shrimp tropomyosin, peanut Ara h 1, 2, 3, 8, and 9, walnut Jug r 1 and 3, hazelnut Cor a 1, 14, and 8 LTP, cow's milk lactalbumin, casein, and lactoferrin.

In some embodiments, the pharmaceutical compositions comprise a tumor antigen. In some embodiments, the tumor antigen comprises the amino acid sequence of a full length protein or a fragment thereof (e.g., a polypeptide of about 10 to about 100 amino acids in length). In some embodiments, the tumor antigen comprises a full length protein or polypeptide fragment of one or more of the group consisting of WT1, MUC1, LMP2, HPV E6, HPV E7, EGFRvIII, Her-2/neu, idiotype, MAGE A3, p53, NY-ESO-1 (CTAG1), PSMA, CEA, MelanA/Mart1, Ras, gp100, proteinase 3, bcr-able, tyrosinase, survivin, PSA, hTERT, sarcoma translocation breakpoints, EphA2, PAP, MP-IAP, AFP, EpCAM, ERG, NA17-A, PAX3, ALK, androgen receptor, cyclin B1, MYCN, PhoC, TRP-2, mesothelin, PSCA, MAGE A1, CYP1B1, PLAC1, BORIS, ETV6-AML, NY-BR-1, RGS5, SART3, carbonic anhydrase IX, PAXS, OY-TES1, sperm protein 17, LCK, HMWMAA, AKAP-4, SSX2, XAGE 1, B7-H3, legumain, Tie 2, Page4, VEGFR2, MAD-CT-1, FAP, PAP, PDGFR-beta, MAD-CT-2, CEA, TRP-1 (gp75), BAGE1, BAGE2, BAGE3, BAGE4, BAGE5, CAMEL, MAGE-A2, MAGE-A4, MAGE-A5, MAGE-A6, MAGE-A8, MAGE-A9, MAGE-A10, MAGE-A11, MAGE-A12, and Fos-related antigen 1. In some preferred embodiments, the tumor antigen comprises an amino acid sequence or fragment thereof from one or more of the group consisting of gp100, hTERT, MAGE A1, MAGE A3, MAGE A10, MelanA/Mart1, NY-ESO-1, PSA, Ras, survivin, TRP1 (gp75), TRP2, and tyrosinase.

IV. Methods of Use

The pharmaceutical compositions of the present disclosure are suitable for a plurality of uses involving stimulating an immune response in a mammalian subject in need thereof. Mammalian subjects include, but are not limited to, humans, nonhuman primates, rodents, pets, and farm animals. In some embodiments, the pharmaceutical compositions are administered to the subject in an amount effective to achieve a specific outcome.

Dosage and Mode of Administration

As with all pharmaceutical compositions, the effective amount and mode of administration may vary based on several factors evident to one skilled in the art. Factors to be considered include potency of the alkyl chain modified 1H-imidazo[4,5-c]quinoline TLR7/8 agonist compound, ability of the compound and pharmaceutical composition to promote retention of the agonist compound at the site of administration, the route of administration, and whether the pharmaceutical composition contains an antigen. Other factors to be considered include the disease modification outcome to be achieved, and the number/frequency of doses to be administered during a therapeutic regimen.

A suitable dosage range is one that provides the desired clinical effect. Dosage may be determined by the amount of the TLR7/8 agonist in the pharmaceutical composition that needs to be administered to a subject to yield a desired therapeutic response with minimal adverse events. An exemplary dosage range of the TLR7/8 agonist compound given in an amount to be delivered by subject weight is from about 1 to 5000 ng/kg, such as about 1 to 2,500 ng/kg, about 1 to 1,000 ng/kg, about 1 to 500 ng/kg, about 1 to 250 ng/kg, about 1 to 100 ng/kg, about 1 to 50 ng/kg, about 50 to 2,500 ng/kg, about 50 to 1,000 ng/kg, about 50 to 500 ng/kg, about 100 to 5,000 ng/kg, about 100 to 2,500 ng/kg, about 100 to 1,000 ng/kg, about 100 to 500 ng/kg, about 500 to 5,000 ng/kg, about 1,000 to 5,000 ng/kg, about 2,000 to 5,000 ng/kg, about 2,500 to 5,000 ng/kg, about 3,000 to 5,000 ng/kg, or about 4,000 to 5,000 ng/kg. In some embodiments, the dosage is greater than about (lower limit) 1, 5, 10, 50, 100, 150, 200, 250, 300, 350, 400, 450, or 500 ng/kg. In some embodiments, the dosage is less than about (upper limit) 5000, 2000, 1000, 900, 800, 700, 600, 500, 450, 400, 350, 300, 250, 200, 150, or 100 ng/kg. That is, the dosage is anywhere in the range of from about 1 to 5000 ng/kg in which the lower limit is less than the upper limit. An exemplary dosage range of the TLR7/8 agonist given in an amount to be delivered to a subject is from about 1 to 5000 ng. In some embodiments, the dosage can be even higher, for example, about 2,500 to 500,000 ng/kg, about 5,000 to 500,000 ng/kg, about 2,500 to 150,000 ng/kg, about 2,500 to 100,000 ng/kg, about 2,500 to 50,000 ng/kg, about 2,500 to 25,000 ng/kg, about 2,500 to 10,000 ng/kg, about 10,000 to 500,000 ng/kg, about 25,000 to 500,000 ng/kg, about 50,000 to 500,000 ng/kg, about 100,000 to 500,000 ng/kg, or about 150,000 to 500,000 ng/kg.

In some embodiments, when the pharmaceutical composition further comprises an antigen, the antigen dosage range given in an amount to be delivered to a subject is from about 1 μg to 500 μg. In some embodiments, the antigen dosage is from about 1 μg to 50 μg. In some embodiments, the antigen dosage is greater than about (lower limit) 1, 5, 10, 15, 20, 25, 30, 35, 40, 45, 50, 100, 200, or 400 μg. In some embodiments, the antigen dosage is less than about (upper limit) 500, 400, 300, 200, 100, 50, 45, 40, 35, 30, 25, 20, 15, or 10 μg. That is, the antigen dosage is anywhere in the range of from about 1 to 500 μg in which the lower limit is less than the upper limit. The optimum antigen dosage can be determined by experimental means for each individual antigen.

Likewise, a suitable route of administration is one that provides the desired effect. In general, the pharmaceutical compositions of the present disclosure are intended for parenteral administration (e.g., not oral or rectal administration). Suitable routes of administration include injection, topical, and inhalation. In particular, the pharmaceutical compositions of the present disclosure may be administered by a route such as intratumoral, intramuscular, subcutaneous, intravenous, epidermal (gene gun), transdermal, and inhalation. Devices suitable for administration by inhalation include, for instance, atomizers, vaporizers, nebulizers, and dry powder inhalation delivery devices. In some embodiments, when the pharmaceutical compositions are intended to treat a solid tumor, the compositions are administered intratumorally. In one embodiment, intratumoral administration is by injection into at least one tumor lesion.

A suitable dosing regimen of the TLR7/8 agonist formulated in the pharmaceutical composition is one that provides the desired effect in a prophylactic or therapeutic context with minimal adverse events. The number of doses administered by a chosen route may be one or more than one. Frequency of dosing may range from weekly, bi-weekly, monthly, bi-monthly, or 3 to 12 months between doses. An exemplary dose frequency of the TLR7/8 agonist is from about once per week to once every 8 weeks. In some embodiments, the dose frequency is greater than about (upper limit) once every 8, 6, 4, 2, or 1 weeks. In some embodiments, the dose frequency is less than about (lower limit) once every 7, 10, or 14 days. An exemplary dose frequency range of the TLR7/8 agonist to be delivered to a subject is from about once every week to once every 4 weeks. In some embodiments, 2 doses are administered, with the second dose being administered one to two months after the first dose. In some embodiments, 3 doses are administered, with the second dose being administered one to two months after the first dose and the third dose being administered one to five months after the second dose. In other embodiments, a series of doses may be administered over a 3 to 12 month treatment schedule, where the dose frequency is once every week, every other week, every third week, or monthly. In other embodiments, a shorter or longer period of time may elapse between doses. In certain embodiments, the interval between successive dosages may vary in terms of number of weeks or number of months. In one embodiment, a series of 2, 3, 4, 5, or 6 weekly doses may be administered followed by a second series of weekly doses at a later time point. One skilled in the art will be able to adjust the dosage regimen by measuring biological outcomes such as antigen-specific antibody responses or tumor regression.

Stimulation of an Immune Response

In one aspect, the present disclosure provides methods of stimulating an immune response in a mammalian subject in need thereof, comprising administration to a mammalian subject a pharmaceutical composition in an amount and frequency sufficient to stimulate an immune response in said subject. "Stimulating" an immune response means increasing the immune response, which can arise from eliciting a de novo immune response (e.g., as a consequence of an initial vaccination regimen) or enhancing an existing immune response (e.g., as a consequence of a booster vaccination regimen). In some embodiments, stimulating an immune response comprises one or more of the group consisting of: stimulating IFNα production, stimulating production of Type 1 and/or Type 2 interferons, stimulating IL-6 production, stimulating TNFα production, stimulating B lymphocyte proliferation, stimulating interferon pathway-associated gene expression, stimulating chemoattractant-associated gene expression, and stimulating plasmacytoid dendritic cell (pDC) or myeloid dendritic cell (mDC) maturation. Methods for measuring stimulation of an immune response are known in the art and described in the biological examples of the present disclosure. In embodiments in which the pharmaceutical composition further comprises an antigen, stimulating an immune response comprises inducing an antigen-specific antibody response.

For instance, in some embodiments in which the pharmaceutical composition further comprises an antigen, the present disclosure provides methods of inducing an antigen-specific antibody and/or T cell response in a mammalian subject in need thereof by administering the pharmaceutical composition in an amount sufficient to induce an antigen-specific antibody and/or T cell response in said subject. "Inducing" an antigen-specific antibody response means increasing titers of antigen-specific antibodies above a threshold level, such as a pre-administration baseline titer or a seroprotective level. "Inducing" an antigen-specific T cell response means stimulating antigen-specific cytotoxic T lymphocytes, generating antigen-specific T cells that home to non-immunized tumor sites, generating T cells that are less exhausted and/or enhancing the immune response to additional tumor antigens by epitope spreading.

Analysis (both qualitative and quantitative) of the immune response can be by any method known in the art, including, but not limited to, measuring antigen-specific antibody production (including measuring specific antibody subclasses), activation of specific populations of lymphocytes such as B cells and helper T cells, measuring expression of a set of genes specific to a particular immune cell type, production of cytokines such as IFNα, IL-6, IL-12, IL-18, TNFα, and/or release of histamine from basophils or mast cells. Methods for measuring antigen-specific antibody responses include enzyme-linked immunosorbent assay (ELISA). Production of cytokines can also be measured by ELISA. Gene expression analysis can be performed by TaqMan® or nCounter® gene expression assays. Activation of specific populations of lymphocytes can be measured by proliferation assays and with fluorescence-activated cell sorting (FACS).

Preferably, a Th1-type immune response is stimulated (i.e., elicited or enhanced). With reference to the present disclosure, stimulating a Th1-type immune response can be determined in vitro or ex vivo by measuring cytokine production from cells treated with an active agent of the present disclosure (alkyl chain derivatives of 1H-imidazo[4,5-c]quinolines that are TLR7/8 agonists) as compared to control cells not treated with the active agent. Examples of "Th1-type cytokines" include, but are not limited to, IL-2, IL-12, IFNγ, and IFNα. In contrast, "Th2-type cytokines" include, but are not limited to, IL-4, IL-5, and IL-13. Cells useful for the determination of immunostimulatory activity include cells of the immune system such as antigen presenting cells, lymphocytes, and preferably macrophages and T cells. Suitable immune cells include primary cells such as peripheral blood mononuclear cells, including pDCs, monocytes, mDCs, and B cells, or splenocytes isolated from a mammalian subject.

Stimulating a Th1-type immune response can also be determined in a mammalian subject treated with an active agent of the present disclosure by measuring levels of IL-2, IL-12, and interferon either before and after administration, or as compared to a control subject not treated with the active agent. Stimulating a Th1-type immune response can also be determined by measuring the ratio of Th1-type to Th2-type antibody titers. "Th1-type" antibodies include human IgG1 and IgG3, and murine IgG2a. In contrast, "Th2-type" antibodies include human IgG2, IgG4, and IgE, and murine IgG1 and IgE.

Treatment of Disease

The present disclosure further provides methods of preventing an infectious disease in a mammalian subject in need thereof, comprising administration of a pharmaceutical composition in an amount sufficient to prevent an infectious disease in said subject. That is, in some embodiments, the present disclosure provides prophylactic vaccines. In some embodiments, the mammalian subject is at risk of exposure to an infectious agent. "Preventing" an infectious disease means to protect a subject from developing an infectious disease. In some embodiments, preventing an infectious disease further comprises protecting a subject from being infected with an infectious agent (e.g., protecting a subject from developing an acute or a chronic infection). Additionally, the present disclosure provides methods of ameliorating a symptom of an infectious disease in a mammalian subject in need thereof, comprising administration of a pharmaceutical composition in an amount sufficient to ameliorate a symptom of an infectious disease in said subject. That is, in some embodiments the present disclosure provides therapeutic vaccines. In some embodiments, the subject is acutely or chronically infected with an infectious agent. The infectious disease may be a viral (e.g., hepatitis, herpes or human papilloma viruses), bacterial, fungal, or parasitic disease. In some embodiments, the pharmaceutical composition further comprises a viral, bacterial, fungal, or parasitic antigen. "Ameliorating" a symptom of an infectious disease means to improve a symptom, preferably diminishing the extent of the disease.

Moreover, the present disclosure provides methods of ameliorating a symptom of an IgE-related disorder in a mammalian subject in need thereof, comprising administration of a pharmaceutical composition in an amount sufficient to ameliorate a symptom of an IgE-related disorder in said subject. In some preferred embodiments, the IgE-related disorder is an allergy. Allergies include, but are not limited to, allergic rhinitis (hay fever), sinusitis, eczema, and hives. In some embodiments, the pharmaceutical composition further comprises an allergen. "Ameliorating" a symptom of an IgE-related disorder means to improve a symptom, preferably diminishing the extent of the disorder. For instance, if the IgE-related disorder is allergic rhinitis, ameliorating a symptom means to reduce swelling of nasal mucosa, reduce rhinorrhea (runny nose), and/or reduce sneezing.

Furthermore, the present disclosure provides a plurality of methods of treating cancer in a mammalian subject in need thereof, comprising administration of a pharmaceutical composition in an amount sufficient to treat cancer in said subject. In certain embodiments, the present disclosure provides methods of treating cancer in a mammalian subject in need thereof, comprising administering an effective amount of a pharmaceutical composition by intratumoral delivery. In another aspect of the method, intratumoral delivery comprises injection of the pharmaceutical composition into at least one tumor lesion. In other aspects, treating cancer comprises inducing accumulation of tumor antigen-specific T cells in the injected tumor, for example, at greater numbers than had the pharmaceutical composition been administered at an extratumoral site. In other aspects, treating cancer comprises eliciting a systemic, tumor antigen-specific T cell response, including for example, a systemic, tumor antigen-specific T cell response of a higher magnitude than had the immunogenic composition been administered at an extratumoral site. In other aspects, treating cancer comprises eliciting a systemic tumor antigen-specific T cell response. In other aspects, treating cancer comprises reducing numbers of CD4+ FoxP3+ regulatory T cells in the injected tumor. In other aspects, the subject has one or more uninjected tumors (primary or metastatic lesions) in addition to the injected tumor, and treating cancer comprises one or more of the following: (a) reducing the number of uninjected tumors; (b) reducing the volume of uninjected tumors; and (c) retarding the growth of uninjected tumors. In some aspects, treating cancer comprises one or more of the following: (d) increasing the survival time of the subject; (e) reducing the volume of the injected tumor; and (f) retarding the growth of the injected tumor. In some embodiments, when the cancer is a solid tumor, "treating" cancer comprises shrinking the size of the solid tumor and any metastatic lesions, or otherwise reducing viable cancer cell numbers. In other embodiments, when the cancer is a solid tumor, "treating" cancer comprises delaying growth of the solid tumor and any metastatic lesions. In some aspects, treating cancer comprises increasing progression free survival or increasing time to progression. In other embodiments, the method further comprises administering an effective amount of a second, or additional, therapeutic agents to the subject. "Treating" cancer means to bring about a beneficial clinical result, such as causing remission or otherwise prolonging survival as compared to expected survival in the absence of treatment. In some preferred embodiments, "treating cancer" comprises assessing a patient's response to the immunogenic composition according to the Response Evaluation Criteria in Solid Tumors (RECIST version 1.1) as described (see, e.g., Eisenhauer et al 2009 *Eur J Cancer* 45:228-247). Response criteria to determine objective anti-tumor responses per RECIST include: complete response, partial response, progressive disease, and stable disease.

In some embodiments, the tumor is a sarcoma, a carcinoma, or an actinic keratosis. In some embodiments, the tumor is a lymphoma. In some embodiments, the cancer is selected from the group consisting of breast cancer, prostate cancer, lung cancer, colorectal cancer, uterine cancer, bladder cancer, melanoma, head and neck cancer, non-Hodgkin lymphoma, kidney cancer, ovarian cancer, pancreatic cancer, and thyroid cancer. In some embodiments, the cancer is a primary cancer of a site selected from the group consisting of oral cavity, digestive system, respiratory system, skin, breast, genital system, urinary system, ocular system, nervous system, endocrine system, and lymphoma.

In some embodiments, the method further comprises administering an effective amount of a second therapeutic agent to the subject. In some of these embodiments, the second therapeutic agent comprises a chemotherapeutic agent selected from the group consisting of actinomycin, afatinib, alectinib, asparaginase, azacitidine, azathioprine, bicalutamide, binimetinib, bleomycin, bortezomib, camptothecin, carboplatin, capecitabine, carmustine, certinib, cisplatin, chlorambucil, cobimetinib, crizotinib, cyclophosphamide, cytarabine, dabrafenib, dacarbazine, daunorubicin, docetaxel, doxifluridine, doxorubicin, encorafenib, erlotinib, epirubicin, epothilone, etoposide, fludarabine, flutamine, fluorouracil, gefitinib, gemcitabine, hydroxyurea, idarubicin, ifosfamide, imatinib, irinotecan, lapatinib, letrozole, mechlorethamine, mercaptopurine, methotrexate, mitomycin, mitoxantrone, octreotide, oxaliplatin, paclitaxel, pemetrexed, raltitrexed, sorafenib, sunitinib, tamoxifen, temozolomide, teniposide, tioguanine, topotecan, trametinib, valrubicin, vemurafenib, vinblastine, vincristine, vindesine, vinorelbine, and combinations thereof. In some embodiments, the second therapeutic agent comprises one or both of a BRAF inhibitor and a MEK inhibitor. In some embodiments, the second therapeutic agent comprises a epigenetic modulator selected from the group consisting of HDAC inhibitors (see e.g., voronistat [SAHA], romidepsin, entinostat, abexinostat, elinostat [CHR-3996], panobinostat, quisinostat [JNJ-26481585], 4SC-202, resminostat [SB939], pracinostat [CI-9940], and valproate), DNA methyltransferase inhibitors (see e.g., azacytidine, decitabine, zebularine, SGI-1027, RG-108, and sinfungin), and combinations thereof.

In some of these embodiments, the second therapeutic agent is an antagonist of an inhibitory immune checkpoint molecule, for example, an inhibitory immune checkpoint molecule selected from the group consisting of PD-1, PD-L1, PD-L2, CTLA-4 (CD152), LAG-3, TIM-3, TIGIT, IL-10, indoleamine 2,3-dioxygenase (IDO), P-selectin glycoprotein ligand-1 (PSGL-1), and TGF-beta. In some of these embodiments, the second therapeutic agent is an agonist of an immune stimulatory molecule. In some of these embodiments, the immune stimulatory molecule is selected from the group consisting of CD27, CD40, OX40 (CD134), GITR, 4-1BB (CD137), CD28, and ICOS (CD278). In some of these embodiments, the second therapeutic agent comprises an antibody, fragment, or derivative thereof. In some of these embodiments, the second therapeutic agent is an antagonist of an inhibitory immune checkpoint molecule and the second therapeutic agent comprises an antibody, fragment, or derivative thereof. In some embodiments, the method further comprises administering radiation therapy and/or administering an effective amount of a second therapeutic agent to the subject. In some of these embodiments, the effective amount of the immunogenic composition and the effective amount of the second therapeutic agent together result in an additive effect or better against the tumor. In some of these embodiments, the effective amount of the immunogenic composition and the effective amount of the second therapeutic agent together result in a synergistic effect against the tumor.

In some embodiments of the method, treating infectious disease or cancer does not result in development of flu-like symptoms of such severity that repeated administration of the immunogenic composition is contraindicated, wherein the flu-like symptoms comprise one or more of the group consisting of fever, headache, chills, myalgia, and fatigue.

In some embodiments, the present disclosure provides kits that comprise a pharmaceutical composition (e.g., a TLR7/8 agonist compound of formula (K), an excipient or excipients, and optionally an antigen) and a set of instructions relating to the use of the composition for the methods described herein. The pharmaceutical composition of the kits is packaged appropriately. If the pharmaceutical composition is a liquid or a suspension of nanoparticles, a silicon dioxide vial (e.g., SCHOTT Type I Plus®) with a rubber stopper (e.g., Exxpro halobutyl elastomer) and an aluminum crimp-top is typically used as the container-closure system. In some embodiments, the kits further comprise a device (e.g., syringe and needle) for administration of the pharmaceutical composition. In other embodiments, the kits further comprise a pre-filled syringe/needle system, autoinjectors, or needleless devices. The instructions relating to the use of the pharmaceutical composition generally include information as to dosage, schedule, and route of administration for the intended methods of use.

V. Examples

Although the present disclosure has been described in some detail by way of illustration and example for purposes of clarity and understanding, it will be apparent to those skilled in the art that certain changes and modifications may be practiced. Therefore, the following synthetic and biological examples should not be construed as limiting the scope of the present disclosure, which is delineated by the appended claims.

Synthetic Examples

Example S1: Synthesis of N-(4-((4-amino-2-butyl-1H-imidazo[4,5-c]quinolin-1-yl)methyl)benzyl)tetradecanamide (Compound No. 63-10)

Part A. Nitric acid (125 mL) was added to a slurry of quinoline-2,4-diol (50 g, 0.3 mole) in acetic acid (500 mL), and the reaction mixture was heated to 65° C. for three hours. The mixture was then cooled to 5-10° C. and the solid material collected by filtration, washed with cold water, and air dried. The resulting solid was then recrystallized from methanol and dried under vacuum to yield 58 g of 3-nitro-2,4-quinolinediol as a yellow solid.

Part B. Phosphorus oxychloride (150 mL) was added to 3-nitro-2,4-quinolinediol (58 g) under an argon atmosphere and heated to 95° C. for 4 hours. The mixture was then cooled to room temperature and poured onto crushed ice with constant stirring. The precipitated product was collected by filtration, washed with water, and dried under vacuum. The crude solid was purified by flash chromatography over silica gel using hexane/ethyl acetate to yield 35 g of 2,4-dichloro-3-nitroquinoline.

Part C. Tert-butyl (4-(aminomethyl)benzyl)carbamate (37.3 g, 0.16 mole, 1.1 eq) was added to a solution of 2,4-dichloro-3-nitroquinoline (35 g, 0.15 mole, 1.0 eq) in anhydrous dichloromethane (400 mL) and trimethylamine (16.0 g, 0.16 mole, 1.1 eq), and stirred overnight at room temperature. The solvents were removed under reduced pressure and the crude product was purified by flash chromatography over silica gel using hexane/ethyl acetate to yield 52 g of tert-butyl (4-(((2-chloro-3-nitroquinolin-4-yl)amino)methyl)benzyl)carbamate.

Part D. A solution of tert-butyl (4-(((2-chloro-3-nitroquinolin-4-yl)amino)methyl)benzyl)carbamate (52 g, 0.12 mole) in ethyl acetate (250 mL) was hydrogenated in the presence of 5% platinum on carbon (2.0 g) and sodium sulfate (52 g) using a Parr hydrogenation apparatus at 60 psi for 12 hours. The platinum catalyst and sodium sulfate were removed by filtering through a pad of Celite®, and the filtrate concentrated under reduced pressure. The product was further purified by flash chromatography over silica gel eluting with hexane/ethyl acetate to yield 32 g of tert-butyl (4-(((3-amino-2-chloroquinolin-4-yl)amino)methyl)benzyl)carbamate.

Part E. Pentanoyl chloride (9.7 mL, 81.5 mmol, 1.05 eq) was added slowly to a solution of tert-butyl (4-(((3-amino-2-chloroquinolin-4-yl)amino)methyl)benzyl)carbamate (32 g, 77.6 mmol, 1.0 eq) in anhydrous tetrahydrofuran (350 mL) and pyridine (30 mL) at 0-5° C. The reaction mixture was then warmed to room temperature and stirred for 12 hours. The solvents were removed under reduced pressure and then the solids were re-dissolved in ethyl acetate (400 mL), washed successively with water and saturated sodium bicarbonate (150 mL), and finally dried over anhydrous magnesium sulfate. The product was further purified by flash chromatography over silica gel, eluting with hexane/ethyl acetate to yield 22 g of tert-butyl (4-(((3-butyramido-2-chloroquinolin-4-yl)amino)methyl)benzyl)carbamate.

Part F. Water (80 mL) was added to a solution of tert-butyl (4-(((3-butyramido-2-chloroquinolin-4-yl)amino)methyl)benzyl)carbamate (22 g, 44.2 mmol, 1.0 eq) in ethanol (320 mL), followed by the addition of potassium carbonate (12.2 g, 88.4 mmol, 2.0 eq), and the mixture was heated with vigorous stirring to 55° C. for 16 hours. This reaction mixture was concentrated and the residue was partitioned between ethyl acetate (500 mL) and water (250 mL). The ethyl acetate layer was then washed with water (100 mL), dried over anhydrous magnesium sulfate, and concentrated under reduced pressure. The product was further purified by flash chromatography over silica gel, eluting with hexane/ethyl acetate to yield 15.4 g of tert-butyl (4-((2-butyl-4-chloro-1H-imidazo[4,5-c]quinolin-1-yl)methyl)benzyl)carbamate.

Part G. Tert-butyl (4-((2-butyl-4-chloro-1H-imidazo[4,5-c]quinolin-1-yl)methyl)benzyl)carbamate (15.4 g, 32.2 mmol, 1 eq) was dissolved in anhydrous dimethyl formamide (125 mL), and then sodium azide (8.4 g, 128.6 mmol, 4 eq) was added to this solution. The resulting suspension was degassed and stirred under argon atmosphere at 110-115° C., with the reaction progress being monitored by reverse-phase HPLC analysis. After 18 hours, the reaction mixture was cooled to room temperature, poured into cold water (500 mL), and extracted with ethyl acetate (3×100 mL). The combined extract was washed with water (2×75 mL), dried over magnesium sulfate, filtered through Celite, and concentrated under reduced pressure to yield an off-white solid. This solid was further worked up by re-crystallization with 1:1 ethyl/hexane to yield 12.5 g of tert-butyl (4-((4-azido-2-butyl-1H-imidazo[4,5-c]quinolin-1-yl)methyl)benzyl)carbamate.

Part H. Tert-butyl (4-((4-azido-2-butyl-1H-imidazo[4,5-c]quinolin-1-yl)methyl)benzyl)carbamate (12.5 g, 25.7 mmol) was added to concentrated hydrochloric acid (65 mL), and 10% platinum on carbon (3.0 g) was added to this suspension. This reaction mixture was subjected to hydrogenation at 65 psi, with the reaction progress being monitored by reverse-phase HPLC analysis. After 6 days, the catalyst was filtered off and the filtered cake was washed with water (2×25 mL). The cake was cooled in an ice bath, ice cold 1N sodium hydroxide was added drop wise while stirring vigorously until the pH reached 8.5, and the material was extracted with dichloromethane containing 5% methanol (4×75 mL). The combined extract was dried over magnesium sulfate, filtered, and concentrated under reduced pressure. The residue was purified on a silica gel column using 8% methanol/dichloromethane containing 1% aqueous ammonia to yield 5.3 g of 1-(4-(aminomethyl)benzyl)-2-butyl-1H-imidazo[4,5-c]quinolin-4-amine.

Part I. Myristic acid (27.4 mg, 0.12 mmol, 1.2 eq) and trimethylamine (0.2 mL) were added to a solution of 1-(4-(aminomethyl)benzyl)-2-butyl-1H-imidazo[4,5-c]quinolin-4-amine (34 mg, 0.1 mmol, 1.0 eq) in anhydrous dimethylformamide (2 mL), and the slurry was mixed for 5 minutes followed by the addition of HBTU (47.4 mg, 0.125 mmol, 1.25 eq). This reaction mixture was further stirred for 2 hours under argon atmosphere. The solvent was removed under reduced pressure, the residue dissolved in ethyl acetate (30 mL) and washed with water (2×10 mL), then dried using magnesium sulfate and concentrated under vacuum. This product was purified using column chromatography (6% methanol/dichloromethane) to yield 35 mg of N-(4-((4-amino-2-butyl-1H-imidazo[4,5-c]quinolin-1-yl)methyl)benzyl)tetradecanamide (Compound No. 63-10). Product purity was assessed to be ~98% by reverse-phase HPLC, the intended synthetic mass of 569.8 was confirmed by LC/MS, and the intended synthetic structure confirmed by 300 MHz proton NMR (CDCl$_3$): δ 7.98 (d, J=8.1 Hz, 1H), 7.75 (d, J=8.4 Hz, 1H), 7.67 (t, J=8.4 Hz, 1H), 7.40 (t, J=7.5 Hz, 1H), 7.30 (d, J=8.1 Hz, 2H), 7.06 (d, J=8.1 Hz, 2H), 5.95 (s, 2H), 4.33 (s, 2H), 3.74 (s, 2H), 3.01 (t, J=7.8 Hz, 2H), 2.20 (t, J=7.5 Hz, 2H), 1.82-1.9 (m, 2H), 1.42-1.70 (m, 4H), 1.26-1.48 (m, 20H), 0.85-1.05 (m, 6H).

Example S2: Synthesis of 2-butyl-1-(4-((pentylamino)methyl)benzyl)-1H-imidazo[4,5-c]quinolin-4-amine (Compound No. 63-17)

Parts A-H were the same as in Example S1.
Part I. Valeric acid (34 mg, 0.33 mmol, 1.2 eq) and trimethylamine (140 mg, 1.39 mmol, 5.0 eq) were added to a solution of 1-(4-(aminomethyl)benzyl)-2-butyl-1H-imidazo[4,5-c]quinolin-4-amine (100 mg, 0.28 mmol, 1.0 eq) in anhydrous dimethylformamide (2 mL), and the slurry was mixed for 5 minutes followed by the addition of HBTU (131 mg, 0.34 mmol, 1.25 eq). This reaction mixture was further stirred for 2 hours under an argon atmosphere. The reaction was diluted with ethyl acetate (100 mL) and washed with water (3×30 mL), then dried using magnesium sulfate and concentrated under vacuum. The crude residue was taken up in ethyl acetate and methanol and purified using column chromatography (6% methanol/dichloromethane) to yield 160 mg of N-(4-((4-amino-2-butyl-1H-imidazo[4,5-c]quinolin-1-yl)methyl)benzyl)pentanamide.

Part J. A solution of borane-dimethyl sulfide complex (2.0 M, 1.5 mL, excess) was added to solution of N-(4-((4-amino-2-butyl-1H-imidazo[4,5-c]quinolin-1-yl)methyl)benzyl)pentanamide (127 mg, 0.28 mmol, 1.0 eq) in anhydrous tetrahydrofuran (5 mL) at room temperature, and the reaction mixture was heated to reflux for 12 hours. The mixture was cooled to ambient temperature, quenched with 3N HCl (1 mL), and stirred for 4 hours. The pH of the reaction mixture was made alkaline by the addition 2N sodium hydroxide and the product was extracted with dichloromethane (20 mL×10). The combined organic layers were concentrated under reduced pressure and the residue purified by flash chromatography with 6% methanol/dichloromethane as an eluent to yield 24 mg of 2-butyl-1-(4-((pentylamino)methyl)benzyl)-1H-imidazo[4,5-c]quinolin-4-amine (Compound No. 63-17). Product purity was assessed to be ~96% by reverse-phase HPLC, the intended synthetic mass of 429.6 was confirmed by LC/MS, and the intended synthetic structure confirmed by 300 MHz proton NMR (CDCl$_3$): δ 7.8 (d, J=8.4 Hz, 1H), 7.70 (d, J=8.5 Hz, 1H), 7.45 (t, J=8.4, 1H), 7.34 (d, J=8.5 Hz, 2H), 7.10 (t, J=8.4 Hz, 1H), 7.02 (d, J=8.3 Hz, 2H), 5.70 (br s, 4H), 3.80 (s, 2H), 2.89 (t, J=7.6 Hz, 2H), 2.62 (t, J=7.2 Hz, 2H), 1.75-1.84 (m, 2H), 1.2-1.75 (m, 8H), 0.65-1.0 (m, 6H).

Example S3: Synthesis of 2-butyl-1-(4-(((2-cyclopropylethyl)amino)methyl)benzyl)-1H-imidazo[4,5-c]quinolin-4-amine (Compound No. 63-33)

Parts A-H were the same as in Example S1.
Part I. Cyclopropylacetic acid (33 mg, 0.33 mmol, 1.2 eq) and trimethylamine (140 mg, 1.39 mmol, 5.0 eq) were added to a solution of 1-(4-(aminomethyl)benzyl)-2-butyl-1H-imidazo[4,5-c]quinolin-4-amine (100 mg, 0.28 mmol, 1.0 eq) in anhydrous dimethylformamide (2 mL), and the slurry was mixed for 5 minutes followed by the addition of HBTU (131 mg, 0.34 mmol, 1.25 eq). This reaction mixture was further stirred for 2 hours under an argon atmosphere. The reaction was diluted with ethyl acetate (100 mL) and washed with water (3×30 mL), then dried using magnesium sulfate and concentrated under vacuum. The crude residue was taken up in ethyl acetate and methanol, and purified using column chromatography (6% methanol/dichloromethane) to yield 140 mg of N-(4-((4-amino-2-butyl-1H-imidazo[4,5-c]quinolin-1-yl)methyl)benzyl)-2-cyclopropylacetamide (Compound No. 63-34).

Part J. A solution of borane-dimethyl sulfide complex (2.0 M, 1.5 mL, excess) was added to solution of N-(4-((4-amino-2-butyl-1H-imidazo[4,5-c]quinolin-1-yl)methyl)benzyl)-2-cyclopropylacetamide (123 mg, 0.28 mmol, 1.0 eq) in anhydrous tetrahydrofuran (5 mL) at room temperature, and the reaction mixture was heated to reflux for 12 hours. The mixture was cooled to ambient temperature, quenched with 3N HCl (1 mL), and stirred for 4 hours. The pH of the reaction mixture was made alkaline by the addition 2N sodium hydroxide and the product was extracted with dichloromethane (20 mL×10). The combined organic layers were concentrated under reduced pressure and the residue purified by flash chromatography with 6% methanol/dichloromethane as an eluent to yield 28 mg of 2-butyl-1-(4-(((2-cyclopropylethyl)amino)methyl)benzyl)-1H-imidazo[4,5-c]quinolin-4-amine (Compound No. 63-33). Product purity was assessed to be 97% by reverse-phase HPLC, the intended synthetic mass of 427.6 was confirmed by LC/MS, and the intended synthetic structure confirmed by 400 MHz $^1$H NMR (CDCl$_3$): δ 7.80 (dd, J=8.5, 1.0 Hz, 1H), 7.70 (dd, J=8.3, 1.1 Hz, 1H), 7.42 (m, J=8.4. 7.0, 1.4 Hz, 1H), 7.29 (as, 1H), 7.25 (as, 1H), 7.10 (m, J=8.2, 7.1, 1.3 Hz, 1H), 7.00 (d, J=8.4 Hz, 2H), 5.92 (bs, 2H), 5.69 (s, 2H), 3.75 (s, 2H), 2.86 (dd, J=8.0 Hz, 2H), 2.68 (dd, J=8.0 Hz, 2H), 1.82-1.74 (m, 2H), 1.45-1.36 (m, 4H), 0.91 (t, J=7.8 Hz, 3H), 0.91-0.85 (m, 1H), 0.68-0.60 (m, 1H), 0.42-0.37 (m, 2H), 0.04-0.00 (m, 2H).

Example S4: Synthesis of Other Exemplary Compounds

Exemplary N-alkyl compounds of formula (J-1) were synthesized using similar procedures as for Compound No. 63-33. Using techniques known to those skilled in the art, the calculated partitioning coefficient (c Log P) for the exemplary compounds was determined using the Molecular Descriptors algorithm in the Molecular Operating Environment software (see e.g., Labute P, The Derivation and Applications of Molecular Descriptors Based Upon (Approximate) Surface Area; in *Chemoinformatics: Concepts, Methods, and Tools for Drug Discovery*, J. Bajorath ed.

2003). $^1$H NMR and mass spectrometry data are detailed below for certain compounds of the present invention, and Table 3 provides purity data and c Log P values.

TABLE 3

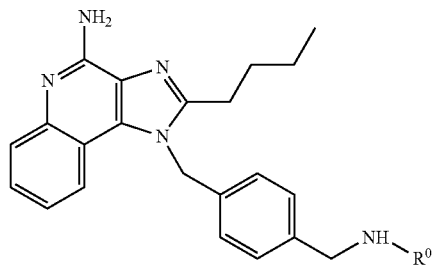

(J-1)

| Compound No. | Formula (J-1), R⁰ | % Purity (HPLC) | cLogP |
|---|---|---|---|
| 63-33 | —(CH₂)₂-cyclopropyl | 95 | 3.9 |
| 63-35 | —(CH₂)₂-cyclobutyl | 97 | 4.4 |
| 63-36 | —(CH₂)₂-cyclopentyl | 88 | 4.9 |
| 63-39 | —(CH₂)-2-methylcyclopropyl | 90 | ND |
| 63-40 | —(CH₂)-2,2-dimethylcyclopropyl | 93 | ND |
| 63-42 | —(CH₂)₂-1-methylcyclopropyl | 90 | ND |
| 63-43 | —(CH₂)₃-cyclopropyl | 95 | ND |
| 63-46 | —(CH₂)-3-methylcyclobutyl | 93 | ND |

ND = not determined.

Compound No. 63-33: $^1$H NMR (CDCl₃, 400 MHz): δ 7.80 (dd, J=8.5, 1.0 Hz, 1H), 7.70 (dd, J=8.3, 1.1 Hz, 1H), 7.42 (m, J=8.4. 7.0, 1.4 Hz, 1H), 7.29 (as, 1H), 7.25 (as, 1H), 7.10 (m, J=8.2, 7.1, 1.3 Hz, 1H), 7.00 (d, J=8.4 Hz, 2H), 5.92 (bs, 2H), 5.69 (s, 2H), 3.75 (s, 2H), 2.86 (dd, J=8.0 Hz, 2H), 2.68 (dd, J=8.0 Hz, 2H), 1.82-1.74 (m, 2H), 1.45-1.36 (m, 4H), 0.91 (t, J=7.8 Hz, 3H), 0.91-0.85 (m, 1H), 0.68-0.60 (m, 1H), 0.42-0.37 (m, 2H), 0.04-0.00 (m, 2H). Mass Spec: m/z 428.6 (M+1).

Compound No. 63-35: $^1$H NMR (CDCl₃, 300 MHz): δ 7.8 (d, J=8.4 Hz, 1H), 7.70 (d, J=8.5 Hz, 1H), 7.45 (t, J=8.4, 1H), 7.34 (d, J=8.5 Hz, 2H), 7.10 (t, J=8.4 Hz, 1H), 7.02 (d, J=8.3 Hz, 2H), 5.72 (s, 2H), 3.85 (s, 2H), 2.89 (t, J=7.6 Hz, 2H), 2.60 (t, J=7.2 Hz, 2H), 2.20-2.35 (m, 1H), 1.8-2.1 (m, 2H), 1.65-1.8 (m, 6H), 1.4-1.55 (m, 4H), 0.94 (t, J=7.3 Hz, 3H). Mass Spec m/z 442.9 (M+1).

Compound No. 63-36: $^1$H NMR (CDCl₃, 300 MHz): δ 7.8 (d, J=8.4 Hz, 1H), 7.70 (d, J=8.5 Hz, 1H), 7.45 (t, J=8.4, 1H), 7.34 (d, J=8.5 Hz, 2H), 7.10 (t, J=8.4 Hz, 1H), 7.02 (d, J=8.3 Hz, 2H), 5.72 (s, 2H), 3.80 (br s, 4H), 2.89 (t, J=7.6 Hz, 2H), 2.62 (t, J=7.2 Hz, 2H), 1.62-1.84 (m, 7H), 1.0-1.20 (m, 1H), 0.94 (t, J=7.3 Hz, 3H). Mass Spec: m/z 456.4 (M+1).

Compound No. 63-39: $^1$H NMR (CD₃OD, 300 MHz): δ 7.80 (d, J=8.1 Hz, 1H), 7.67 (d, J=8.4 Hz, 1H), 7.30-7.48 (m, 3H), 7.05-7.14 (m, 3H), 5.88 (s, 2H), 3.81 (s, 2H), 2.89 (t, J=7.5, 15.6 Hz, 2H), 2.44-2.55 (m, 2H), 1.70-1.85 (m, 2H), 1.35-1.55 (m, 3H), 1.02 (s, J=6 Hz, 3H), 0.94 (t, J=7.5, 14.7 Hz, 3H), 0.50-0.75 (m, 2H), 0.20-0.35 (m, 2H). Mass Spec: m/z 428.4 [M+1].

Compound No. 63-40: $^1$H NMR (CDCl₃, 300 MHz): δ 7.82 (d, J=8.1 Hz, 1H), 7.73 (d, J=8.4 Hz, 1H), 7.45 (t, J=7.5, 15.0 Hz, 1H), 7.29 (d, J=8.4 Hz, 2H), 7.15 (t, J=7.5, 15.0 Hz, 1H), 7.03 (d, J=8.4 Hz, 2H), 5.73 (s, 2H), 5.54 (s, 2H), 3.78 (s, 2H), 2.50-2.70 (m, 2H), 1.75-1.80 (m, 2H), 1.40-1.55 (m, 2H), 1.04 (s, 3H), 1.02 (s, 3H), 0.94 (t, J=7.5, 14.7 Hz, 3H), 0.7-0.8 (m, 1H), 0.4-0.5 (m, 1H), 0.1-0.05 (m, 1H). Mass Spec: m/z 442.5 [M+1].

Compound No. 63-42: $^1$H NMR (CDCl₃, 300 MHz): δ 7.80 (d, J=8.1 Hz, 1H), 7.71 (d, J=8.4 Hz, 1H), 7.43 (t, J=7.5, 15.0 Hz, 1H), 7.31 (d, J=8.4 Hz, 2H), 7.14 (t, J=7.5, 15.0 Hz, 1H), 7.01 (d, J=8.4 Hz, 2H), 5.71 (s, 2H), 3.76 (s, 2H), 2.89 (t, J=7.5, 15.6 Hz, 2H), 2.70 (t, J=7.2, 15.0 Hz, 2H), 1.77-1.92 (m, 2H), 1.70-1.84 (m, 4H), 0.98 (s, 3H), 0.94 (t, J=7.5, 14.7 Hz, 3H), 0.18-0.35 (m, 4H). Mass Spec: m/z 442.5 [M+1].

Compound No. 63-43: $^1$H NMR (CDCl₃, 300 MHz): δ 7.80 (d, J=8.1 Hz, 1H), 7.71 (d, J=8.4 Hz, 1H), 7.43 (t, J=7.5, 15.0 Hz, 1H), 7.25-7.31 (m, 2H), 7.14 (t, J=7.5, 15.0 Hz, 1H), 7.01 (d, J=8.4 Hz, 2H), 5.71 (s, 2H), 5.59 (s, 2H), 3.75 (s, 2H), 2.88 (br t, 2H), 2.63 (t, J=7.2, 14.1 Hz, 3H), 0.55-0.72 (m, 1H), 0.4 (br d, 2H), 0.01 (d, J=4.5 Hz, 2H). Mass Spec: m/z 442.5 [M+1].

Compound No. 63-46: $^1$H NMR (CDCl₃, 300 MHz): δ 7.81 (d, J=8.1 Hz, 1H), 7.74 (d, J=8.4 Hz, 1H), 7.45 (t, J=7.5, 15.0 Hz, 1H), 7.29 (d, J=8.4 Hz, 2H), 7.15 (t, J=7.5, 15.0 Hz, 1H), 7.03 (d, J=8.4 Hz, 2H), 5.73 (s, 2H), 5.51 (s, 2H), 3.74 (s, 2H), 2.86 (t, J=7.5, 15.6 Hz, 2H), 2.60-2.7 (m, 2H), 2.1-2.4 (m, 3H), 1.6-1.85 (m, 4H), 1.40-1.55 (m, 2H), 0.95-1.15 (m, 5H), 0.94 (t, J=7.5, 14.7 Hz, 3H). Mass Spec: m/z 442.4 [M+1].

Example S5: Synthesis of 2-butyl-1-(4-(((cyclopropylmethyl)amino)methyl)benzyl)-1H-imidazo[4,5-c]quinolin-4-amine (Compound No. 63-38)

Part A. N, N-diisopropylcarbodiimide (272 mg, 2.15 mmol) was added to a solution of cyclopropane carboxylic acid (172 mg, 2.0 mmol) and pentafluorophenol (387 mg, 2.1 mmol) in dichloromethane (4 mL), in presence of catalytic amounts of N,N-dimethylaminopyridine (12 mg), and stirred overnight at room temperature. This mixture was then diluted with ether (20 mL), the precipitated urea removed by filtration, and the filtrate concentrated to obtain crude product. This crude product was suspended in 1% ethyl acetate/hexane and any residual precipitated urea was again removed by filtration. The resultant filtrate was concentrated under reduced pressure to yield 440 mg of the desired (2,3,4,5,6-pentafluorophenyl)-cyclopropane carboxylate product.

Part B. Compound No. 63-00 (80 mg, 0.22 mmol) was added to a solution of (2,3,4,5,6-pentafluorophenyl)-cyclopropane carboxylate (61 mg, 0.24 mmol) in dichloromethane (3 mL) in presence of triethylamine (45 mg, 0.44 mmol), and stirred for 2 hours at room temperature. The reaction mixture was then concentrated under reduced pressure and purified by flash chromatography, eluting with 3-8% methanol/dichloromethane containing 1% aqueous ammonia, to obtain 78 mg of N-(4-((4-amino-2-butyl-1H-imidazo[4,5-c]quinolin-1-yl)methyl)benzyl)cyclopropanecarboxamide as an off-white solid.

Part C. N-(4-((4-amino-2-butyl-1H-imidazo[4,5-c]quinolin-1-yl)methyl)benzyl) cyclopropanecarboxamide (78 mg) was reduced with borane dimethyl sulfide complex (3.5 eq) at 55° C. for 12 hours. The reaction was then cooled to room temperature, carefully quenched with 1 M HCl (excess), and stirred for an additional 3 hours at 55° C. The reaction was cooled to room temperature and diluted with water (10 mL), and then extracted with dichloromethane (10 mL) to remove impurities. The pH of the reaction mixture was adjusted to 8.0 by adding an ice-cold 1M NaOH solution, extracted with dichloromethane (3×10 mL), dried over MgSO₄, and concentrated under reduced pressure to yield an off-white solid. Upon recrystallization with 9:1 ethyl acetate/hexane the reaction yielded 27 mg of 2-butyl-1-(4-((((cyclopropylmethyl)amino)methyl)benzyl)-1H-imidazo[4,5-c]quinolin-4-amine (Compound No. 63-38). Product purity was assessed to be 96% pure by reverse-phase HPLC at 254 nm, the intended synthetic mass of 413.3 Daltons was confirmed by LC/MS, and the intended synthetic structure confirmed by 300 MHz $^1$H NMR (CD$_3$OD): δ 7.80 (d, J=8.1 Hz, 1H), 7.67 (d, J=8.4 Hz, 1H), 7.38-7.48 (m, 3H), 7.07-7.20 (m, 3H), 5.92 (s, 2H), 3.97 (s, 2H), 3.0 (t, J=7.8, 15.3 Hz, 2H), 2.66 (2, J=7.2 Hz, 2H), 1.78-1.90 (m, 2H), 1.40-1.60 (m, 2H), 1.0 (t, J=7.5 Hz, 3H), 0.5-0.6 (m, 2H), 0.2-0.3 (m, 2H).

Example S6: Synthesis of 2-butyl-1-(4-((((1-methylcyclobutyl)methyl)amino)methyl)benzyl)-1H-imidazo[4,5-c]quinoline-4-amine (Compound No. 63-45)

Part A. N, N-diisopropylcarbodiimide (76 mg, 0.6 mmol) was added to a solution of 1-methylcyclobutane carboxylic acid (57 mg, 0.5 mmol) and pentafluorophenol (94 mg, 0.52 mmol) in dichloromethane (3 mL), in presence of catalytic amount of N,N-dimethylaminopyridine (6 mg), and stirred overnight at room temperature. This mixture was then diluted with ether (20 mL), the precipitated urea removed by filtration, and the filtrate concentrated to obtain crude product. This crude product was suspended in 1% ethyl acetate/hexane and any residual precipitated urea was again removed by filtration. The resultant filtrate was concentrated under reduced pressure to yield 126 mg of the desired (2,3,4,5,6-pentafluorophenyl)-1-methylcyclobutane carboxylate product.

Part B. Compound No. 63-00 (84 mg, 0.23 mmol) was added to a solution of (2,3,4,5,6-pentafluorophenyl)-1-methylcyclobutane carboxylate (72 mg, 0.26 mmol) in dichloromethane (3 mL) in presence of triethylamine (48 mg, 0.47 mmol), and stirred for 2 hours at room temperature. The reaction mixture was then concentrated under reduced pressure and the residue washed with 5% ethyl acetate/hexane. The residue was dissolved in dichloromethane (15 mL), washed with 1M HCl followed by water (20 mL), dried over magnesium sulfate, filtered and concentrated under reduced pressure to yield 88 mg of N-(4-((4-amino-2-butyl-1H-imidazo[4,5-c]quinolin-1-yl)methyl)benzyl)-1-methylcyclobutane-1-carboxamide as off white solid.

Part C. N-(4-((4-amino-2-butyl-1H-imidazo[4,5-c]quinolin-1-yl)methyl)benzyl)-1-methylcyclobutane-1-carboxamide (88 mg) was reduced with borane dimethyl sulfide complex (3.5 eq) at 55° C. for 12 hours. The reaction was then cooled to room temperature, carefully quenched with 2 M HCl (excess), and stirred for an additional 3 hours at 55° C. The reaction was cooled to room temperature and diluted with water (10 mL), then extracted with dichloromethane (10 mL) to remove impurities. The pH of the reaction mixture was adjusted to 8.0 by adding an ice-cold 1M NaOH solution, extracted with dichloromethane (3×10 mL), dried over MgSO$_4$, and concentrated under reduced pressure to yield an off-white solid. Upon recrystallization with 9:1 ethyl acetate/hexane the reaction yielded 32 mg of 2-butyl-1-(4-((((1-methylcyclobutyl)methyl)amino)methyl)benzyl)-1H-imidazo[4,5-c]quinolin-4-amine (Compound No. 63-45). Product purity was assessed to be 96% pure by reverse-phase HPLC at 254 nm, the intended synthetic mass of 441.3 Daltons was confirmed by LC/MS, and the intended synthetic structure confirmed by 300 MHz $^1$H NMR (CDCl$_3$): δ 7.80 (d, J=8.1 Hz, 1H), 7.71 (d, J=8.4 Hz, 1H), 7.43 (t, J=7.5, 15.0 Hz, 1H), 7.31 (d, J=8.4 Hz, 2H), 7.14 (t, J=7.5, 15.0 Hz, 1H), 7.01 (d, J=8.4 Hz, 2H), 5.71 (s, 2H), 5.52 (s, 2H), 3.78 (s, 2H), 2.89 (t, J=7.5, 15.6 Hz, 2H), 2.52 (s, 2H), 1.6-1.88 (m, 8H), 1.35-1.60 (m, 2H), 1.12 (s, 3H), 0.94 (t, J=7.5, 14.7 Hz, 3H).

Example S7: Synthesis of 2-butyl-1-(4-(((cyclobutylmethyl)amino)methyl)benzyl)-1H-imidazo[4,5-c]quinoline-4-amine (Compound No. 63-44)

Part A. N, N-diisopropylcarbodiimide (127 mg, 1.0 mmol) was added to a solution of cyclobutane carboxylic acid (106 mg, 0.93 mmol) and pentafluorophenol (175 mg, 0.97 mmol) in dichloromethane (3 mL), in presence of catalytic amount of N,N-dimethylaminopyridine (12 mg), and stirred overnight at room temperature. This mixture was then diluted with ether (20 mL), the precipitated urea removed by filtration, and the filtrate concentrated to obtain crude product. This crude product was suspended in 1% ethyl acetate/hexane and any residual precipitated urea was again removed by filtration. The resultant filtrate was concentrated under reduced pressure to yield 126 mg of the desired (2,3,4,5,6-pentafluorophenyl)cyclobutane carboxylate product.

Part B. Compound No. 63-00 (62 mg, 0.17 mmol) was added to a solution of (2,3,4,5,6-pentafluorophenyl)cyclobutane carboxylate (50 mg, 0.18 mmol) in dichloromethane (3 mL), in presence of triethylamine (35 mg, 0.34 mmol), and stirred for 2 hours at room temperature. The reaction mixture was then concentrated under reduced pressure and the residue washed with 5% ethyl acetate/hexane. The residue was dissolved in dichloromethane (15 mL), washed with 1M HCl followed by water (20 mL), dried over magnesium sulfate, filtered and concentrated under reduced pressure to yield 85 mg of N-(4-((4-amino-2-butyl-1H-imidazo[4,5-c]quinolin-1-yl)methyl)benzyl)cyclobutanecarboxamide as an off-white solid.

Part C. N-(4-((4-amino-2-butyl-1H-imidazo[4,5-c]quinolin-1-yl)methyl)benzyl)cyclobutanecarboxamide (85 mg) was reduced with borane dimethyl sulfide complex (3.5 eq) at 55° C. for 12 hours. The reaction was then cooled to room temperature, carefully quenched with 2 M HCl (excess), and stirred for an additional 3 hours at 55° C. The reaction was cooled to room temperature and diluted with water (10 mL), then extracted with dichloromethane (10 mL) to remove impurities. The pH of the reaction mixture was adjusted to 8.0 by adding an ice-cold 1M NaOH solution, extracted with dichloromethane (3×10 mL), dried over MgSO$_4$, and concentrated under reduced pressure to yield an off-white solid. Upon recrystallization with 9:1 ethyl acetate/hexane the reaction yielded 21 mg of 2-butyl-1-(4-(((cyclobutylmethyl)amino)methyl)benzyl)-1H-imidazo[4,5-c]quinolin-4-amine (Compound No. 63-44). Product purity was assessed to be 95% pure by reverse-phase HPLC at 254 nm, the intended synthetic mass of 427.3 Daltons was confirmed by LC/MS, and the intended synthetic structure confirmed by 300 MHz $^1$H NMR (CDCl$_3$): δ 7.80 (d, J=8.1 Hz, 1H), 7.73 (d, J=8.4 Hz, 1H), 7.45 (t, J=7.5, 15.0 Hz, 1H), 7.29 (d, J=8.4 Hz, 2H), 7.15 (t, J=7.5, 15.0 Hz, 1H), 7.03 (d, J=8.4 Hz, 2H), 5.72 (s, 2H), 5.51 (s, 2H), 3.74 (s, 2H), 2.89 (t, J=7.5, 15.6 Hz, 2H), 2.62 (d, J=7.2 Hz, 2H), 2.40-2.58 (m, 1H), 1.75-2.15 (m, 7H), 1.60-1.70 (m, 2H), 1.35-1.50 (m, 2H), 0.94 (t, J=7.5, 14.7 Hz, 3H).

Example S8: Synthesis of 2-butyl-1-(4-(((2-cyclobutyl-2-methylpropyl)amino)methyl)benzyl)-1H-imidazo[4,5-c]quinolin-4-amine (Compound No. 63-47)

Part A. N, N-diisopropylcarbodiimide (113 mg, 0.89 mmol) was added to a solution of 3-cyclobutyl-3-methylbutan-2-one (70 mg, 0.5 mmol) and pentafluorophenol (108 mg, 0.59 mmol) in dichloromethane (3 mL), in presence of catalytic amount of N,N-dimethylaminopyridine (11 mg), and stirred overnight at room temperature. This mixture was then diluted with ether (20 mL), the precipitated urea removed by filtration, and the filtrate concentrated to obtain crude product. This crude product was suspended in 1% ethyl acetate/hexane and any residual precipitated urea was again removed by filtration. The resultant filtrate was concentrated under reduced pressure to yield 141 mg of the desired (2,3,4,5,6-pentafluorophenyl)-2-cyclobutyl-2-methyl-propanoate product.

Part B. Compound No. 63-00 (60 mg, 0.17 mmol) was added to a solution of (2,3,4,5,6-pentafluorophenyl)-2-cyclobutyl-2-methyl-propanoate (54 mg, 0.18 mmol) in dichloromethane (3 mL), in presence of triethylamine (34 mg, 0.34 mmol), and stirred at reflux for 3 days. The reaction mixture was then cooled to room temperature, concentrated under reduced pressure, and the residue washed with 5% ethyl acetate/hexane. The washed residue was dissolved in dichloromethane (15 mL), washed with 1M HCl followed by water (20 mL), dried over magnesium sulfate, filtered, and concentrated under reduced pressure to yield 67 mg of N-(4-((4-amino-2-butyl-1H-imidazo[4,5-c]quinolin-1-yl)methyl)benzyl)-2-cyclobutyl-2-methylpropanamide as an off-white solid.

Part C. N-(4-((4-amino-2-butyl-1H-imidazo[4,5-c]quinolin-1-yl)methyl)benzyl)-2-cyclobutyl-2-methylpropanamide (67 mg) was reduced with borane dimethyl sulfide complex (3.5 eq) at 55° C. for 12 hours. The reaction was then cooled to room temperature, carefully quenched with 2 M HCl (excess), and stirred for an additional 3 hours at 55° C. The reaction was cooled to room temperature and diluted with water (10 mL), and then extracted with dichloromethane (10 mL) to remove impurities. The pH of the reaction mixture was adjusted to 8.0 by adding an ice-cold 1M NaOH solution, extracted with dichloromethane (3×10 mL), dried over $MgSO_4$, and concentrated under reduced pressure to yield an off-white solid. Upon recrystallization with 9:1 ethyl acetate/hexane the reaction yielded 13 mg of 2-butyl-1-(4-(((2-cyclobutyl-2-methylpropyl)amino)methyl)benzyl)-1H-imidazo[4,5-c]quinolin-4-amine (Compound No. 63-47). Product purity was assessed to be 92% pure by reverse-phase HPLC at 254 nm, the intended synthetic mass of 469.3 Daltons was confirmed by LC/MS, and the intended synthetic structure confirmed by 300 MHz $^1$H NMR ($CDCl_3$): δ 7.80 (d, J=8.1 Hz, 1H), 7.71 (d, J=8.4 Hz, 1H), 7.43 (t, J=7.5, 15.0 Hz, 1H), 7.31 (d, J=8.4 Hz, 2H), 7.14 (t, J=7.5, 15.0 Hz, 1H), 7.01 (d, J=8.4 Hz, 2H), 6.60 (br s, 1H), 5.73 (s, 2H), 3.74 (br s, 4H), 2.90 (t, J=7.5, 15.6 Hz, 2H), 2.35 (s, 2H), 1.20-1.8 (m, 10H), 0.94 (t, J=7.5, 14.7 Hz, 3H), 0.90 (s, 6H).

Example S9: Synthesis of 2-butyl-1-(4-(((2-cyclopropyl-2-methylpropyl)amino)methyl)benzyl)-1H-imidazo[4,5-c]quinoline-4-amine (Compound No. 63-41)

Part A. N, N-diisopropylcarbodiimide (127 mg, 1.0 mmol) was added to a solution of 2-cyclopropyl-2-methyl-propanoic acid (106 mg, 0.93 mmol) and pentafluorophenol (175 mg, 0.97 mmol) in dichloromethane (3 mL), in the presence of catalytic amounts of N,N-dimethylaminopyridine (12 mg), and stirred overnight at room temperature. This mixture was then diluted with ether (20 mL), the precipitated urea removed by filtration, and the filtrate concentrated to obtain crude product. This crude product was suspended in 1% ethyl acetate/hexane and any residual precipitated urea was again removed by filtration. The resultant filtrate was concentrated under reduced pressure to yield 130 mg of the desired (2,3,4,5,6-pentafluorophenyl)-2,2-dimethylcyclopropanecarboxylate product.

Part B. Compound No. 63-00 (62 mg, 0.17 mmol) was added to a solution of (2,3,4,5,6-pentafluorophenyl)-2,2-dimethylcyclopropanecarboxylate (50 mg, 0.18 mmol) in dichloromethane (3 mL), in presence of triethylamine (35 mg, 0.34 mmol), and stirred for 2 hours at room temperature. The reaction mixture was then concentrated under reduced pressure and the residue washed with 5% ethyl acetate/hexane. The washed residue was dissolved in dichloromethane (15 mL), washed with 1M HCl followed by water (20 mL), dried over magnesium sulfate, filtered and concentrated under reduced pressure to yield 85 mg of N-(4-((4-amino-2-butyl-1H-imidazo[4,5-c]quinolin-1-yl)methyl)benzyl)-2-cyclopropyl-2-methylpropanamide as an off-white solid.

Part C. N-(4-((4-amino-2-butyl-1H-imidazo[4,5-c]quinolin-1-yl)methyl)benzyl)-2-cyclopropyl-2-methylpropanamide (85 mg) was reduced with borane dimethyl sulfide complex (3.5 eq) at 55° C. for 12 hours. The reaction was then cooled to room temperature, carefully quenched with 2 M HCl (excess), and stirred for an additional 3 hours at 55° C. The reaction was cooled to room temperature and diluted with water (10 mL), and then extracted with dichloromethane (10 mL) to remove impurities. The pH of the reaction mixture was adjusted to 8.0 by adding an ice-cold 1M NaOH solution, extracted with dichloromethane (3×10 mL), dried over $MgSO_4$, and concentrated under reduced pressure to yield an off-white solid. Upon recrystallization with 9:1 ethyl acetate/hexane the reaction yielded 14 mg of 2-butyl-1-(4-(((2-cyclopropyl-2-methylpropyl)amino)methyl)benzyl)-1H-imidazo[4,5-c]quinolin-4-amine (Compound No. 63-41). Product purity was assessed to be 94% pure by reverse-phase HPLC at 254 nm, the intended synthetic mass of 455.3 Daltons was confirmed by LC/MS, and the intended synthetic structure confirmed by 300 MHz $^1$H NMR ($CDCl_3$): δ 7.82 (d, J=8.1 Hz, 1H), 7.75 (d, J=8.4 Hz, 1H), 7.45 (t, J=7.5, 15.0 Hz, 1H), 7.29 (d, J=8.4 Hz, 2H), 7.15 (t, J=7.5, 15.0 Hz, 1H), 7.03 (d, J=8.4 Hz, 2H), 5.72 (s, 2H), 5.62 (s, 2H), 3.79 (s, 2H), 2.90 (t, J=7.5, 15.6 Hz, 2H), 2.87 (s, 2H), 1.75-1.90 (m, 2), 1.40-1.55 (m, 2H), 0.94 (t, J=7.5, 14.7 Hz, 3H), 0.75 (s, 6H), 0.6-0.75 (m, 1H), 0.15-0.3 (m, 4H).

Example S10: Synthesis of 2-butyl-1-(4-((cyclohexylamino)methyl)benzyl)-1H-imidazo[4,5-c]quinolin-4-amine (Compound No. 63-49)

Part A. Tert-butyl dimethyl silyl chloride (3.31 g, 22 mmol) was added to a solution of 4-cyanobenzyl alcohol (2.66 g, 20 mmol) in N,N-dimethylformamide (20 mL) in the presence of imidazole (2.72 g, 40 mmol) at room temperature and stirred for 4 hours. The reaction mixture was poured into water (150 mL) and extracted with 10% ethyl acetate/hexane (3×75 mL). The combined organic extract was washed with water, dried over anhydrous magnesium sulfate, and concentrated under reduced pressure. The resulting product was further purified by flash chromatography, eluting with hexane, to yield 4.84 g of 4-(((tert-butyldimethylsilyl)oxy)methyl)benzonitrile.

Part B. A solution of 4-(((tert-butyldimethylsilyl)oxy)methyl)benzonitrile (4.84 g) in methanol (200 mL) was hydrogenated in a Parr hydrogenation apparatus in the presence of Raney Nickel (1.0 g slurry in water) under Hydrogen at 60 psi for 4 hours. The reaction was filtered and the filtrate concentrated under reduced pressure. The resulting product, (4-(((tert-butyldimethylsilyl)oxy)methyl)phenyl)methanamine (4.8 g), was used without purification.

Part C. A solution of 4-chloro-3-nitroquinoline (4.16 g, 20 mmol) in dichloromethane (100 mL) was slowly added to a solution of 4-(tert-butyldimethylsiloxymethyl) benzyl amine (4.8 g, 19 mmol) and diisopropylethylamine (DIPEA) (3.87 g, 30 mmol) in dichloromethane (100 mL) and stirred for 12 hours. The solvent was removed under reduced pressure, the residue dissolved in ethyl acetate (200 mL), washed with water (2×100 mL), and dried over anhydrous magnesium sulfate. The solvent was removed under reduced pressure and the resulting product was purified by flash chromatography, eluting with 1:1 ethyl acetate/hexane, to yield 4.67 g of (4-((4-(((tert-butyldimethylsilyl)oxy)methyl)benzyl)amino)quinolin-3-yl)(oxo)-$\lambda^4$-azanol.

Part D. A solution of (4-((4-(((tert-butyldimethylsilyl)oxy)methyl)benzyl)amino)-quinolin-3-yl)(oxo)-$\lambda^4$-azanol (4.67 g) in ethyl acetate (250 mL) was hydrogenated in the presence of palladium on carbon (10%, 1.0 g) at 60 psi for 4 hours. The catalyst was removed by filtration, the solvent removed from the filtrate under reduced pressure, and the product, $N^4$-(4-(((tert-butyldimethylsilyl)oxy)methyl)benzyl)quinoline-3,4-diamine (4.5 g), used without further purification.

Part E. A solution of valeryl chloride (1.50 g, 12.46 mmol, 1.05 eq.) in dichloromethane (30 mL) was added dropwise to a solution of $N^4$-(4-(((tert-butyldimethylsilyl)oxy)methyl)-benzyl)quinoline-3,4-diamine (4.5 g, 11.86 mmol) in dry pyridine (20 mL) at 0° C. After the addition, the reaction mixture was warmed to room temperature and stirred for 4 hours. The solvent and pyridine were removed under reduced pressure. The residue was dissolved in dichloromethane (300 mL) and then washed successively with water, saturated sodium bicarbonate solution (100 mL), saturated copper sulfate solution (3×50 mL), and water (100 mL), then dried over anhydrous magnesium sulfate and concentrated under reduced pressure. The product, N-(4-((4-(((tert-butyldimethylsilyl)oxy)methyl)benzyl)amino)quinolin-3-yl)pentanamide (5.5 g), was used further without purification.

Part F. A solution of N-(4-((4-(((tert-butyldimethylsilyl)oxy)methyl)benzyl)amino)-quinolin-3-yl)pentanamide (5.5 g, 11.87 mmol) in a mixture of ethanol/water (8:2 v/v, 150 mL) was heated to 60° C. in presence of potassium carbonate (2.5 g, 18.11 mmol, 1.5 eq.) for 18 hours. The solvent was removed under reduced pressure. The residue was partitioned between ethyl acetate (200 mL) and water (100 mL), the ethyl acetate layer separated and dried over anhydrous magnesium sulfate, and the residue concentrated under reduced pressure. Further purification was done by flash chromatography, eluting with 20% ethyl acetate/hexane, to yield 3.43 g of 2-butyl-1-(4-(((tert-butyldimethylsilyl)oxy)methyl)benzyl)-1H-imidazo[4,5-c]quinoline.

Part G. Meta-chloroperbenzoic acid (60-70%, 2.5 g) was added to a solution of 2-butyl-1-(4-(((tert-butyldimethylsilyl)oxy)methyl)benzyl)-1H-imidazo[4,5-c]quinoline (3.43 g, 7.4 mmol) in dichloromethane (200 mL) at room temperature and stirred for 6 hours. The reaction was quenched by adding a saturated solution of sodium sulfite solution (20 mL). The organic layer was separated, successively washed with a solution of saturated sodium bicarbonate solution (50 mL) then water (50 mL), dried over anhydrous magnesium sulfate and concentrated under reduced pressure. Further purification was done by flash chromatography with elution by 25% ethyl acetate/hexane to yield 3.1 g of 2-butyl-1-(4-(((tert-butyldimethylsilyl)oxy)methyl)-benzyl)-1H-5$\lambda^4$-imidazo[4,5-c]quinolin-5-ol.

Part H. A solution of 2-butyl-1-(4-(((tert-butyldimethylsilyl)oxy)methyl)benzyl)-1H-5$\lambda^4$-imidazo[4,5-c]quinolin-5-ol (3.1 g, 6.5 mmol) in dichloromethane (50 mL) was added to tri-n-butyl amine (2.4 g, 13 mmol) and phthalimide (1.91 g, 13 mmol) and the reaction mixture was cooled to 0° C. A solution of benzoyl chloride (1.82 g, 13 mmol) in dichloromethane (10 mL) was added slowly to the reaction, and the mixture was warmed to room temperature and stirred for 30 minutes. The reaction was diluted with dichloromethane (100 mL), successively washed with a saturated aqueous solution of ammonium chloride (100 mL) then water (100 mL), and dried over anhydrous magnesium sulfate and concentrated under reduced pressure. The resulting product was isolated by flash chromatography, eluting with 10% ethyl acetate/hexane, to yield 2.85 g of 2-(2-butyl-1-(4-(((tert-butyldimethylsilyl)oxy)methyl)benzyl)-1H-imidazo[4,5-c]quinolin-4-yl)isoindoline-1,3-dione.

Part I. A 1M solution of tetrabutylammonium fluoride (6 mL) was added to a solution of 2-(2-butyl-1-(4-(((tert-butyldimethylsilyl)oxy)methyl)benzyl)-1H-imidazo[4,5-c]quinolin-4-yl)isoindoline-1,3-dione (2.85 g, 4.7 mmol) in dry tetrahydrofuran (10 mL) at 0° C. After the addition, the reaction mixture was warmed to room temperature and further stirred for 6 hours. The reaction was quenched by the addition of saturated ammonium chloride (20 mL), diluted with ethyl acetate (100 mL), washed with water, dried over anhydrous magnesium sulfate, and concentrated under reduced pressure. Further purification was done by flash chromatography eluting with dichloromethane/hexane (1:1) to yield 1.57 g of 2-(2-butyl-1-(4-(hydroxymethyl)benzyl)-1H-imidazo[4,5-c]quinolin-4-yl)isoindoline-1,3-dione.

Part J. A solution of DMSO (2.5 g, 32 mmol) in $CH_2Cl_2$ (10 mL) was added to a solution of oxalyl chloride (2.0 g, 16 mmol) in dichloromethane (10 mL) and 3 Å molecular sieves in $CH_2Cl_2$ (20 mL) at −78° C. under argon. After 15 minutes, a solution of 2-(2-butyl-1-(4-(hydroxymethyl)benzyl)-1H-imidazo[4,5-c]quinolin-4-yl)isoindoline-1,3-dione (1.57 g, 3.2 mmol) in $CH_2Cl_2$ (3 mL) was slowly added dropwise. After 30 min, $Et_3N$ (4.5 g, 45 mmol) was added dropwise, the reaction stirred for 30 minutes at −78° C., and then slowly allowed to warm to room temperature. After stirring for another hour at room temperature, the reaction mixture was quenched by the addition of saturated ammonium chloride solution. The organic layer was separated, washed with water (25 mL), dried over anhydrous magnesium sulfate and concentrated under reduced pressure. Further purification was done by flash chromatography to yield 1.15 g of 4-((2-butyl-4-(1,3-dioxoisoindolin-2-yl)-1H-imidazo[4,5-c]quinolin-1-yl)methyl)benzaldehyde.

Part K. A solution of 4-((2-butyl-4-(1,3-dioxoisoindolin-2-yl)-1H-imidazo[4,5-c]quinolin-1-yl)methyl)benzaldehyde (2.33 mmol) and cyclohexylamine (7 mmol) in dichloromethane is heated to reflux in the presence of a catalytic amount of p-toluenesulfonic acid for 12 hours. The reaction mixture is concentrated under reduced pressure. The crude product, 2-(2-butyl-1-(4-((cyclohexylimino)methyl)benzyl)-1H-imidazo[4,5-c]quinolin-4-yl)isoindoline-1,3-dione, is used without further purification.

Part L. Sodium borohydride (10 mmol) is added to a solution of 2-(2-butyl-1-(4-((cyclohexylimino)methyl)benzyl)-1H-imidazo[4,5-c]quinolin-4-yl)isoindoline-1,3-dione in methanol at room temperature and stirred for 2 hours. The reaction mixture is quenched with saturated ammonium chloride solution and extracted with dichloromethane (3×30 mL). The combined organic layer is washed with water, dried over anhydrous magnesium sulfate and concentrated under reduced pressure. The product, 2-(2-butyl-1-(4-((cyclohexylamino)methyl)-benzyl)-1H-imidazo[4,5-c]quinolin-4-yl)isoindoline-1,3-dione, is purified by flash chromatography.

Part M. Hydrazine (100 mg) is added to a solution of 2-(2-butyl-1-(4-((cyclohexylamino)methyl)benzyl)-1H-imidazo[4,5-c]quinolin-4-yl)isoindoline-1,3-dione (0.38 mmol) in methanol and stirred for 12 hours. The solvent is removed under reduced pressure and the resulting product, 2-butyl-1-(4-((cyclohexylamino)methyl)benzyl)-1H-imidazo[4,5-c]quinolin-4-amine, is purified by flash chromatography.

Example S11: Synthesis of Exemplary N-Acyl Compounds of Formula (J-2)

Exemplary N-acyl compounds of formula (J-2) were synthesized using similar procedures as for Compound No. 63-33, through part I. $^1$H NMR and mass spectrometry data are detailed below for certain compounds of the present invention, and Table 4 provides purity data and c Log P values.

TABLE 4

(J-2)

| Compound No. | Formula (J-2), $R^0$ | % Purity (HPLC) | cLogP |
|---|---|---|---|
| 63-34 | —(CH$_2$)-cyclopropyl | 60 | 4.8 |

Compound No. 63-34: $^1$H NMR (CDCl$_3$, 400 MHz): δ 7.75 (dd, J=8.3, 0.9 Hz, 1H), 7.67 (dd, J=8.3, 1.1 Hz, 1H), 7.40 (m, J=8.3, 7.1, 1.4 Hz, 1H), 7.22 (d, J=8.2 Hz, 2H), 7.11 (m, J=8.2, 7.1, 1.2 Hz, 1H), 6.98 (d, J=8.2 Hz, 2H), 6.30 (at, 1H), 5.68 (s, 2H), 4.42 (d, J=6.0 Hz, 2H), 2.84 (add, 2H), 2.16 (dd, J=7.2 Hz, 2H), 1.81-1.75 (m, 2H), 1.48-1.37 (m, 2H), 0.91 (t, J=7.4 Hz, 3H), 0.57-0.53 (m, 2H), 0.17-0.14 (m, 2H). Mass Spec: m/z 442.6 (M+1).

Example S12: Synthesis of Exemplary Compounds of Formula (K)

Exemplary N-acyl compounds of formula (K-2) were synthesized using similar procedures as for Compound No. 63-10. $^1$H NMR and mass spectrometry data are detailed below for certain compounds of the present invention, and Table 5 lists the compounds with purity data as well as c Log P values.

Exemplary N-alkyl compounds of formula (K-1) were synthesized using similar procedures as for Compound No. 63-17. $^1$H NMR and mass spectrometry data are detailed below for certain compounds of the present invention, and Table 6 provides purity data and c Log P values.

Compound No. 63-02: $^1$H NMR (CDCl$_3$, 400 MHz): δ 7.80 (dd, J=8.4, 1.2 Hz, 1H), 7.64 (dd, J=8.2, 1.0 Hz, 1H), 7.40 (m, J=8.4, 7.0, 1.0 Hz, 1H), 7.20 (d, J=8.2 Hz, 2H), 7.09 (m, J=8.2, 7.1, 1.3 Hz, 1H), 6.96 (d, J=8.2 Hz, 2H), 6.28 (bs, 2H), 6.02 (bt, J=5.7 Hz, 1H), 5.65 (s, 2H), 4.37 (d, J=5.8 Hz, 2H), 2.83 (dd, J=7.8, 7.8 Hz, 2H), 2.15 (dd, J=7.6, 7.6 Hz, 2H), 1.81-1.73 (m, 2H), 1.64-1.56 (m, 2H), 1.42 (dq, J=15.0, 7.4 Hz, 2H), 1.32-1.21 (m, 4H), 0.91 (t, J=7.3 Hz, 3H), 0.84 (t, J=7.3 Hz, 3H). Mass Spec: m/z 468.2 (M+1).

Compound No. 63-05: $^1$H NMR (CDCl$_3$, 300 MHz): 7.89 (d, J=8.1 Hz, 1H), 7.86 (d, J=8.1 Hz, 1H), 7.69 (t, 1H), 7.74 (t, J=15.6, 8.4, 1H), 7.47 (t, J=15.5, 7.5 Hz, 1H), 7.38 (m, 4H), 7.14 (bs, 1H) 7.08 (d, J=8.1 Hz) 5.85 (s, 2H), 4.53 (d, J=6 Hz, 2H), 2.99 (t, J=7.8 Hz, 2H), 2.30 (t, J=7.5 Hz, 2H), 1.90-1.97 (m, 4H), 1.52-1.75 (m, 4H), 1.26-1.48 (m, 14H), 0.90-1.10 (m, 6H). Mass Spec: m/z 500.8 (M+1).

Compound No. 63-06: $^1$H NMR (CDCl$_3$, 300 MHz): 8.05 (d, J=8.1 Hz, 1H), 7.84 (d, J=8.4 Hz, 1H), 7.74 (t, J=8.4 Hz, 1H), 7.47 (t, J=7.5 Hz, 1H), 7.38 (d, J=8.1 Hz, 2H), 7.14 (d, J=8.1 Hz, 2H), 6.04 (s, 2H), 4.42 (s, 2H), 3.74 (s, 2H),), 3.10 (t, J=7.8 Hz, 2H), 2.29 (t, J=7.5 Hz, 2H), 1.90-1.97 (m, 2H), 1.52-1.75 (m, 4H), 1.26-1.48 (m, 12H), 0.90-1.10 (m, 6H). Mass Spec: m/z 514.5 (M+1).

Compound No. 63-07: $^1$H NMR (CDCl$_3$, 300 MHz): 7.88 (d, J=8.1 Hz, 1H), 7.69 (d, J=8.4 Hz, 1H), 7.50 (t, J=15.6, 8.4, 1H), 7.29 (d, J=8.1 Hz, 2H), 7.20 (t, J=15.5, 7.5 Hz, 1H), 7.06 (d, J=8.1 Hz, 2H), 5.90 (s, 2H), 4.33 (s, 2H), 3.74 (s, 2H),), 3.0 (t, J=15.0, 7.8 Hz, 2H), 2.21 (t, J=14.7, 7.5 Hz, 2H), 1.90-1.97 (m, 2H), 1.42-1.70 (m, 4H), 1.26-1.48 (m, 14H), 0.85-1.05 (m, 6H). Mass Spec: m/z 528.6 (M+1).

Compound No. 63-08: $^1$H NMR (CDCl$_3$, 400 MHz): δ 7.74 (d, J=8.2 Hz, 1H), 7.64 (d, J=8.2 Hz, 1H), 7.37 (dd, J=7.4, 7.4 Hz, 1H), 7.18 (d, J=8.0 Hz, 2H), 7.07 (dd, J=7.5, 7.5 Hz, 1H), 6.95 (d, J=8.0 Hz, 2H), 5.98 (bt, J=5.6 Hz, 1H), 5.89 (bs, 2H), 5.63 (s, 2H), 4.35 (d, J=5.8 Hz, 2H), 2.81 (dd, J=8.0, 8.0 Hz, 2H), 2.14 (dd, J=7.6, 7.6 Hz, 2H), 1.80-1.71 (m, 2H), 1.61-1.56 (m, 2H), 1.39 (dq, J=15.0, 7.4 Hz, 2H), 1.32-1.21 (m, 18H), 0.90 (t, J=7.3 Hz, 3H), 0.86 (t, J=7.3 Hz, 3H). Mass Spec: m/z 542.4 (M+1).

Compound No. 63-09: $^1$H NMR (DMSO-d6, 300 MHz): 8.18 (t, 1H), 7.8 (d, J=8.4 Hz, 1H), 7.6 (d, J=8.5 Hz, 1H), 7.34 (t, J=8.4, 1H), 7.18 (d, J=8.5 Hz, 2H), 6.9-7.12 (m, 3H), 6.55 (s, 2H), 5.8 (s, 2H), 4.2 (d, 2H), 2.90 (t, J=7.6 Hz, 2H), 2.2 (t, J=7.2 Hz, 2H), 1.65-1.80 (m, 2H), 1.3-1.75 (m, 4H), 1.25-1.38 (m, 10H), 0.65-1.0 (m, 6H). Mass Spec: m/z 556.9 (M+1).

Compound No. 63-10: $^1$H NMR (CDCl$_3$, 300 MHz): 7.98 (d, J=8.1 Hz, 1H), 7.75 (d, J=8.4 Hz, 1H), 7.67 (t, J=8.4 Hz, 1H), 7.40 (t, J=7.5 Hz, 1H), 7.30 (d, J=8.1 Hz, 2H), 7.06 (d, J=8.1 Hz, 2H), 5.95 (s, 2H), 4.33 (s, 2H), 3.74 (s, 2H),), 3.01 (t, J=7.8 Hz, 2H), 2.20 (t, J=7.5 Hz, 2H), 1.82-1.9 (m, 2H), 1.42-1.70 (m, 4H), 1.26-1.48 (m, 20H), 0.85-1.05 (m, 6H). Mass Spec: m/z 570.8 (M+1).

Compound No. 63-11: $^1$H NMR (CDCl$_3$, 300 MHz): 7.98 (d, J=8.1 Hz, 1H), 7.76 (d, J=8.4 Hz, 1H), 7.65 (t, J=8.4 Hz, 1H), 7.38 (t, J=7.5 Hz, 1H), 7.30 (d, J=8.1 Hz, 2H), 7.06 (d, J=8.1 Hz, 2H), 5.95 (s, 2H), 4.33 (s, 2H), 3.74 (s, 2H), 3.03 (t, J=7.8 Hz, 2H), 2.21 (t, J=7.5 Hz, 2H), 1.82-1.9 (m, 2H), 1.42-1.70 (m, 4H), 1.26-1.48 (m, 22H), 0.85-1.05 (m, 6H). Mass Spec: m/z 585.2 (M+1).

Compound No. 63-31: $^1$H NMR (CD$_3$OD, 300 MHz): 7.82 (d, J=8.4 Hz, 1H), 7.70 (d, J=8.5 Hz, 1H), 7.42 (t, J=8.4, 1H), 7.34 (d, J=8.5 Hz, 2H), 7.10 (t, J=8.4 Hz, 1H), 7.02 (d, J=8.3 Hz, 2H), 5.9 (s, 2H), 4.39 (s, 2H),), 3.0 (t, J=7.6 Hz, 2H), 2.25 (t, J=7.2 Hz, 2H), 1.42-1.90 (m, 6H), 1.2-1.4 (m, 13H), 0.65-1.0 (m, 6H). Mass Spec: m/z 598.7 (M+1).

Compound No. 63-13: $^1$H NMR (CDCl$_3$, 400 MHz): δ 7.77 (d, J=8.2 Hz, 1H), 7.67 (d, J=8.2 Hz, 1H), 7.41 (dd, J=7.4, 7.4 Hz, 1H), 7.21 (d, J=8.0 Hz, 1H), 7.11 (dd, J=7.5, 7.5 Hz, 1H), 6.98 (d, J=8.0 Hz, 2H), 5.87 (bt, J=5.6 Hz, 1H), 5.87 (bs, 2H), 5.68 (s, 2H), 4.39 (d, J=5.8 Hz, 2H), 2.85 (dd, J=8.0, 8.0 Hz, 2H), 2.17 (dd, J=7.6, 7.6 Hz, 2H), 1.83-1.75 (m, 2H), 1.65-1.58 (m, 2H), 1.43 (dq, J=15.0, 7.4 Hz, 2H), 1.32-1.21 (m, 30H), 0.92 (t, J=7.3 Hz, 3H), 0.88 (t, J=7.3 Hz, 3H). Mass Spec: m/z 625.5 (M+1).

Compound No. 63-00: $^1$H NMR (MeOHd4, 400 MHz): δ 7.70 (dd, J=8.4, 1.0 Hz, 1H), 7.63 (dd, J=8.4, 0.8 Hz, 1H), 7.36 (m, J=8.4, 7.0, 1.4 Hz, 1H), 7.27 (d, J=8.2 Hz, 2H), 7.03 (m, J=8.3, 7.0, 1.3 Hz, 1H), 6.97 (d, J=8.4 Hz, 2H), 5.72 (s, 2H), 3.72 (s, 2H), 2.88 (dd, J=7.6, 7.6 Hz, 2H), 1.77-1.69 (m, 2H), 1.45-1.35 (m, 2H), 0.90 (t, J=7.4 Hz, 3H). Mass Spec: m/z 360.2 (M+1).

Compound No. 63-17: $^1$H NMR (CDCl$_3$, 300 MHz): 7.8 (d, J=8.4 Hz, 1H), 7.70 (d, J=8.5 Hz, 1H), 7.45 (t, J=8.4, 1H), 7.34 (d, J=8.5 Hz, 2H), 7.10 (t, J=8.4 Hz, 1H), 7.02 (d, J=8.3 Hz, 2H), 5.70 (br s, 4H), 3.80 (s, 2H),), 2.89 (t, J=7.6 Hz, 2H), 2.62 (t, J=7.2 Hz, 2H), 1.75-1.84 (m, 2H), 1.2-1.75 (m, 8H), 0.65-1.0 (m, 6H). Mass Spec: m/z 430.3 (M+1).

Compound No. 63-18: $^1$H NMR (CDCl$_3$, 300 MHz): 7.8 (d, J=8.4 Hz, 1H), 7.70 (d, J=8.5 Hz, 1H), 7.45 (t, J=8.4, 1H), 7.34 (d, J=8.5 Hz, 2H), 7.10 (t, J=8.4 Hz, 1H), 7.02 (d, J=8.3 Hz, 2H), 5.72 (br s, 4H), 3.76 (s, 2H),), 2.89 (t, J=7.6 Hz, 2H), 2.62 (t, J=7.2 Hz, 2H), 1.75-1.84 (m, 2H), 1.4-1.6 (m, 4H), 1.2-1.35 (br s, 4H), 0.65-1.0 (m, 6H). Mass Spec: m/z 444.6 (M+1).

Compound No. 63-19: $^1$H NMR (CDCl$_3$, 300 MHz): 7.8 (d, J=8.4 Hz, 1H), 7.70 (d, J=8.5 Hz, 1H), 7.45 (t, J=8.4, 1H), 7.34 (d, J=8.5 Hz, 2H), 7.10 (t, J=8.4 Hz, 1H), 7.02 (d, J=8.3 Hz, 2H), 5.70 (br s, 4H), 3.80 (s, 2H),), 2.89 (t, J=7.6 Hz, 2H), 2.62 (t, J=7.2 Hz, 2H), 1.75-1.84 (m, 2H), 1.4-1.6 (m, 4H), 1.2-1.35 (b, s, 8H), 0.65-1.0 (m, 6H). Mass Spec: m/z 458.4 (M+1).

Compound No. 63-20: $^1$H NMR (CDCl$_3$, 300 MHz): 7.8 (d, J=8.4 Hz, 1H), 7.70 (d, J=8.5 Hz, 1H), 7.45 (t, J=8.4, 1H), 7.34 (d, J=8.5 Hz, 2H), 7.10 (t, J=8.4 Hz, 1H), 7.02 (d, J=8.3 Hz, 2H), 5.70 (br s, 4H), 3.80 (s, 2H),), 2.89 (t, J=7.6 Hz, 2H), 2.62 (t, J=7.2 Hz, 2H), 1.75-1.84 (m, 2H), 1.4-1.6 (m, 4H), 1.2-1.35 (b, s, 10H), 0.65-1.0 (m, 6H). Mass Spec: m/z 472.4 (M+1).

Compound No. 63-21: $^1$H NMR (CDCl$_3$, 300 MHz): 7.8 (d, J=8.4 Hz, 1H), 7.70 (d, J=8.5 Hz, 1H), 7.45 (t, J=8.4, 1H), 7.34 (d, J=8.5 Hz, 2H), 7.10 (t, J=8.4 Hz, 1H), 7.02 (d, J=8.3 Hz, 2H), 5.70 (br s, 4H), 3.80 (s, 2H),), 2.89 (t, J=7.6 Hz, 2H), 2.62 (t, J=7.2 Hz, 2H), 1.75-1.84 (m, 2H), 1.4-1.6 (m, 4H), 1.2-1.35 (b, s, 12H), 0.65-1.0 (m, 6H). Mass Spec: m/z 486.5 (M+1).

Compound No. 63-22: $^1$H NMR (CDCl$_3$, 300 MHz): 7.8 (d, J=8.4 Hz, 1H), 7.70 (d, J=8.5 Hz, 1H), 7.45 (t, J=8.4, 1H), 7.34 (d, J=8.5 Hz, 2H), 7.10 (t, J=8.4 Hz, 1H), 7.02 (d, J=8.3 Hz, 2H), 5.70 (br s, 4H), 3.80 (s, 2H),), 2.89 (t, J=7.6 Hz, 2H), 2.62 (t, J=7.2 Hz, 2H), 1.75-1.84 (m, 2H), 1.4-1.6 (m, 4H), 1.2-1.35 (b, s, 14H), 0.65-1.0 (m, 6H). Mass Spec: m/z 500.5 (M+1).

Compound No. 63-24: $^1$H NMR (CDCl$_3$, 300 MHz): 7.78 (d, J=8.4 Hz, 1H), 7.70 (d, J=8.5 Hz, 1H), 7.43 (t, J=8.4, 1H), 7.28 (d, J=8.5 Hz, 2H), 7.10 (t, J=8.4 Hz, 1H), 6.98 (d, J=8.3 Hz, 2H), 5.70 (br s, 4H), 3.73 (s, 2H),), 2.87 (t, J=7.6 Hz, 2H), 2.58 (t, J=7.2 Hz, 2H), 1.71-1.84 (m, 2H), 1.38-1.55 (m, 4H), 1.10-1.35 (m, 18H), 0.65-1.0 (m, 6H). Mass Spec: m/z 528.7 (M+1).

Compound No. 63-32: $^1$H NMR (CDCl$_3$, 300 MHz): 7.8 (d, J=8.4 Hz, 1H), 7.73 (d, J=8.5 Hz, 1H), 7.42 (t, J=8.4, 1H), 7.34 (d, J=8.5 Hz, 2H), 7.12 (t, J=8.4 Hz, 1H), 7.02 (d, J=8.3 Hz, 2H), 5.73 (s, 2H), 5.5 (br s, 2H) 3.75 (s, 2H),), 2.90 (t, J=7.6 Hz, 2H), 2.62 (t, J=7.2 Hz, 2H), 1.75-1.85 (m, 4H), 1.4-1.6 (m, 4H), 1.25-1.38 (m, 15H), 0.65-1.0 (m, 6H). Mass Spec: m/z 584.9 (M+1).

Compound No. 63-29: $^1$H NMR (CDCl$_3$, 300 MHz): 7.8 (d, J=8.4 Hz, 1H), 7.73 (d, J=8.5 Hz, 1H), 7.42 (t, J=8.4, 1H), 7.34 (d, J=8.5 Hz, 2H), 7.12 (t, J=8.4 Hz, 1H), 7.02 (d, J=8.3 Hz, 2H), 5.72 (s, 2H), 3.80 (s, 2H), 3.78 (s, 2H), 2.90 (t, J=7.6 Hz, 2H), 2.62 (t, J=7.2 Hz, 2H), 1.65-1.85 (m, 2H), 1.35-1.6 (m, 4H), 1.25-1.38 (m, 15H), 0.65-1.0 (m, 6H). Mass Spec: m/z 612.8 (M+1).

TABLE 5

(K-2)

| Compound No. | Formula (K-2), R | % Purity (HPLC) | cLogP |
|---|---|---|---|
| 63-02 | —C$_5$H$_{11}$ | 91 | 4.6 |
| 63-05 | —C$_8$H$_{17}$ | 98 | 6.1 |
| 63-06 | —C$_9$H$_{19}$ | 95 | 6.6 |
| 63-07 | —C$_{10}$H$_{21}$ | 94 | 7.2 |
| 63-08 | —C$_{11}$H$_{23}$ | 96 | 7.7 |
| 63-09 | —C$_{12}$H$_{25}$ | 99 | 8.2 |
| 63-10 | —C$_{13}$H$_{27}$ | 96 | 8.7 |
| 63-11 | —C$_{14}$H$_{29}$ | 94 | 9.2 |
| 63-13 | —C$_{17}$H$_{35}$ | 92 | 10.7 |

| Compound No. | Comparative Compound, R | % Purity (HPLC) | cLogP |
|---|---|---|---|
| 63-31 | —C$_{15}$H$_{31}$ | 95 | 9.7 |

TABLE 6

(K-1)

| Compound No. | Formula (K-1), R'' | % Purity (HPLC) | cLogP |
|---|---|---|---|
| 63-17 | —C$_5$H$_{11}$ | 90 | 0.7 |
| 63-18 | —C$_6$H$_{13}$ | 91 | 1.2 |
| 63-19 | —C$_7$H$_{15}$ | 90 | 1.7 |
| 63-20 | —C$_8$H$_{17}$ | 92 | 2.2 |
| 63-21 | —C$_9$H$_{19}$ | 91 | 2.7 |
| 63-22 | —C$_{10}$H$_{21}$ | 93 | 3.2 |
| 63-24 | —C$_{12}$H$_{25}$ | 92 | 4.2 |
| 63-29 | —C$_{18}$H$_{37}$ | 93 | 7.2 |

| Compound No. | Comparative Compound, R'' | % Purity (HPLC) | cLogP |
|---|---|---|---|
| 63-00 | —H | 98 | -1.1 |
| 63-32 | —C$_{16}$H$_{33}$ | 93 | 6.2 |

Example S13: Synthesis of Additional Exemplary N-Alkyl Compounds of Formula (K-1)

The exemplary N-alkyl Compound Nos. 63-16, 63-23, 63-25, 63-26, 63-27, 63-28, and 63-30 of formula (K-1) are synthesized using a similar procedure as described for Compound No. 63-17 (Example S2). In Part I, the following carboxylic acids are used in place of the valeric acid used for Compound No. 63-17: n-butanoic acid (Compound No. 63-16); undecanoic acid (Compound No. 63-23); tridecanoic acid (Compound No. 63-25); tetradecanoic acid (Compound No. 63-26); pentadecanoic acid (Compound No. 63-27); heptadecanoic acid (Compound No. 63-28); and nonadecanoic acid (Compound No. 63-30). The resulting N-acyl derivatives are then reduced to the final N-alkyl compounds according to Part J described for Example S2.

Example S14: Synthesis of Additional Exemplary N-Acyl Compounds of Formula (K-2)

The exemplary N-acyl Compound Nos. 63-01, 63-03, 63-04, 63-12, 63-14, and 63-15 of formula (K-2) are synthesized using a similar procedure as described for Compound No. 63-10 (Example S1) through Part H. In Part I, the following carboxylic acids are used in place of the myristic acid used for Compound No. 63-10: pentanoic acid (Compound No. 63-01), heptanoic acid (Compound No. 63-03), octanoic acid (Compound No. 63-04), heptadecanoic acid (Compound No. 63-12), nonadecanoic acid (Compound No. 63-14), and arachidic acid (Compound No. 63-15), to form the N-acyl products.

Biological Examples

Example B1. In Vitro Biological Assays and Results

Methods

Plasmacytoid dendritic cell (pDC)-enriched peripheral blood mononuclear cells (PBMCs) were prepared from the blood of a series of human donors (3-5 donors/experiment). PBMCs were isolated using Ficoll-Paque Premium® (GE Healthcare, Chicago Ill.) using methods well known to those in the art. pDCs were magnetically isolated from the total recovered PBMC population using CD304 (BDCA-4/Neuropilin-1) microbeads (Miltenyi Biotec, San Diego Calif.), according to the manufacturer's instructions. Isolated pDCs were then added back to between 1 and $2 \times 10^8$ of the corresponding donor's PBMCs for relative enrichment of this cell type. Duplicate cultures of pDC-enriched PBMCs ($2.5 \times 10^6$ cells/mL in RPMI-1640 media plus 10% fetal bovine serum, cultured in 96 well plates) were then incubated for 24 hours with Compound Nos. 63-02, 63-05 through 63-11, 63-13, 63-31, 63-34, 63-38 through 63-47, and their unmodified congener 1-(4-aminomethylbenzyl)-2-butyl-1H-imidazo[4,5-c]quinolin-4-amine (Compound No. 63-00) at 10 serially diluted concentrations covering the range of 0.1 nM to 400 nM. Culture supernatants were collected and interferon-alpha (IFNα) protein levels were measured by ELISA (MabTech, Cincinnati Ohio), according to the manufacturer's instructions.

Monocytes were magnetically isolated from PBMCs, prepared as described above, following labeling with CD14 microbeads (Miltenyi Biotec, San Diego Calif.), according to the manufacturer's instructions. Duplicate cultures of monocytes ($1 \times 10^6$ cells/mL in RPMI-1640 plus 10% fetal bovine serum, cultured in 96 well plates) were incubated for 24 hours with Compound Nos. 63-02, 63-05 through 63-11, 63-13, 63-31, 63-34, 63-38 through 63-47, and their unmodified congener 1-(4-aminomethylbenzyl)-2-butyl-1H-imidazo[4,5-c]quinolin-4-amine (Compound No. 63-00) at 10 serially diluted concentrations covering the range of 2 nM to 40 µM. Culture supernatants were collected and tumor necrosis factor alpha (TNFα) protein levels were measured by ELISA (MabTech, Cincinnati Ohio), according to the manufacturer's instructions.

Results

The effect of modifying either i) the compound of formula (K-2), where R is a linear alkyl chain of 5 (Compound No. 63-02), 8 (Compound No. 63-05), 9 (Compound No. 63-06), 10 (Compound No. 63-07), 11 (Compound No. 63-08), 12 (Compound No. 63-09), 13 (Compound No. 63-10), 14 (Compound No. 63-11), 15 (Compound No. 63-31), or 17 (Compound No. 63-13) carbons added to the amide group on the benzyl methyl moiety, or ii) the compound of formula (J-2), where $R^0$ is a cyclopropylmethyl moiety with 4 (Compound No. 63-34) carbons added to the amide group on the benzyl methyl moiety, on in vitro TLR7 (induction of IFNα protein in pDC-enriched PBMC cultures) and TLR8 (induction of TNFα protein in monocyte cultures) agonist bioactivity was assessed. Table B1-1 summarizes the structural, c Log P calculation, and TLR7/8 agonist bioactivity relationships for Compound Nos. 63-00, 63-02, 63-05 through 63-11, 63-13, 63-31, and 63-34. The TLR7 and TLR8 agonist potency is shown in Table B1-1 and is reported as the effective concentration at 50% of the maximal response, in nanomolar ($EC_{50}$ in nM). Modification of Compound No. 63-00 with these alkyl chains generally resulted in a 2-3× loss of TLR7 agonist potency, except for the 5 (Compound No. 63-02) and 17 (Compound No. 63-13) carbon variants which lost 11× and 41× potency, respectively. In contrast, the 5 (Compound No. 63-02), 8 (Compound No. 63-05), 9 (Compound No. 63-06), 10 (Compound No. 63-07), 15 (Compound No. 63-31), and 17 (Compound No. 63-13) carbon chain variants lost >10-26× of TLR8 agonist potency compared to unmodified Compound No. 63-00. Unexpectedly, variants with carbon chain lengths of 11 (Compound No. 63-08), 12 (Compound No. 63-09), 13 (Compound No. 63-10), and 14 (Compound No. 63-11) did not lose as much agonist activity, with Compound No. 63-10 demonstrating only a 2.4× loss of TLR8 agonist potency compared to unmodified Compound No. 63-00. Compound No. 63-34, where $R^0$ is a cyclopropylmethyl group, demonstrated an 8-fold loss of TLR7 agonist potency and a 7-fold loss of TLR8 agonist potency compared to unmodified Compound No. 63-00. These data are comparable to the TLR7 and TLR8 agonist potency loss observed for the linear 5 carbon alkyl chain modified Compound No. 63-02.

TABLE B1-1

Structural, cLogP Calculation, and Bioactivity Relationships for Select Compounds of Formula (J-2) and (K-2).

| Compound No. | cLogP | TLR7 ($EC_{50}$ in nM) | TLR8 ($EC_{50}$ in nM) |
|---|---|---|---|
| 63-02 | 4.6 | 11 | 2,137 |
| 63-05 | 6.1 | 3 | 2,167 |
| 63-06 | 6.6 | 2 | 2,746 |
| 63-07 | 7.2 | 1 | 2,644 |
| 63-08 | 7.7 | 3 | 1,271 |
| 63-09 | 8.2 | 2 | 970 |
| 63-10 | 8.7 | 2 | 522 |

TABLE B1-1-continued

Structural, cLogP Calculation, and Bioactivity Relationships
for Select Compounds of Formula (J-2) and (K-2).

|  | cLogP | TLR7 ($EC_{50}$ in nM) | TLR8 ($EC_{50}$ in nM) |
| --- | --- | --- | --- |
| 63-11 | 9.2 | 2 | 827 |
| 63-13 | 10.7 | 41 | 5,723 |
| 63-34 | 4.8 | 8 | 1,486 |
| Comparative Compound | | | |
| 63-00 | −1.1 | 1 | 217 |
| 63-31 | 9.7 | 3 | 2,152 |

The effect of either i) modifying the compound of formula (K-1), where R is a linear alkyl chain of 5 (Compound No. 63-17), 6 (Compound No. 63-18), 7 (Compound No. 63-19), 8 (Compound No. 63-20), 9 (Compound No. 63-21), 10 (Compound No. 63-22), 12 (Compound No. 63-24), 16 (Compound No. 63-32), or 18 (Compound No. 63-29) carbons added to the amine group on the benzyl methyl moiety, or ii) modifying the compound of formula (J-1), where $R^0$ is a cyclopropylethyl moiety with 5 (Compound No. 63-33), cyclobutylethyl moiety with 6 (Compound No. 63-35), or cyclopentylethyl moiety with 7 (Compound No. 63-36) carbons added to the amide group on in vitro TLR7 (induction of IFNα protein in pDC-enriched PBMC cultures) and TLR8 (induction of TNFα protein in monocyte cultures) agonist bioactivity was assessed. Table B1-2 summarizes the structural, c Log P calculation, and TLR7/8 agonist bioactivity relationships for Compound Nos. 63-00, 63-17 through 63-22, 63-24, 63-29, 63-32, 63-33, 63-35, and 63-36. The TLR7 and TLR8 agonist potency is shown in Table B1-2 and is reported as the effective concentration at 50% of the maximal response, in nanomolar ($EC_{50}$ in nM). Modification of Compound No. 63-00 with linear alkyl chains demonstrated increasing loss of TLR7/8 agonist potency with increasing number of carbons, although the 5 (Compound No. 63-17) and 6 (Compound No. 63-18) carbon variants demonstrated slightly improved TLR8 agonist potency. Modification of Compound No. 63-00 with three hydrocarbyl groups, cyclopropylethyl, cyclobutylethyl, and cyclopentylethyl, caused a 4- to 12-fold loss of TLR7 agonist bioactivity, but resulted in a 2-3 fold increase in agonist potency.

TABLE B1-2

Structural, cLogP Calculation, and Bioactivity Relationships
for Select Compounds of Formula (J-1) and (K-1).

|  | cLogP | TLR7 ($EC_{50}$ in nM) | TLR8 ($EC_{50}$ in nM) |
| --- | --- | --- | --- |
| Compound No. | | | |
| 63-17 | 0.7 | 2 | 104 |
| 63-18 | 1.2 | 15 | 213 |
| 63-19 | 1.7 | 24 | 752 |
| 63-20 | 2.2 | 51 | 1,221 |
| 63-21 | 2.7 | 68 | 947 |
| 63-22 | 3.2 | 62 | 821 |
| 63-24 | 4.2 | 32 | 1,036 |
| 63-29 | 7.2 | 19 | 2,774 |
| 63-33 | 3.9 | 4 | 75 |
| 63-35 | 4.4 | 12 | 70 |
| 63-36 | 4.9 | 11 | 117 |
| Comparative Compound | | | |
| 63-00 | −1.1 | 1 | 217 |
| 63-32 | 6.2 | 157 | 3,099 |

The effect of modifying the compound of formula (J-1), where $R^0$ is a (cyclopropyl)ethyl moiety (Compound No. 63-33), (cyclobutyl)ethyl moiety (Compound No. 63-35), (cyclopentyl)ethyl moiety (Compound No. 63-36), (cyclopropyl)methyl moiety (Compound No. 63-38), (2-methylcyclopropyl)methyl moiety (Compound No. 63-39), (2,2-dimethylcyclopropyl)methyl moiety (Compound No. 63-40), (2-cyclopropyl)-(2,2-dimethyl)ethyl moiety (Compound No. 63-41), (1-methylcyclopropyl)ethyl moiety (Compound No. 63-42), (3-cyclopropyl)propyl moiety (Compound No. 63-43), (cyclobutyl)methyl moiety (Compound No. 63-44), (1-methylcyclobutyl)methyl moiety (Compound No. 63-45), (3-methylcyclobutyl)methyl moiety (Compound No. 63-46), or (2-cyclobutyl)-(2,2-dimethyl)ethyl moiety (Compound No. 63-47), on in vitro TLR7 (induction of IFNα protein in pDC-enriched human PBMC cultures) and TLR8 (induction of TNFα protein in human monocyte cultures) agonist bioactivity was assessed. Table B1-3 summarizes the TLR7/8 agonist bioactivity relationships for Compound Nos. 63-00, 63-33, 63-35, 63-36, and 63-38 through 63-47. The TLR7 and TLR8 agonist potency shown in Table B1-3 is reported as a percent of the effective compound concentration at 50% of the maximal response determined for Compound No. 63-00. Variation between human blood donors in the levels of cytokines secreted from purified immune cells used to assess the potency of TLR7 and TLR8 agonist compounds results in minor variations in the absolute values calculated for $EC_{50}$ potency for a given compound; to normalize for this effect, the data in Table B1-3 is expressed as a percentage of the $EC_{50}$ determined for the unmodified, imidazoquinoline-based chemical structure (Compound No. 63-00).

As shown in Table B1-3, modification of the chemical structure of Compound No. 63-00 to produce compounds of formula (J-1) with varying cycloalkyl moieties resulted in attenuation of the TLR7 agonist potency up to 11-fold. The (cyclobutyl)methyl (Compound No. 63-44) and (1-methylcyclobutyl)methyl (Compound No. 63-45) variants demonstrated the least amount of attenuated TLR7 agonist activity (1.2 and 1.9-fold lower potency, respectively), whereas the (cyclopentyl)ethyl (Compound No. 63-36) and (2-cyclobutyl)-(2,2-dimethyl)ethyl (Compound No. 63-47) variants demonstrated the greatest amount of attenuated TLR7 agonist activity (10.9 and 9.0-fold lower potency, respectively). Unexpectedly, the same set of structural modifications to the chemical structure of Compound No. 63-00 resulted in comparable or greater TLR8 agonist potency. The (cyclobutyl)methyl (Compound No. 63-44) and (1-methylcyclobutyl)methyl (Compound No. 63-45) variants demonstrated the greatest increase in TLR8 agonist potency (5.9 and 7.7-fold greater potency, respectively). In contrast, the (1-methylcyclopropyl)ethyl (Compound No. 63-42) and (2-cyclobutyl)-(2,2-dimethyl)ethyl (Compound No. 63-47) variants demonstrated slightly improved to slightly inferior TLR8 agonist activity compared to Compound No. 63-00. A TLR7/8 agonist small molecule with more closely matched TLR7 and TLR8 agonist potency is more likely to yield comparable activation of the 2 receptors systems upon administration of a therapeutic dose of compound in a given pharmaceutical composition, thus activating a broader range of relevant immune cell types. Compounds with balanced dual potency would also allow for the synthesis and characterization of a single active pharmaceutical ingredient, thereby facilitating GMP manufacturing at lower costs and enabling a more straightforward and predictable regulatory pathway.

TABLE B1-3

Structural and Bioactivity Relationships
for Select Compounds of Formula (J-1).

| Compound No. | TLR7 (% of Compound No. 63-00 EC$_{50}$ Value) | TLR8 (% of Compound No. 63-00 EC$_{50}$ Value) |
|---|---|---|
| 63-33 | 290 | 41 |
| 63-35 | 715 | 53 |
| 63-36 | 1,085 | 72 |
| 63-38 | 345 | 37 |
| 63-39 | 220 | 48 |
| 63-40 | 215 | 51 |
| 63-41 | 360 | 43 |
| 63-42 | 445 | 85 |
| 63-43 | 440 | 77 |
| 63-44 | 120 | 17 |
| 63-45 | 190 | 13 |
| 63-46 | 400 | 39 |
| 63-47 | 900 | 108 |
| Comparative Compound | | |
| 63-00 | 100 | 100 |

Example B2. Preparation of Pharmaceutical Compositions

Example B2-1. Preparation of Sesame Oil-Based Pharmaceutical Compositions

Compound Nos. 63-17, 63-18, 63-10, and 63-33 were formulated for in vivo administration in 95% sesame oil/5% ethanol (v/v) as follows. Super Refined® sesame oil was obtained from Croda Inc. (Edison, N.J.) and ethanol (200 proof, USP grade) was obtained from Pharmaco-AAPER (Brookfield, Conn.). The compounds were placed in a glass vial and 100% ethanol added to make 2.75 mg/mL suspensions. The solutions were solubilized by vortexing for 30 seconds and then held in an ultrasonic water bath set at 50° C. for 30 minutes. One mL of these solutions was then transferred to a 20 mL glass vial containing 16.0 g of sesame oil, mixed on an end-over-end mixer for 20 minutes at ambient temperature, and then transferred to a 90° C. water bath for 2 hours to ensure complete solubilization. The formulated compounds were cooled to 37° C. before sterilization by 0.2 micron filtration. Formulated compounds were stored at 2-8° C. in rubber stopper-capped sterile glass vials. The concentrations of the components in the final formulation were as follows: 0.1 mg/mL (w/v) compound in 95% sesame oil and 5% ethanol (v/v).

Example B2-2. Preparation of Squalene Oil-in-Water Nanoemulsion-Based Pharmaceutical Compositions Compound Nos. 63-17, 63-18, 63-10, and 63-33 were formulated for in vivo administration in squalene oil-in-water-based nanoemulsions as follows. Squalene (≥98%, liquid), Tween®80 (Polysorbate 80), glycerol, and sodium citrate tribasic dihydrate were obtained from Sigma-Aldrich (St. Louis, Mo.). 1,2-dioleoyl-sn-glycero-3-phosphocholine (DOPC) was obtained from Avanti Polar Lipids (Alabaster, Ala.). Cell culture grade water (sterile water for injection) was obtained from Corning Life Sciences (Tewksbury, Mass.). To form the oil phase, DOPC (175.6 mg) was added to squalene oil (1.4 mL) in a 4 mL glass vial. The mixture was then incubated in a sonicating water bath at 70° C. for 45 minutes, with brief vortexing every 15 minutes, until the lipid was dissolved. The indicated compound (13.7 mg) was added to the squalene/DOPC solution and vortexed vigorously for one minute. This solution was then incubated in a sonicating water bath at 70° C. for 30 minutes, with brief vortexing every 10 minutes. If needed in order to generate a clear solution, the mixture was further incubated in a 90° C. water bath for 2 hours with brief vortexing every 15 minutes. Separately, to form the water phase, Tween®80 (70 mg) and glycerol (315 mg) were mixed with 100 mM sodium citrate pH 6.5 solution (3.5 mL) and water (29.8 mL) in a 50 mL polypropylene tube.

An oil-in-water emulsion was formed by combining the squalene oil/DOPC/compound-containing oil phase and the Tween®80/glycerol/sodium citrate-containing water phase followed by high shear mixing with a Polytron® mixer (Kinematica, Luzern CH) for 5 minutes at 24,000 rpm. The crude emulsion was then submitted to high pressure homogenization using a Microfluidics M-110P Microfluidizer® (Westwood, Mass.) for 8 passes at approximately 30,000 psi. Analysis by dynamic light scattering (Malvern NanoS®, Malvern UK) indicated a mean oil drop diameter of 150-175 nm, with a dispersity index of <0.15. The compound-containing nanoemulsion formulation was then sterile filtered using a 0.2 micron sterile syringe filter and stored at 2-8° C. in rubber stopper-capped sterile glass vials.

The concentrations of various components in the final nanoemulsion formulation were as follows: 0.4 mg/mL compound (w/v), 4% squalene oil (v/v), 0.5% DOPC (w/v), 0.2% Tween®80 (w/v), 0.9% glycerol (w/v), and 10 mM sodium acetate. Pharmaceutical preparations for the in vivo administration of the compounds in a squalene oil-in-water nanoemulsion formulation were prepared prior to use by diluting 1:1 in Dulbecco's phosphate-buffered saline, with mixing by gentle inversion.

Example B3. In Vivo Systemic Immune Activation Assay

Small molecule TLR7 and TLR7/8 agonists derived from the 1H-imidazo[4,5-c]quinoline privileged template (see e.g., Imiquimod, Resiquimod) are known to rapidly distribute to the systemic compartment following intratumoral, subcutaneous, or intramuscular injection. Broad systemic distribution of these agonist compounds in wild-type mice induces TLR7-dependent cytokine responses, primarily in spleen and liver cells, which can subsequently be detected in the serum within 3-6 hours. The rapid increase in serum cytokine biomarkers (e.g., IL-6 and IL-12p40) can be used to assess the kinetics of systemic distribution of a locally administered TLR agonist.

The kinetics of distribution of pharmaceutical compositions comprised of Compound Nos. 63-00, 63-17, or 63-10 formulated in 95% sesame oil/5% ethanol (v/v) were assessed following a single subcutaneous injection in wild-type mice. All in vivo procedures were conducted in accordance with approved Institutional Animal Care and Use Committee (IACUC) protocols. The animals were housed in a facility that is accredited by the Association for Accreditation and Laboratory Animal Care (AALAC, Frederick Md.). Wild-type female BALB/c mice (15-20 gm) were obtained from Envigo (Hayward, Calif.) and acclimated for 2-3 days prior to use.

The pharmaceutical compositions were made with the three compounds, at a final concentration of 200 µg/mL, in a manner similar to that described in Example B2-1. At T=0, groups of 3 mice were anesthetized with 1% isoflurane and injected subcutaneously in the right footpad with 5 µg of each of the three compounds, or a vehicle control, in 25 uL of 95% sesame oil/5% ethanol (v/v). Then, at T=3, 6, and 24 hours, three animals from each group were anesthetized with 1% isoflurane to facilitate blood collection by cardiac puncture. Samples were processed to serum, and stored at −20° C. for further analysis.

Figure 1B:
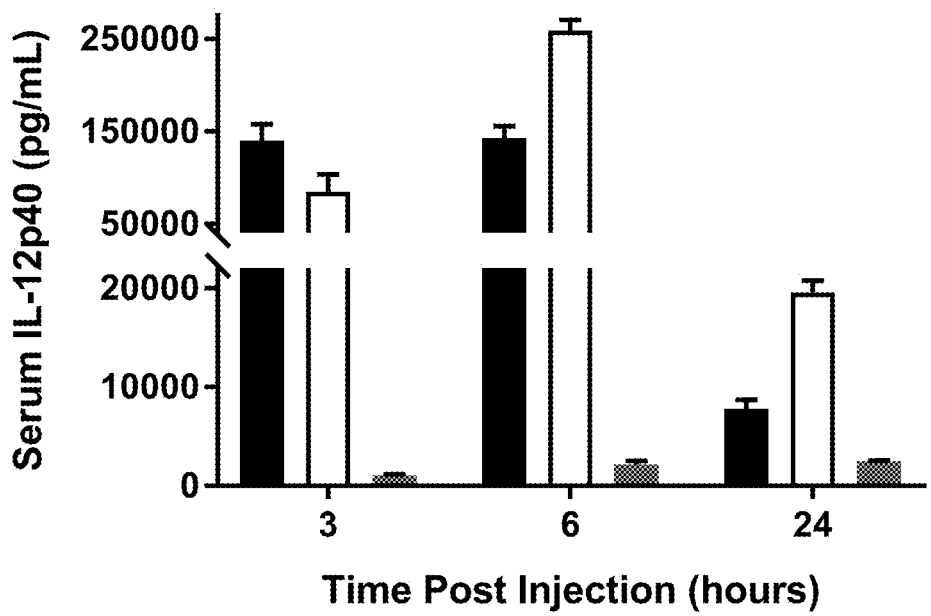

Serum IL-6 and IL-12p40 levels were quantitated by ELISA from each individual animal to determine whether compounds derivatized with longer alkyl chains demonstrated a slower rate of systemic distribution. The non-alkyl chain modified Compound No. 63-00 induced elevated serum levels of IL-6 and IL-12p40 at 3 hours (IL-6=772±141 pg/mL, IL-12p40=139,767±31,024 pg/mL) and 6 hours (IL-6=160±19 pg/mL, IL-12p40=142,359±22,350 pg/mL) which returned to baseline by 24 hours (IL-6=32±2 pg/mL, IL-12p40=7,796±1,545 pg/mL), as shown in FIG. 1. The pentylamino variant, Compound No. 63-17, showed a similar magnitude and kinetics of initial cytokine production in the serum compartment at 3 hours (IL-6=853±539 pg/mL, IL-12p40=84,731±32,530 pg/mL) and at 6 hours (IL-6=414±105 pg/mL, IL-12p40=258,645±19,982 pg/mL), as well as a return to baseline levels by 24 hours (IL-6=33±4 pg/mL, IL-12p40=19,546±2,116 pg/mL). The tetradecanamide variant, Compound No. 63-10, which possessed a substantially higher c Log P value, demonstrated no detectable increase in serum cytokines at 3, 6, or 24 hours (3 hours: IL-6=49±32 pg/mL, IL-12p40=1,012±246 pg/mL; at 6 hours: IL-6=33±4 pg/mL, IL-12p40=2,179±597 pg/mL; and at 24 hours: IL-6=32±2 pg/mL, IL-12p40=2,436±237 pg/mL). These data are consistent with the interpretation that despite the fact that all three compounds demonstrate equal TLR7 agonist bioactivity in vitro (see Tables B1-1 and B1-2) the higher hydrophobicity of Compound No. 63-10, as well as its formulation in a pharmaceutical composition of sesame oil/ethanol promotes the molecule's retention at the site of injection.

Example B4. Anti-Tumor Efficacy of Alky Chain Modified TLR7/8 Agonists in CT26 Colon Carcinoma Bearing Wild-Type Mice The effect of repeated weekly doses of intratumorally delivered pharmaceutical compositions comprised of Compound No. 63-10, 63-18, or 63-33 formulated in 95% sesame oil/5% ethanol (v/v) on tumor growth inhibition was assessed in syngeneic CT26 colon carcinoma-bearing Balb/c mice. All in vivo procedures were conducted in accordance with approved Institutional Animal Care and Use Committee (IACUC) protocols. The animals were housed in a facility that is accredited by the Association for Accreditation and Laboratory Animal Care (AALAC, Frederick, Md.). Wild-type female Balb/c mice (15-20 gm) were obtained from Envigo (Hayward, Calif.) and acclimated for 2-3 days prior to use.

The pharmaceutical compositions were made with the three compounds at final concentrations of 5, 50, and 200 µg/mL in a manner similar to that described in Example B2-1. A TLR9 CpG agonist that has previously demonstrated efficacy in this murine tumor model was used as a positive control (Wang et al 2016 PNAS 113:E7240-E7249). On day 0, mice were anesthetized with 1% isoflurane and 80,000 CT26 tumor cells in 200 uL of RMPI-1640 culture media plus 2.5% fetal bovine serum were injected subcutaneously in the right flank. Tumors were allowed to grow until they were ~35 mm³, at which point animals were assigned to groups to begin treatment. Mice were injected weekly for 4 weeks intratumorally with 100 uL of a pharmaceutical composition comprising 20, 5, or 0.5 µgs of Compound No. 63-10, or 20 or 5 µgs of Compound Nos. 63-18, or 63-33 formulated in 95% sesame oil/5% ethanol (v/v), or a vehicle control, twice weekly for 3 weeks (experimental days 9, 12, 16, 19, 23, and 26). The TLR9 CpG agonist was injected intratumorally with 100 µL of a pharmaceutical composition comprised of 50 µgs of compound formulated in phosphate buffered saline on the same dosing schedule. Tumor sizes were measured twice weekly from days 8 through day 30 with calipers, with tumor volumes calculated using the formula: length, multiplied by width, multiplied by width, divided by 2.

Figure 2C:
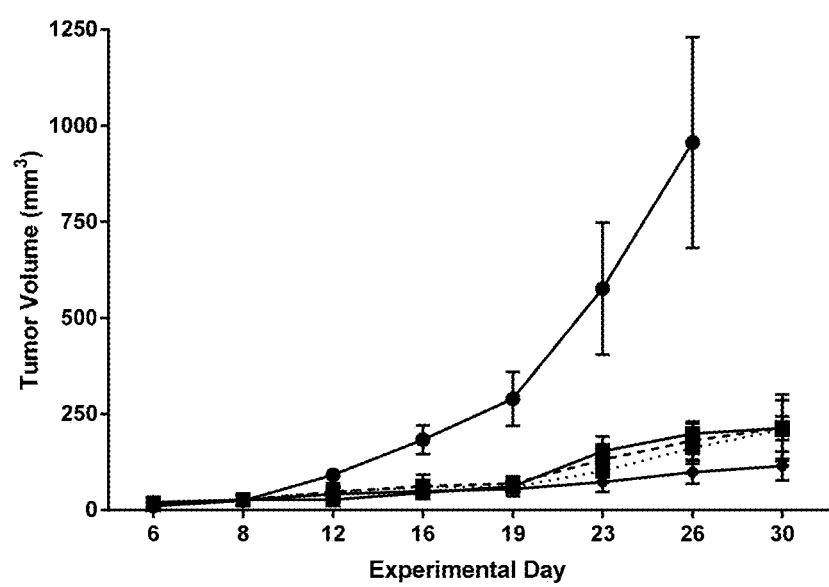

Compound Nos. 63-10, 63-18, and 63-33 demonstrated robust CT26 tumor growth control over the range of doses tested compared to the vehicle control (FIG. 2). The level of tumor growth control observed for Compound Nos. 63-10, 63-18, and 63-33 was comparable to that of the TLR9 CpG. These data demonstrate that the TLR7/8 agonists of the current invention possess potent anti-tumor effects in this syngeneic mouse tumor growth model system that show greater tumor growth control compared to the vehicle control (and are comparable to tumor growth inhibition by TLR9 CpGs). These data are consistent with the interpretation that tumor growth inhibition for Compound Nos. 63-10, 63-18, and 63-33 correlates with their TLR7 agonist bioactivity in vitro (see e.g., Tables B1-1 and B1-2) and is independent of their alkyl chain length modifications.

Example B5. Anti-Tumor Efficacy of Alky Chain Modified TLR7/8 Agonists Co-Administered with Tumor Associated Antigens in Two Flank CT26 Colon Carcinoma-Bearing Wild-Type Mice The effect of repeated weekly doses of intratumorally-delivered pharmaceutical compositions comprised of Compound No. 63-10 formulated in a squalene-based oil-in-water nanoemulsion that was co-formulated with the CT-26 tumor associated AH-1 class II peptide (immunodominant epitope sequence from the endogenous retroviral gene product gp70; see e.g., Rice J, Buchan S and Stevenson F 2002 J Immunol 169:3908-3913) on injected and distal tumor growth inhibition was assessed in CT26 colon carcinoma-bearing Balb/c mice bearing tumors in 2 flanks. All in vivo procedures were conducted in accordance with approved IACUC protocols. The animals were housed in a facility that is accredited by the AALAC. Wild-type female Balb/c mice (15-20 g) were obtained from Envigo (Hayward, Calif.) and acclimated for 2-3 days prior to use.

Pharmaceutical compositions comprised of squalene-based oil-in-water nanoemulsions were made generally as described in Example B2-2. In addition to a control squalene-based oil-in-water nanoemulsion, additional nanoemulsions were made that incorporated either Compound No. 63-10 alone at a 500 ng/mL final concentration, or Compound No. 63-10 at a 500 ng/mL final concentration plus the AH-1 class II peptide at a 500,000 ng/mL final concentration. For the latter pharmaceutical composition, the AH-1 peptide was initially dissolved at 2× concentration in phosphate buffered saline, then formulated into the squalene-based oil-in-water nanoemulsion during the final mixing step to yield a final concentration in the nanoemulsion of 500,000 ng/mL. On day 0, mice were anesthetized with 1% isoflurane, and 80,000 CT26 tumor cells in 200 uL of RMPI-1640 culture media with 2.5% fetal bovine serum were injected subcutaneously in both the right and left flanks. Tumors were allowed to grow until day 8, when the average tumor sizes had reached approximately 50 mm$^3$, at which time mice were randomized into groups and injected intratumorally in the right flank tumor with 100 uL of the squalene-based oil-in-water nanoemulsion vehicle control, nanoemulsion containing 50 ng of Compound No. 63-10, or nanoemulsion containing 50 ng of Compound No. 63-10 plus 50,000 ng of AH-1 tumor antigen peptide. These three pharmaceutical compositions were further injected into the right flank tumor on experimental days 12, 16, and 20. Right (injected) and left (distal) tumor volumes were then measured twice weekly from days 8 through day 30 with calipers, with tumor volumes calculated using the formula: length, multiplied by width, multiplied by width, divided by 2.

Figure 3A:
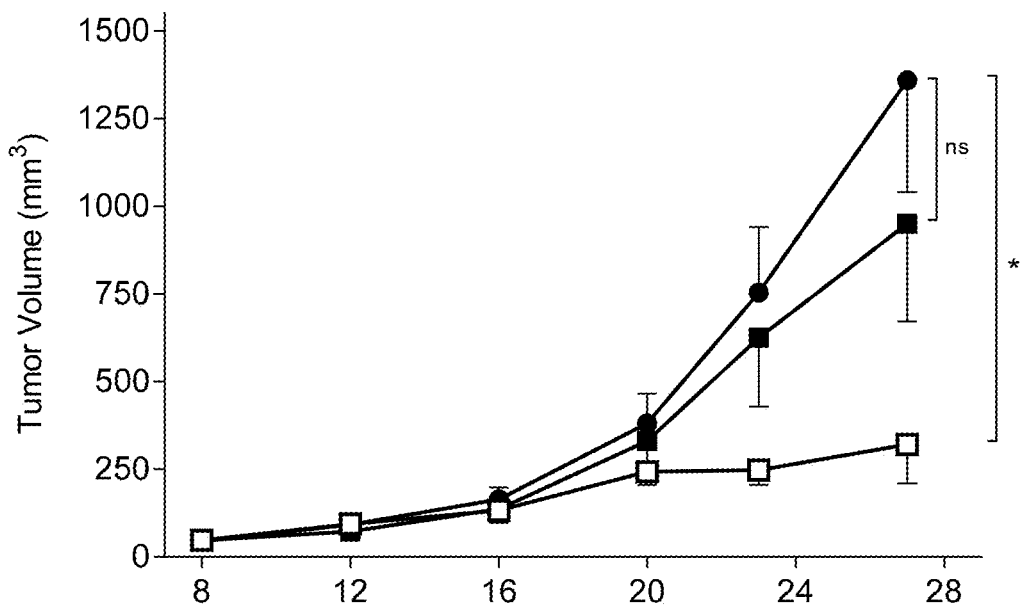
FIGS. 3A-B show tumor growth inhibition over time in the injected (FIG. 3A) and distal (FIG. 3B) tumors of CT26 tumor-bearing wild-type mice following repeated intratumoral administration of pharmaceutical compositions comprised of a squalene-based oil-in-water nanoemulsion vehicle control (-●-), a squalene-based oil-in-water nanoemulsion with 50 ng Compound No. 63-10 (-■-), or a squalene-based oil-in-water nanoemulsion with 50 ng Compound No. 63-10 plus 50,000 ng AH-1 class II peptide (-□-) as described in Example B5. Animals were dosed as described on experimental days 8, 12, 16, and 20. Group size=8 for controls and all experimental conditions, the data is expressed as average tumor volume (in $mm^3$) +/−standard error of the mean. Differences in tumor volumes between groups on day 27 for the injected tumor, or on day 23 for the distal tumor, were analyzed using a Kruskall-Wallis test followed by Dunn's post-test for specific group pair comparisons. ns indicates P≥0.050; * indicates P≤0.050.
Figure 3B:
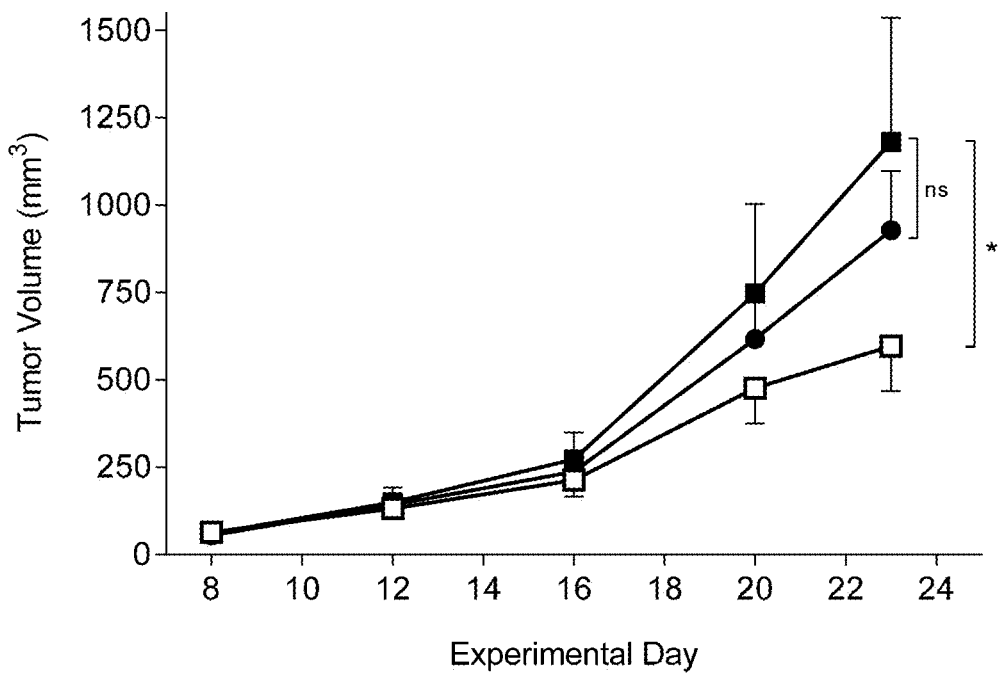

The pharmaceutical composition comprised of a squalene-based oil-in-water nanoemulsion containing 50 ng of Compound Nos. 63-10 demonstrated a trend towards greater tumor growth inhibition in the injected (right) tumor compared to the nanoemulsion vehicle control (FIG. 3A); however, this tumor growth inhibition was not significantly different from the vehicle control at day 27. In contrast, the pharmaceutical composition comprised of a squalene-based oil-in-water nanoemulsion containing 50 ng of Compound Nos. 63-10 plus 50,000 ng of AH-1 tumor associated peptide demonstrated significantly greater tumor growth inhibition in the injected (right) tumor compared to the nanoemulsion vehicle control at day 27. Additionally, the pharmaceutical composition comprised of a squalene-based oil-in-water nanoemulsion containing 50 ng of Compound Nos. 63-10 demonstrated a trend towards greater tumor growth inhibition in the distal (left) tumor compared to the nanoemulsion vehicle control (FIG. 3B); however, this tumor growth inhibition was not significantly different from the vehicle control at day 23. In contrast, the pharmaceutical composition comprised of a squalene-based oil-in-water nanoemulsion containing 50 ng of Compound Nos. 63-10 plus 50,000 ng of AH-1 tumor associated peptide demonstrated significantly greater tumor growth inhibition in the distal (left) tumor compared to the nanoemulsion vehicle control at day 23. These data are consistent with the interpretation that injected and distal tumor growth inhibition by Compound No. 63-10 is superior when it is co-delivered to antigen presenting cells in the tumor microenvironment with an exogenously added CT26 tumor-associated antigen.

Example B6. Anti-Tumor Efficacy of Alky Chain Modified TLR7/8 Agonists in Combination with Immune Checkpoint Inhibition in Dual Flank CT26 Colon Carcinoma-Bearing Wild-Type Mice The effect of intratumorally delivered pharmaceutical compositions comprised of Compound No. 63-10 or 63-33 formulated in 95% sesame oil/5% ethanol (v/v), or Compound No. 63-00 formulated in phosphate-buffered saline, given in combination with intraperitoneally delivered anti-mouse PD-1 (CD279) antibody (an immune checkpoint inhibitor; Bio X Cell, Lebanon N.H.), on tumor growth inhibition was assessed in CT26 colon carcinoma-bearing Balb/c mice bearing tumors in 2 flanks. All in vivo procedures were conducted in accordance with approved IACUC protocols. The animals were housed in a facility that is accredited by the AALAC. Wild-type female Balb/c mice (15-20 g) were obtained from Envigo (Hayward, Calif.) and acclimated for 2-3 days prior to use.

The pharmaceutical compositions were made using Compound No. 63-10 or 63-33 at final concentrations of 50,000 ng/mL in a manner similar to that described for Example B2-1. The pharmaceutical composition of Compound No. 63-00 was made using phosphate-buffered saline at a final concentration of 50,000 ng/mL. On day 0, mice were anesthetized with 1% isoflurane, and 80,000 CT26 tumor cells in 200 uL of RMPI-1640 culture media plus 2.5% fetal bovine serum were injected subcutaneously in both the right and left flanks. Tumors (left and right) were allowed to grow until day 8, when the right and left flank tumor sizes had reached approximately 35 mm$^3$, at which point mice were injected intraperitoneally with 250 µg of anti-PD-1 antibody formulated in phosphate buffered saline or a phosphate buffered saline vehicle control. The anti-PD-1 treatments were repeated on experimental days 12, 15, 19, 22, and 26. On experimental day 14, when the right (injected) and left (distal) flank tumors had reached approximately 100 mm$^3$, mice were randomized into treatment groups. The anti-PD-1 plus treatment groups were additionally injected intratumorally in the right flank tumor only with 100 uL of a pharmaceutical composition comprising 5,000 ng of Compound No. 63-00 in phosphate buffered saline, 5,000 ng of Compound No. 63-10 in 95% sesame oil/5% ethanol (v/v), or 5,000 ng of Compound No. 63-33 in 95% sesame oil/5% ethanol (v/v). Tumor sizes were measured twice weekly from days 14 through day 29 with calipers, with tumor volumes calculated using the formula: length, multiplied by width, multiplied by width, divided by 2.

Figure 4A:
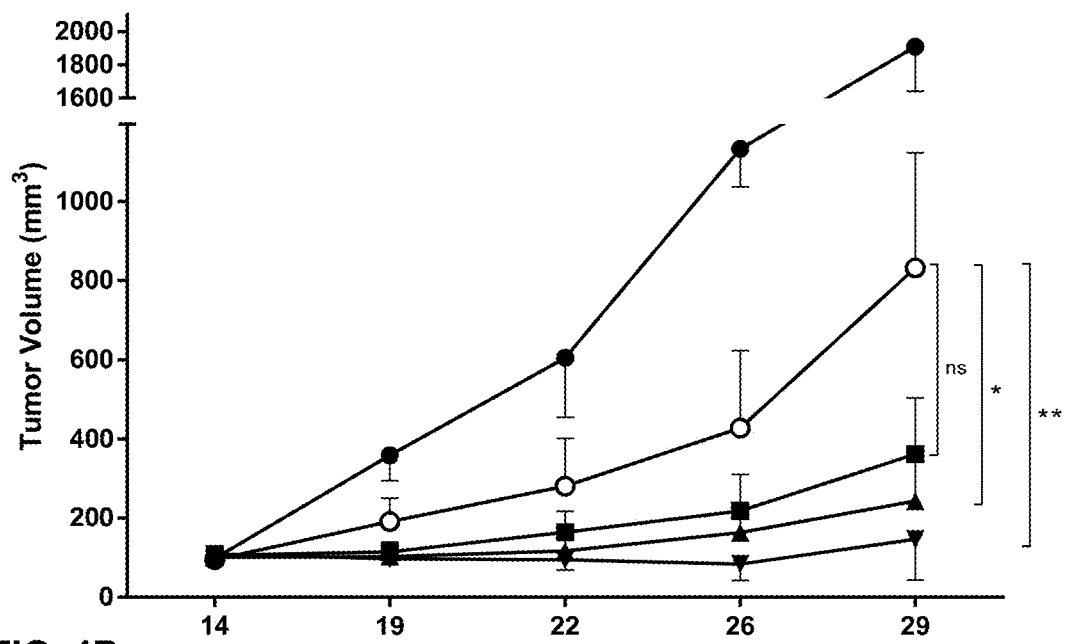
FIGS. 4A-B show tumor growth inhibition over time in the injected (FIG. 4A) and distal (FIG. 4B) tumors of CT26 tumor-bearing wild-type mice following a single intratumoral administration on experimental day 14 of pharmaceutical compositions comprised of phosphate buffered saline vehicle control (-●-), phosphate buffered saline vehicle control in combination with 250 µg of anti-PD-1 antibody (-○-), 5,000 ng of Compound No. 63-10 in 95% sesame oil/5% ethanol (v/v) in combination with 250 µg of anti-PD-1 antibody (-■-), 5,000 ng of Compound No. 63-33 in 95% sesame oil/5% ethanol (v/v) in combination with 250 µg of anti-PD-1 antibody (-▲-), or 5,000 ng of Compound No. 63-00 in phosphate buffered saline in combination with 250 µg of anti-PD-1 antibody (-▼-) as described in Example B6. For all the treatment groups with an anti-PD-1 combination, the anti-PD-1 treatment was administered intraperitoneally on experimental days 12, 15, 19, 22, and 26. Group size=10 for controls and all experimental conditions, the data is expressed as average tumor volume (in $mm^3$)+/−standard error of the mean. Differences in tumor volumes between groups on experimental day 29 were analyzed using a Kruskall-Wallis test followed by Dunn's post-test for specific group pair comparisons. ns indicates P≥0.050; * indicates P≤0.050; ** P≤0.010.
Figure 4B:
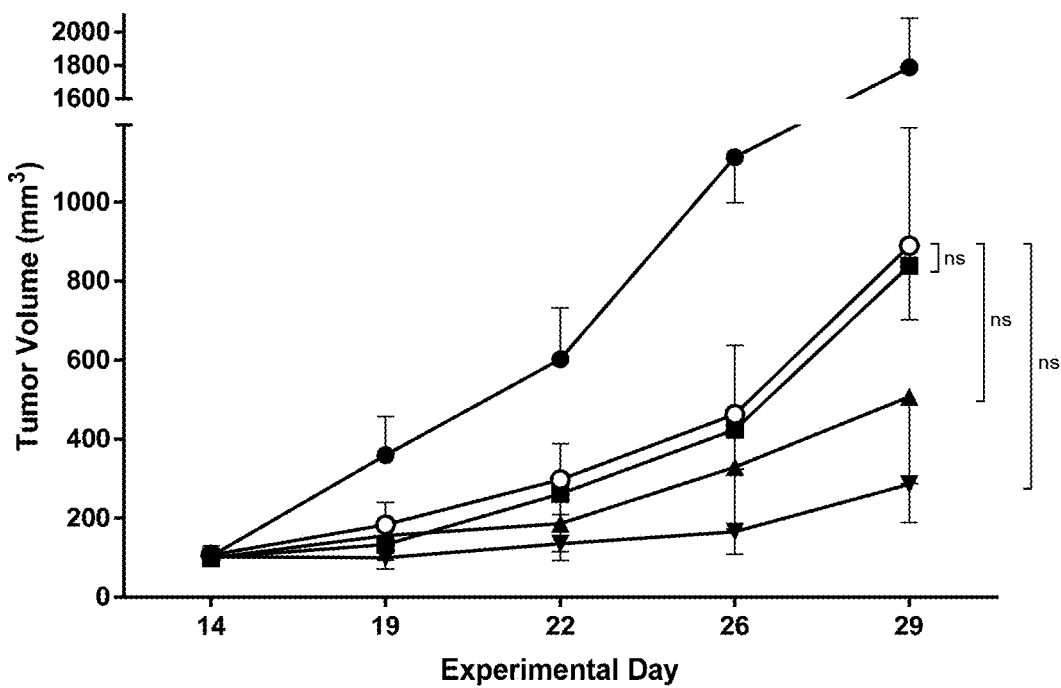

The pharmaceutical compositions comprised of 5,000 ng of Compound No. 63-00, 63-10, or 63-33 in combination with anti-PD-1 treatment demonstrated greater tumor growth inhibition in the injected tumor (right flank) compared to the anti-PD-1 treatment alone (FIG. 4A). This tumor growth inhibition was significantly different from the anti-PD-1 treatment control at day 29 for Compound Nos. 63-33 and 63-00. Additionally, the pharmaceutical compositions comprised of 5,000 ng of Compound Nos. 63-00 or 60-33 in combination with anti-PD-1 treatment demonstrated a trend towards greater tumor growth inhibition in the distal tumor (left flank) compared to the anti-PD-1 treatment alone (FIG. 4B), although this tumor growth inhibition did not reach statistical significance from the anti-PD-1 treatment control at day 29. The pharmaceutical composition comprised of 5,000 ng of Compound No. 63-10 in combination with anti-PD-1 treatment demonstrated no improvement in distal tumor growth inhibition compared to the anti-PD-1 treatment alone. These data are consistent with the interpretation that Compound No. 63-33, in combination with the immune checkpoint inhibitor anti-PD-1, is superior at controlling both injected and distal CT26 tumor growth compared to treatment with vehicle control plus anti-PD-1.

All publications, including patents, patent applications, and scientific articles, mentioned in this specification are herein incorporated by reference in their entirety for all purposes to the same extent as if each individual publication, including patent, patent application, or scientific article, were specifically and individually indicated to be incorporated by reference.

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention.

What is claimed is:

1. A compound of the following formula:

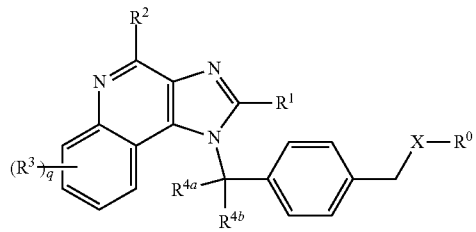

or a salt thereof, wherein:
$R^0$ is —$(CH_2)_z(C(CH_3)_2)R^A$ or —$(CH_2)_m R^A$;
m is 0, 1, 2, or 3;
z is 1 or 2;
$R^A$ is $C_3$-$C_8$ cycloalkyl optionally substituted by 1 to 4 groups independently selected from the group consisting of $C_1$-$C_4$ alkyl, $C_1$-$C_4$ alkylene, and halogen;
X is —NH—;
$R^1$ is $C_3$-$C_6$ alkyl, —$(CH_2)_p OR^{1a}$, —$(CH_2)_p NHR^{1b}$ or —$(CH_2)_p R^{1c}$; where $R^{1a}$ and $R^{1b}$ are independently $C_1$-$C_3$ alkyl; $R^{1c}$ is $C_3$-$C_4$ cycloalkyl; and p is 1 or 2;
$R^2$ is $NHR^{2a}$; where $R^{2a}$ is H, OH, $NH_2$, or methyl;
each $R^3$ is independently halogen, $C_1$-$C_8$ alkyl, —($C_1$-$C_7$ alkylene)-$NH_2$, or —$CH_2$-phenylene-$CH_2NH_2$;
q is 0, 1, 2, 3, or 4; and
$R^{4a}$ and $R^{4b}$ are independently H or $C_1$-$C_8$ alkyl.

2. The compound of claim 1, or a salt thereof, wherein $R^0$ is —$(CH_2)_m R^A$.

3. The compound of claim 2, or a salt thereof, wherein m is 2.

4. The compound of claim 1, or a salt thereof, wherein $R^0$ is —$(CH_2)_z(C(CH_3)_2)R^A$.

5. The compound of claim 4, or a salt thereof, wherein z is 1.

6. The compound of claim 2, or a salt thereof, wherein $R^A$ is cyclopropyl, cyclobutyl, or cyclopentyl.

7. The compound of claim 2, or a salt thereof, wherein $R^A$ is $C_3$-$C_6$ cycloalkyl optionally substituted by 1 to 3 groups independently selected from the group consisting of methyl, methylene, and halogen.

8. The compound of claim 1, or a salt thereof, wherein m is 1 or 2.

9. The compound of claim 8, or a salt thereof, wherein $R^A$ is $C_3$-$C_8$ cycloalkyl.

10. The compound of claim 8, or a salt thereof, wherein $R^A$ is cyclopropyl optionally substituted by 1 to 3 groups independently selected from the group consisting of methyl and methylene.

11. The compound of claim 1, or a salt thereof, wherein m is 0 and $R^A$ is cyclohexyl optionally substituted by 1 to 3 groups independently selected from the group consisting of methyl and methylene.

12. The compound of claim 1, or a salt thereof, wherein $R^0$ is selected from the group consisting of:

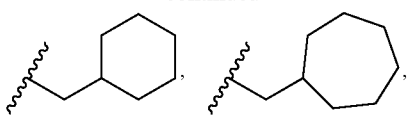

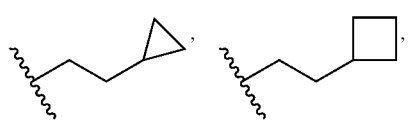

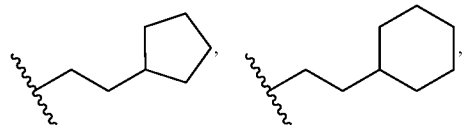

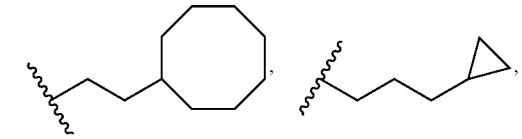

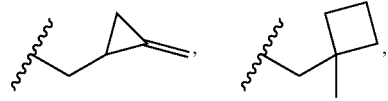

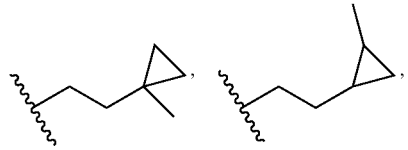

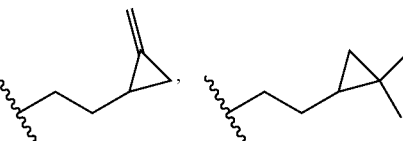

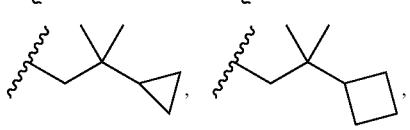

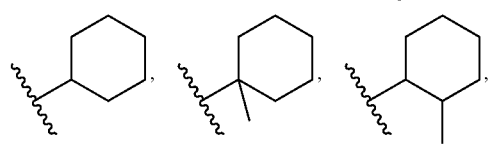

and 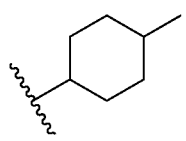.

13. The compound of claim 1, which is Compound No. 63-33, 63-35, 63-36, or 63-38 to 63-49:

| Compound No. | Formula |
|---|---|
| 63-33 | (structure: 4-amino-2-butyl-imidazoquinoline with 1-(4-((2-cyclopropylethylamino)methyl)benzyl) substituent) |
| 63-35 | (structure: 4-amino-2-butyl-imidazoquinoline with 1-(4-((2-cyclobutylethylamino)methyl)benzyl) substituent) |
| 63-36 | (structure: 4-amino-2-butyl-imidazoquinoline with 1-(4-((2-cyclopentylethylamino)methyl)benzyl) substituent) |
| 63-38 | (structure: 4-amino-2-butyl-imidazoquinoline with 1-(4-((cyclopropylmethylamino)methyl)benzyl) substituent) |
| 63-39 | (structure: 4-amino-2-butyl-imidazoquinoline with 1-(4-(((2-methylcyclopropyl)methylamino)methyl)benzyl) substituent) |
| 63-40 | (structure: 4-amino-2-butyl-imidazoquinoline with 1-(4-(((2,2-dimethylcyclopropyl)methylamino)methyl)benzyl) substituent) |
| 63-41 | (structure: 4-amino-2-butyl-imidazoquinoline with 1-(4-(((2-cyclopropylpropan-2-yl)methylamino)methyl)benzyl) substituent) |

-continued
| Compound No. | Formula |
|---|---|
| 63-42 | 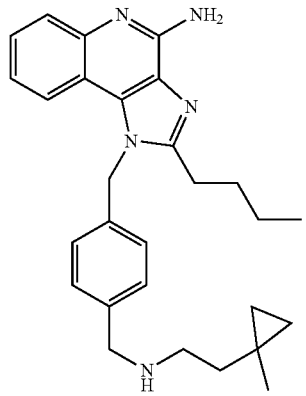 [SMILES: CCCCc1nc2c(N)nc3ccccc3c2n1Cc1ccc(CNCCC2(C)CC2)cc1] |
| 63-43 | 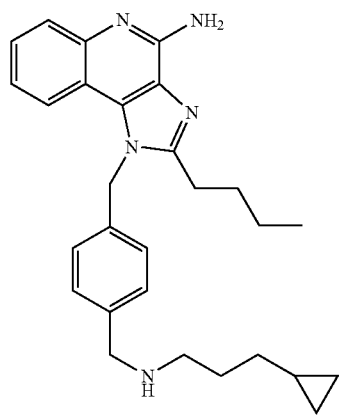 [SMILES: CCCCc1nc2c(N)nc3ccccc3c2n1Cc1ccc(CNCCCC2CC2)cc1] |
| 63-44 | 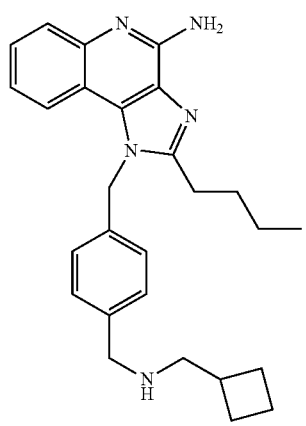 [SMILES: CCCCc1nc2c(N)nc3ccccc3c2n1Cc1ccc(CNCC2CCC2)cc1] |
-continued
| Compound No. | Formula |
|---|---|
| 63-45 | |
| 63-46 | |
| 63-47 | 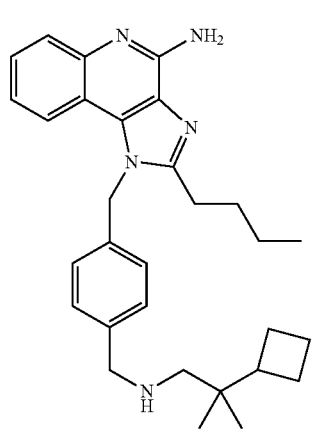 [SMILES: CCCCc1nc2c(N)nc3ccccc3c2n1Cc1ccc(CNCC(C)(C)C2CCC2)cc1] |

| Compound No. | Formula |
|---|---|
| 63-48 | (structure) |
| 63-49 | 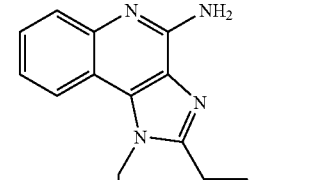 |
or a salt thereof.
14. A pharmaceutical composition comprising (i) the compound according to claim 1, or a salt thereof and (ii) a pharmaceutically acceptable excipient.
15. The pharmaceutical composition of claim 14, further comprising an antigen.
* * * * *